(12) United States Patent
Owens et al.

(10) Patent No.: US 10,533,013 B2
(45) Date of Patent: *Jan. 14, 2020

(54) SUBSTITUTED PYRAZOLO[3,4-D]PYRIMIDINES AS KINASE INHIBITORS

(71) Applicant: PRINCIPIA BIOPHARMA INC., South San Francisco, CA (US)

(72) Inventors: Tim Owens, San Carlos, CA (US); Erik Verner, Belmont, CA (US)

(73) Assignee: Principia Biopharma Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/978,041

(22) Filed: May 11, 2018

(65) Prior Publication Data
US 2018/0327413 A1    Nov. 15, 2018

Related U.S. Application Data

(63) Continuation of application No. 14/997,330, filed on Jan. 15, 2016, now Pat. No. 9,994,576, which is a continuation of application No. 14/374,788, filed as application No. PCT/US2013/058614 on Sep. 6, 2013, now Pat. No. 9,266,895.

(60) Provisional application No. 61/782,605, filed on Mar. 14, 2013, provisional application No. 61/728,693, filed on Nov. 20, 2012, provisional application No. 61/699,038, filed on Sep. 10, 2012.

(51) Int. Cl.
| | | |
|---|---|---|
| *A61K 31/519* | (2006.01) |
| *C07D 487/04* | (2006.01) |
| *C07D 519/00* | (2006.01) |
| *A61K 31/495* | (2006.01) |
| *A61K 31/506* | (2006.01) |
| *C07D 401/14* | (2006.01) |
| *C07D 403/12* | (2006.01) |
| *C07D 405/12* | (2006.01) |
| *A61K 31/5377* | (2006.01) |
| *A61K 45/06* | (2006.01) |
| *A61K 9/00* | (2006.01) |

(52) U.S. Cl.
CPC .......... *C07D 487/04* (2013.01); *A61K 9/0053* (2013.01); *A61K 31/495* (2013.01); *A61K 31/506* (2013.01); *A61K 31/519* (2013.01); *A61K 31/5377* (2013.01); *A61K 45/06* (2013.01); *C07D 401/14* (2013.01); *C07D 403/12* (2013.01); *C07D 405/12* (2013.01); *C07D 519/00* (2013.01)

(58) Field of Classification Search
CPC ............................ A61K 31/519; C07D 487/04
USPC ...................................... 514/262.1; 544/262
See application file for complete search history.

(56) References Cited

U.S. PATENT DOCUMENTS

| | | |
|---|---|---|
| 4,721,710 A | 1/1988 | Bernhart et al. |
| 4,861,760 A | 8/1989 | Mazuel et al. |

(Continued)

FOREIGN PATENT DOCUMENTS

| | | |
|---|---|---|
| CN | 101610676 A | 12/2009 |
| CN | 101730699 A | 6/2010 |

(Continued)

OTHER PUBLICATIONS

Armesto et al., "Efficient photochemical synthesis of 2-vinylcyclopropanecarbaldehydes, precursors of cyclopropane components present in pyrethroids, by using the oxa-di-π-methane rearrangement," *Tetrahedron*, 66: 8690-8697 (2010).

(Continued)

*Primary Examiner* — Douglas M Willis
(74) *Attorney, Agent, or Firm* — Finnegan, Henderson, Farabow, Garrett & Dunner, LLP

(57) ABSTRACT

The present disclosure provides compounds of Formula (IA), such as, e.g.,
(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile having the chemical structure

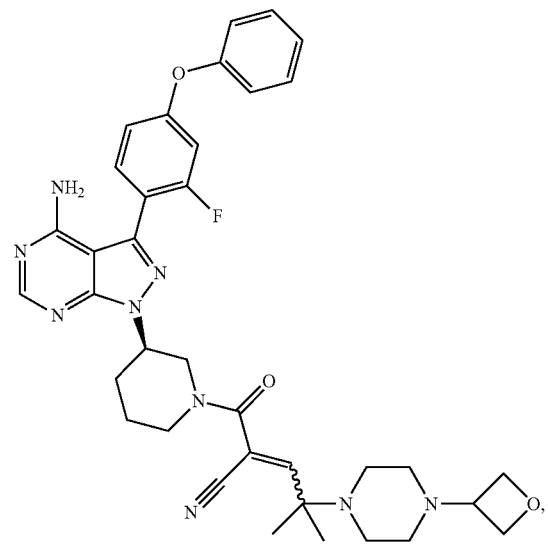

and/or pharmaceutically acceptable salts thereof that are tyrosine kinase inhibitors, in particular BTK inhibitors, and are potentially useful for the treatment of diseases treatable by inhibition of tyrosine kinases such as cancer, inflammatory diseases such as arthritis, and the like. Also provided are pharmaceutical compositions containing such compounds and/or pharmaceuti- (Continued)

cally acceptable salts thereof and processes for preparing such compounds and pharmaceutically acceptable salts thereof.

10 Claims, No Drawings

(56) References Cited

U.S. PATENT DOCUMENTS

| | | |
|---|---|---|
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1 | 3/2014 | Goldstein |
| 8,759,358 B1 | 6/2014 | Goldstein |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens et al. |
| 9,994,576 B2 | 6/2018 | Owens et al. |
| 10,092,569 B2 | 10/2018 | Masjedizadeh et al. |
| 2003/0153752 A1 | 8/2003 | Hirst et al. |
| 2003/0187001 A1 | 10/2003 | Calderwood et al. |
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |
| 2006/0079494 A1 | 4/2006 | Santi et al. |
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |
| 2008/0076921 A1 | 3/2008 | Honigberg et al. |
| 2008/0146643 A1 | 6/2008 | Billen et al. |
| 2008/0176865 A1 | 7/2008 | Billen et al. |
| 2008/0260818 A1 | 10/2008 | Penhasi et al. |
| 2009/0215750 A1 | 8/2009 | Bamberg et al. |
| 2009/0215788 A1 | 8/2009 | Elworthy et al. |
| 2009/0306396 A1 | 12/2009 | Toyoshima et al. |
| 2010/0113520 A1 | 5/2010 | Miller |
| 2010/0144705 A1 | 6/2010 | Miller |
| 2010/0152143 A1 | 6/2010 | Priebe et al. |
| 2010/0254905 A1 | 10/2010 | Honigberg et al. |
| 2011/0021518 A1 | 1/2011 | Magnuson et al. |
| 2011/0086866 A1 | 4/2011 | Chen et al. |
| 2012/0028981 A1 | 2/2012 | Miller |
| 2012/0071497 A1 | 3/2012 | Buggy et al. |
| 2013/0079327 A1 | 3/2013 | Yamamoto et al. |
| 2013/0197014 A1 | 8/2013 | Chen et al. |
| 2014/0094459 A1 | 4/2014 | Goldstein et al. |
| 2014/0142099 A1 | 5/2014 | Owens |
| 2014/0221398 A1 | 8/2014 | Goldstein et al. |
| 2014/0256734 A1 | 9/2014 | Lawson et al. |
| 2014/0303190 A1 | 10/2014 | Goldstein |
| 2014/0364410 A1 | 12/2014 | Owens et al. |
| 2015/0140085 A1 | 5/2015 | Goldstein |
| 2015/0353557 A1 | 12/2015 | Goldstein et al. |
| 2015/0353562 A1 | 12/2015 | Goldstein |
| 2016/0045503 A1 | 2/2016 | Goldstein et al. |
| 2016/0257686 A1 | 9/2016 | Owens |
| 2016/0376277 A1 | 12/2016 | Desai et al. |
| 2018/0015088 A1 | 1/2018 | Nunn et al. |
| 2018/0050027 A1 | 2/2018 | Gourlay |
| 2018/0162861 A1 | 6/2018 | Goldstein et al. |
| 2018/0193274 A1 | 7/2018 | Nunn et al. |
| 2018/0305350 A1 | 10/2018 | Goldstein et al. |
| 2018/0327413 A1 | 11/2018 | Owens et al. |
| 2019/0076435 A1 | 3/2019 | Masjedizadeh et al. |

FOREIGN PATENT DOCUMENTS

| | | |
|---|---|---|
| CN | 101805341 A | 8/2010 |
| CN | 101880243 A | 11/2010 |
| CN | 102159214 A | 8/2011 |
| CN | 103096716 A | 5/2013 |
| CN | 103534258 A | 1/2014 |
| CN | 104640861 A | 5/2015 |
| CN | 105753863 A | 7/2016 |
| EP | 0461546 A2 | 12/1991 |
| EP | 0493767 A2 | 7/1992 |
| EP | 0908457 A1 | 4/1999 |
| EP | 2443929 A1 | 4/2012 |
| EP | 2578585 A1 | 4/2013 |
| FR | 2535721 A1 | 5/1984 |
| GB | 2447933 A | 10/2008 |
| JP | 42008308 B4 | 4/1967 |
| JP | 56-63950 A | 5/1981 |
| JP | 200-1450 | 1/1990 |
| JP | 04-177244 A | 6/1992 |
| JP | 2005-239657 A | 9/2005 |
| JP | 2010504324 A | 2/2010 |
| JP | 2010-235628 A | 10/2010 |
| JP | 2014-513729 A | 6/2014 |
| JP | 2014-517838 A | 7/2014 |
| JP | 6203848 | 9/2017 |
| WO | WO 1995/24190 | 9/1995 |
| WO | WO 95/31432 A1 | 11/1995 |
| WO | WO 98/41499 A1 | 9/1998 |
| WO | WO 1999/14216 | 3/1999 |
| WO | WO 01/72751 A1 | 10/2001 |
| WO | WO 02/066463 A1 | 8/2002 |
| WO | WO 03/037890 A2 | 5/2003 |
| WO | WO 03/050080 A1 | 6/2003 |
| WO | WO 2003/068157 A2 | 8/2003 |
| WO | WO 03/082807 A2 | 10/2003 |
| WO | WO 2004/016259 A1 | 2/2004 |
| WO | WO 2004/074283 A1 | 9/2004 |
| WO | WO 2005/023773 A1 | 3/2005 |
| WO | WO 2005/030184 A2 | 4/2005 |
| WO | WO 2005/085210 A1 | 9/2005 |
| WO | WO 2006/086634 A2 | 8/2006 |
| WO | WO 2006/134468 A1 | 12/2006 |
| WO | WO 2007/043401 A2 | 4/2007 |
| WO | WO 2007/087068 A2 | 8/2007 |
| WO | WO 2007/130075 A1 | 11/2007 |
| WO | WO 2007/142755 A2 | 12/2007 |
| WO | WO 2008/005954 A2 | 1/2008 |
| WO | WO 2008/006032 A1 | 1/2008 |
| WO | WO 2008/039218 A2 | 4/2008 |
| WO | WO 2008/054827 A2 | 5/2008 |
| WO | WO 2008/061740 A1 | 5/2008 |
| WO | WO 2008/072053 A2 | 6/2008 |
| WO | WO 2008/072077 A2 | 6/2008 |
| WO | WO 2008/116064 A2 | 9/2008 |
| WO | WO 2008/121742 A2 | 10/2008 |
| WO | WO 2009/140128 A2 | 11/2009 |
| WO | WO 2009/143477 A1 | 11/2009 |
| WO | WO 2010/009342 A2 | 1/2010 |
| WO | WO 2010/014930 A2 | 2/2010 |
| WO | WO 2010/065898 A2 | 6/2010 |
| WO | WO 2011/031896 A2 | 3/2011 |
| WO | WO 2011/046964 A2 | 4/2011 |
| WO | WO 2011/060440 A2 | 5/2011 |
| WO | WO 2011/144585 A1 | 11/2011 |
| WO | WO 2011/152351 A1 | 12/2011 |
| WO | WO 2011/153514 A2 | 12/2011 |

(56) References Cited

FOREIGN PATENT DOCUMENTS

| | | |
|---|---|---|
| WO | WO 2012/021444 A1 | 2/2012 |
| WO | WO 2012/158764 A1 | 11/2012 |
| WO | WO 2012/158795 A1 | 11/2012 |
| WO | WO 2012/158810 A1 | 11/2012 |
| WO | WO 2012/158843 A2 | 11/2012 |
| WO | WO 2013/003629 A2 | 1/2013 |
| WO | WO 2013/010136 A2 | 1/2013 |
| WO | WO 2013/010380 A1 | 1/2013 |
| WO | WO 2013/010868 A1 | 1/2013 |
| WO | WO 2013/010869 A1 | 1/2013 |
| WO | WO 2013/041605 A1 | 3/2013 |
| WO | WO 2013/059738 A1 | 4/2013 |
| WO | WO 2013/102059 A1 | 7/2013 |
| WO | WO 2013/116382 A1 | 8/2013 |
| WO | WO 2013/185082 A2 | 12/2013 |
| WO | WO 2013/191965 A1 | 12/2013 |
| WO | WO 2014/004707 A1 | 1/2014 |
| WO | WO 2014/022569 A1 | 2/2014 |
| WO | WO 2014/039899 A1 | 3/2014 |
| WO | WO 2014/068527 A1 | 5/2014 |
| WO | WO 2014/078578 A1 | 5/2014 |
| WO | WO 2014/164558 A1 | 10/2014 |
| WO | WO 2015/127310 A1 | 8/2015 |
| WO | WO 2015/132799 A2 | 9/2015 |
| WO | WO 2017/041536 A1 | 3/2017 |
| WO | WO 2017/066014 A1 | 4/2017 |

OTHER PUBLICATIONS

Arnold, Lee D. et al., "Pyrrolo[2,3-d]pyrimidines Containing an Extended 5-Substituent as Potent and Selective Inhibitors of lck I," *Bioorganic & Medicinal Chemistry Letters*, 10:2167-2170 (2000).

Basheer, A., et al., "Enols of Substituted Cyanomalonamides," *J. Org. Chem.* 72:5297-5312 (2007).

Bernhart et al., "Synthesis and antiarrhythmic activity of new [(Dialkylamino)alkyl]phridylacetamides," *J. Med. Chem.*, 26:451-455 (1983).

Burchat, A.F., et al., "Pyrrolo[2,3-d]pyrimidines Containing an Extended 5-Substituent as Potent and Selective Inhibitors of lck II," *Bioorganic & Medicinal Chemistry Letters*, 10:2171-2174 (2000).

Burini et al., "Efficient Synthesis of 4-Cyano 2,3-Dihydrooxazoles by Direct Amination of 2-Alkylidene 3-Oxo Nitriles," *Synlett*, 17: 2673-2675 (2005).

Calderwood, David J., et al., "Pyrrolo[2,3-d]pyrimidines Containing Diverse N-7 Substituents as Potent Inhibitors of Lck," *Bioorganic & Medicinal Chemistry Letters*, 12:1683-1686 (2002).

CAS RN 26272-41-3, Nov. 16, 1984.

Cohen, Michael S., et al., "Structural Bioinformatics-Based Design of Selective, Irreversible Kinase Inhibitors," *Science*, vol. 308, May 27, 2005.

Deng et al., "Reversible phospho-Smad$_3$ signalling between tumour suppression and fibrocarcinogenesis in chronic hepatitis B infection," *British Society for Immunology, Clinical and Experimental Immunology*, 176: 102-111 (2013).

Donald, Alastair, et al., "Rapid Evolution of 6-Phenylpurine Inhibitors of Protein Kinase B through Structure-Based Design," *J. Med. Chem.*, 50:2289-2292 (2007).

Elinson et al., "Electrochemical transformation of cyanoacetic ester and alkylidenecyanoacetic esters into 3-substituted 1,2-dicyanocyclopropane-1,2-dicarboxylates," *Russian Chemical Bulletin*, 47(6): 1133-1136 (1998).

Elliott et al., "The Pyrethrins and Related Compounds. Part XVIII. Insecticidal 2,2-Dimethylcyclopropanecarboxylates with New Unsaturated 3-Substituents," *Journal of the Chemical Society*, Perkin Transactions 1: Organic and Bio-Organic Chemistry (1972-1999) (1974), (21), 2470-4.

Elliott et al., "Insecticidal activity of the pyrethrins and related compounds X. *5-benzyl-3-furylmethyl 2,2-dimethyicyclopropanecarboxylates with ethylenic substituents at position 3 on the cyclopropane ring," *Pectic. Sci.*, 7: 499-502 (1976).

Extended European Search Report for European Patent Application No. 17152898.7, dated Mar. 8, 2017 (8 pages).

Fioravanti et al., "Parallel Solution-Phase Synthesis of Acrylonitrile Scaffolds Carrying $_L$-α-Amino Acidic or D-Glycosyl Residues," *J. Comb. Chem.*, 8: 808-811 (2006).

Gyoung et al, "Regiospecific synthesis of 2-allylated-5-substituted tetrazoles via palladium-catalyzed reaction of nitrites, trimethylsilyl azide, and allyl acetates," *Tetrahedron Letters*, 41(21): 4193-4196 (2000).

Hackman et al., "Translation of research evidence from animals to humans," *JAMA*, 296(14):1731-1732 (2006).

International Preliminary Report on Patentability for International Application No. PCT/US2010/056890, dated May 22, 2012.

International Search Report, PCT/US2010/056890, dated Jul. 28, 2011.

Jenner, "Steric effects in high pressure Knoevenagel reactions," *Tetrahedron Letters*, 42(2): 243-245 (2001).

Jordan, "Tamoxifen: a most unlikely pioneering medicine," *Nature Reviews Drug Discovery*, 2: 205-213 (2003).

Kamath, S. and Buolamwini John K., "Receptor-Guided Alignment-Based Comparative 3D-QSAR Studies of Benzylidene Malonitrile Tyrphostins as EGFR and HER-2 Kinase Inhibitors," *J. Med. Chem.*, 46:4657-4668 (2003).

Kamijo et al., "Tetrazole synthesis via the palladium-catalyzed three component coupling reaction," *Molecular Diversity*, 6: 181-192 (2003).

Knight, Z.A., "A membrane capture assay for lipid kinase activity," *Nature Protocols*, vol. 2, No. 10 (2007).

Kojima et al., "Stereoselective synthesis of activated cyclopropanes with an α-pyridinium acetamide bearing an 8-phenylmenthyl group as the chiral auxiliary," *Tetrahedron Letters*, 45(18): 3565-3568 (2004).

Komura et al., "Layered silicate PLS-1: A new solid base catalyst for C—C bond forming reactions," *Catalysis Communications*, 8(4): 644-648 (2007).

Kotz et al., "The Action of Chloroform on Methylene and Methenyl Groups," *Journal fuer Praktische Chemie (Leipzig)*, Abstract, 74: 425-48 (1907).

Li Zhensu, *Medicinal Chemistry*, Chemical Industry Press, China, Mar. 3, 1981, pp. 435-436 (2 pages).

Lou et al., "Bruton's Tyrosine Kinase Inhibitors: Approaches to Potent and Selective Inhibition, Preclinical and Clinical Evaluation for Inflammatory Diseases and B Cell Malignancies," *J. Med. Chem.*, 55(10): 4539-4550 (2012).

Maas et al., "Conjugate Addition of Dialkylaluminum Chlorides to Alkylidenemalonic Acid Derivatives," *Synthesis*, 10: 1792-1798 (1999).

Maurya et al., "Catalyst-free stereoselective cyclopropanation of electron deficient alkenes with ethyl diazoacetate," *RSC Advances*, 3: 15600-15603 (2013).

Miller, Rand M., "Electrophilic Fragment-Based Design of Reversible Covalent Kinase Inhibitors," *J. Am. Chem. Soc.* 135(14):5298-5301 (2013).

Neplyuev, "Studies of triacylmethanes VII. 1,1,3,3-Tetraacyl-3-arylazo-1-propenes," *Zhurnal Organicheskoi Khimii*, Abstract, 15(3): 563-6 (1979).

Neplyuev, "Nitration and nitrosation of 1,1,3,3-tetraacy1-1-propenes" *Ukrainskii Khimicheskii Zhurnal (Russian Edition)*, Abstract, 49(2): 192-4 (1983).

Pan, Zhengying, et al., "Discovery of Selective Irreversible Inhibitors for Bruton's Tyrosine Kinase," *ChemMedChem*, 2:58-61 (2007).

Porter et al., "The discovery of potent, orally bioavailable pyrimidine-5-carbonitrile-6-alkyl CXCR2 receptor antagonists," *Bioorganic & Medicinal Chemistry Letters*, 24: 3285-3290 (2014).

Proenca, Fernanda and Costa, Marta, "A simple and eco-friendly approach for the synthesis of 2-imino and 2-oxo-2H-chromene-3-carboxamides," *Green Chem.*, 10:995-998 (2008).

Rellos, Peter et al., "Structure and Regulation of the Human Nek2 Centrosomal Kinase," *Journal of Biological Chemistry*, 282(9):6833-6842 (2007).

Sammes, M.P., et al., "α-Cyano-sulphonyl Chlorides : Their Preparation and Reactions with Amines, Alcohols, and Enamines," *J. Chem. Soc.* (C) 2151-2155 (1971).

(56) References Cited

OTHER PUBLICATIONS

Santilli Arthur A. and Osdene T.S., "8,9,10,11-Tetrahydro-12H-benzo[5,6]quinoxalino[2,3-e][1,4]diazepin-12-ones. Examples of a New Heterocyclic Ring System," *J. Org. Chem.*, 29:2066-2068 (1964).
Schwarz et al., "Novel Cyclopropyl β-Amino Acid Analogues of Pregabalin and Gabapentin That Target the $\alpha_2$-δ Protein," *J. Med. Chem.*, 48:3026-3035 (2005).
Serafimova, Iana M., et al., "Reversible targeting of noncatalytic cysteines with chemically tuned electrophiles," *Nature Chemical Biology*, 8, 471-476 (2012).
Stevens et al, "Synthesis of Substituted Cyclopropylphosphonates by Michael Induced Ring Closure (MIRC) Reactions," *Synlett*, 7: 1089-1092 (2002).
Structure-Based Search Results (May 9, 2011, 8:13 PM), SciFinder (2 pages).
Structure-Based Search Results (May 9, 2011, 8:23 PM), SciFinder (2 pages).
Structure-Based Search Results (May 9, 2011, 8:33 PM), SciFinder (2 pages).
Structure-Based Search Results (May 9, 2011, 9:06 PM), SciFinder (2 pages).
Structure-Based Search Results (May 10, 2011, 10:04 AM), SciFinder (6 pages).
Structure-Based Search Results (May 10, 2011, 10:20 AM), SciFinder (4 pages).
Structure-Based Search Results (May 10, 2011, 10:46 AM), SciFinder (4 pages).
Verhé et al., "Preparation of 2,2-Dialkylcyclopropanes Geminally Substituted with Electron-Withdrawing Groups," Synthesis, 7: 530-2 (1978).
Verhé et al., "Thermal Lactonization of Brominated Alkylidenemalonates: Synthesis of 2-Buten-4-Olides," *Bulletin des Societes Chimiques Belges*, 87(3): 215-222 (1978).
Verhé et al, "Synthesis of 1,1-Bis(Hydroxymethyl) Cyclopropanes," *Organic Preparations and Procedures International*, 13(1): 13-18 (1981).
Vo et al., "Transformations of Resin-Bound Pyridinium Ylides: I. A Stereoselective Synthesis of 2,2,3-Trisubstituted Cyclopropanecarboxylates," *Tetrahedron Letters*, 38(46): 7951-7954 (1997).
Wang, "Cyanoacetamide Multicomponent Reaction (I): Parallel Synthesis of Cyanoacetamides," *J. Comb. Chem.* 11:920-927 (2009).
Wang, Gary T., et al., "Substituted 4-amino-1H-pyrazolo[3,4-d]pyrimidines as multi-targeted inhibitors of insulin-like growth factor-I receptor (IGFIR) and members of ErbB-family receptor kinases," *Bioorganic & Medicinal Chemistry Letters*, 20:6067-6071 (2010).
Wells, Geoffrey et al., "Structural Studies on Bioactive Compounds, 32.[1] Oxidation of Tyrphostin Protein Tyrosine Kinase Inhibitors with Hypervalent Iodine Reagents," *J. Med. Chem.* 43:1550-1562 (2000).
Zhang et al., "Organic base catalyzed carbonyl allylation of methyl trifluoropyruvate with activated alkenes," *Tetrahedron*, 65: 83-86 (2009).
Zimmerman et al., "The Diverted Di-π-Methane Rearrangement; Mechanistic and Exploratory Organic Photochemistry," *Organic Letters*, 4(7): 1155-1158 (2002).
English Translation of Office Action dated Apr. 12, 2013, in Chinese Application No. 201080061570.1 (2 pages).
International Search Report and Written Opinion dated Jul. 5, 2012 for PCT Application No. PCT/US2012/038092.
PCT Notification of Transmittal, PCT International Search Report, and PCT Written Opinion for International Application No. PCT/US2012/038135, dated Jul. 25, 2012 (11 pages).
International Search Report dated Feb. 1, 2013 for PCT Application No. PCT/US2012/038214.
PCT Notification of Transmittal of the International Search Report and the Written Opinion of the International Searching Authority, or the Declaration for International Application No. PCT/US2013/058614, dated Nov. 5, 2013.
File History of U.S. Appl. No. 13/859,569, "Tyrosine Kinase Inhibitors" in the name of David Michael Goldstein, filed Apr. 9, 2013.
File History of U.S. Appl. No. 13/929,004, "Tyrosine Kinase Inhibitors" in the name of David Michael Goldstein et al., filed Jun. 27, 2013.
File History of U.S. Appl. No. 13/929,179, "Tyrosine Kinase Inhibitors" in the name of David Michael Goldstein, filed Jun. 27, 2013.
File History of U.S. Appl. No. 14/185,687, "Tyrosine Kinase Inhibitors" in the name of David Michael Goldstein, filed Feb. 20, 2014.
File History of U.S. Appl. No. 14/255,842, "Tyrosine Kinase Inhibitors" in the name of David Michael Goldstein, filed Apr. 17, 2014.
File History of U.S. Appl. No. 14/341,421, "Tyrosine Kinase Inhibitors" in the name of David Michael Goldstein, filed Jul. 25, 2014.
File History of U.S. Appl. No. 14/741,311. "Tyrosine Kinase Inhibitors" in the name of David Michael Goldstein, filed Jun. 16, 2015.
File History of U.S. Appl. No. 14/117,927, "Pyrazolopyrimidine Derivatives As Tyrosine Kinase Inhibitors" in the name of David Michael Goldstein et al., filed Nov. 15, 2013.
File History of U.S. Appl. No. 14/117,933, "Tyrosine Kinase Inhibitors" in the name of David Michael Goldstein, filed Nov. 15, 2013.
File History of U.S. Appl. No. 14/590,851, "Tyrosine Kinase Inhibitors" in the name of David Michael Goldstein, filed Jan. 6, 2015.
File History of U.S. Appl. No. 15/072,244, "Tyrosine Kinase Inhibitors" in the name of David Michael Goldstein, filed Mar. 16, 2016.
File History of U.S. Appl. No. 14/374,788, "Substituted Pyrazolo[3,4-d]Pyrimidines As Kinase Inhibitors," in the name of Tim Owens et al., filed Jul. 25, 2014.
File History of U.S. Appl. No. 14/464,602, "Pyrazolopyrimidine Compounds As Kinase Inhibitors," in the name of Tim Owens et al., filed Aug. 20, 2014.
File History of U.S. Appl. No. 14/997,330, "Pyrazolopyrimidine Compounds As Kinase Inhibitors," in the name of Tim Owens et al., filed Jan. 15, 2016.
File History of U.S. Appl. No. 14/084,519, "Purinone Derivatives As Tyrosine Kinase Inhibitors," in the name of Timothy D. Owens, filed Nov. 19, 2013.
File History of U.S. Appl. No. 14/997,248, "Purinone Derivatives As Tyrosine Kinase Inhibitors," in the name of Timothy D. Owens, filed Jan. 15, 2016.
2012 ICD-9-CM Diagnosis Code 372.30: Conjunctivitis, unspecified, retrieved Aug. 4, 2016 (1 page).
Abdulahad, W.H. et al. (2012), "Immune regulation and B-cell depletion therapy in patients with primary Sjögren's syndrome," *J. Autoimmun*, 39(1): 103-111 (2012).
American Cancer Society. Can Non-Hodgkin's Lymphoma Be Prevented? (2016) Web: <https://www.cancer.org/cancer/non-hodgkin-lymphoma/causes-risks— prevention/prevention.html> (3 pages).
Ansel, H.C. et al., "Pharmaceutical Dosage Forms and Drug Delivery Systems," Seventh Edition, Lippincott Williams & Wilkins, A Wolters Kluwer Company, Chapters 1-8, pp. 1-243 (1999).
Arora, A. & E.M. Scholar (2005), "Role of Tyrosine Kinase Inhibitors in Cancer Therapy," *J. Pharmacol. Exp. Ther.*, 315(3):971-979.
Bastin, R.J. et al. (2000), "Salt Selection and Optimisation Procedures for Pharmaceutical New Chemical Entities," Org. Process Res. Dev, 4:427-435.
Berge, S.M. et al. (1977), "Pharmaceutical Salts," *J. Pharm. Sci.*, 66:1-19.

(56) References Cited

OTHER PUBLICATIONS

Bradshaw, J. et al. (2015) "Prolonged and tunable residence time using reversible covalent kinase inhibitors," *Nat. Chem. Biol.*, 11:525-531 (with online methods) (10 pages).
Certified English Translation of CN 105753863 A, published in Chinese on Jul. 13, 2016 (57 pages).
Dias, A.L. & D. Jain (2013), "Ibrutinib: A New Frontier in the Treatment of Chronic Lymphocytic Leukemia by Bruton's Tyrosine Kinase Inhibition," *Cardiovasc Hematol Agents Med Chem*, 11(4):265-271.
Di Paolo, J.A. et al. (2011), "Specific Btk inhibition suppresses B cell—and myeloid cell-mediated arthritis," *Nat. Chem. Biol.*, 7:41-50.
Evans, E.K. et al. (2013), "Inhibition of Btk with CC-292 Provides Early Pharmacodynamic Assessment of Activity in Mice and Humans,"*J. Pharm. Exp. Ther.*, 346(2):219-28.
Ghoreschi, K. et al. (2009), "Janus kinases in immune cell signaling," *Immunol Rev.*, 228:273-287.
Grando, S.A. (2012), "Pemphigus autoimmunity: Hypotheses and realities," *Autoimmunity*, 45(1):7-35.
Hantschel, O. et al. (2007), "The Btk tyrosine kinase is a major target of the Bcr-Abl inhibitor dasatinib." *PNAS*, 104(33): 13283-13288.
Honigberg, L.A. et al. (2010), "The Bruton tyrosine kinase inhibitor PCI-32765 blocks B-cell activation and is efficacious in models of autoimmune disease and B-cell malignacy," *PNAS*, 107(29):13075-13080.
Johnson, M. & K.J. Corcoran, "Coding for Dry Eye," Optometric Management, Issue: Mar. 2004 (7 pages).
Kanwar, A.J. & K. Vinay (2012), "Rituximab in Pemphigus," *Indian J. Dermatol. Venereol. Leprol.* [serial online], 78:671-676, http://www.ijdvl.com/text.asp?2012/78/6/671/102354 (10 pages).
Leopold, C.S., "A Practical Approach in the Design of Colon-specific Drug Delivery System," Wiley-VCH; Drug Targeting Organ-Specific Strategies, Chapter 6, pp. 157-170 (2001).
MedicineNet.com. Definition of Cancer. (2004) Web: <http://www.medterms.com> (1 page).
MedlinePlus. Autoimmune Diseases (2014) Web: <https://www.nlm.nih.gov/medlineplus/autoimmunediseases.html> (5 pages).
Meydan, N. et al. (1996), "Inhibition of acute lymphoblastic leukaemia by a Jak-2 inhibitor," *Nature*, 379:645-648.
Nakamura, M. et al. (2012), "Diquafosol Ophthalmic Solution for Dry Eye Treatment," *Adv Ther*, 29(7):579-589.
Patani, G. & E. Lavoie (1996), "Bioisosterism: A Rational Approach in Drug Design," *Chem. Rev.*, 96:3147-3176.
Pennington, L.D. et al., "The Necessary Nitrogen Atom: A Versatile High-Impact Design Element for Multiparameter Optimization," *J. Med. Chem.*, ePub Feb. 8, 2017, 28 pages, DOI: 10.1021/acs.jmedchem.6b01807.
Rankin, A.L. et al. (2013), "Selective Inhibition of BTK Prevents Murine Lupus and Antibody-Mediated Glomerulonephritis," *J. Immunol.*, 191(9):4540-4550.
Robak, T. & E. Robak (2012), "Tyrosine kinase inhibitors as potential drugs for B-cell lymphoid malignancies and autoimmune disorders," *Expert Opin. Investig. Drugs*, 21(7):921-947.
Santus, G. & R.W. Baker (1995), "Osmotic Drug Delivery: A Review of the Patent Literature," *J. Control. Release*, 35:1-21.
Schwöbel, J. et al. (2010), "Prediction of Michael-Type Acceptor Reactivity toward Glutathione," *Chem. Res. Toxicol.*, 23, 1576-1585.
Stahl, P. Heirich & C.G. Wermuth (Eds.) (2002), Handbook of Pharmaceutical Salts: Properties, Selection, and Use, Wiley-VCH; pp. 1-374.
WebMD. 10 Ways to Prevent Psoriasis Flare-Ups. (2016) Web: <http://www.webmd.com/skin-problems-and-treatments/psoriasis/prevent-flare-ups> (8 pages).
WebMD. Multiple Sclerosis (MS)-Prevention. (2015) Web: < http://www.webmd.com/multiple-sclerosis/tc/multiple-sclerosis-ms-prevention> (4 pages).
WhatisDryEye.com. Dry Eye vs. Conjunctivitis (2016) Web: <http://www.whatisdryeye.com/dry-eye-vs-conjunctivitis> (5 pages).
Wilding, I.R. et al. (1994), "Targeting of Drugs and Vaccines to the Gut," *Pharmac. Ther.*, 62:97-124.
Wissner, A. et al. (2003), "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," *J. Med. Chem.*, 46:49-63.
Xu, D. et al. (2012), "RN486, a Selective Bruton's Tyrosine Kinase Inhibitor, Abrogates Immune Hypersensitivity Responses and Arthritis in Rodents," *J. Pharm. Exp. Ther.*, 341(1):90-103.
Communication Pursuant to Article 94(3) EPC for European Patent Application No. 13731218.7, dated Sep. 23, 2015 (4 pages).
Extended European Search Report for European Patent Application No. 17152898.7, dated Mar. 8, 2017 (7 pages).
International Search Report and Written Opinion dated Jul. 5, 2012, in International Patent Application No. PCT/US2012/038092, filed May 16, 2012, by Principia Biopharma Inc. (8 pages).
International Search Report and Written Opinion dated Aug. 20, 2012, in International Patent Application No. PCT/US2012/038120, filed May 16, 2012, by Principia Biopharma Inc. (10 pages).
International Search Report and Written Opinion dated Jul. 9, 2012, in International Patent Application No. PCT/US2012/038163, filed May 16, 2012, by Principia Biopharma Inc. (8 pages).
International Search Report and Written Opinion dated Sep. 3, 2013, in International Patent Application No. PCT/US2013/045266, filed Jun. 11, 2013, by Principia Biopharma Inc. (11 pages).
International Search Report and Written Opinion dated Oct. 1, 2013, in International Patent Application No. PCT/US2013/047958, filed Jun. 26, 2013, by Principia Biopharma Inc. (14 pages).
International Search Report and Written Opinion dated Nov. 18, 2013, in International Patent Application No. PCT/US2013/053042, filed Jul. 31, 2013, by Principia Biopharma Inc. (12 pages).
International Search Report and Written Opinion dated Apr. 22, 2015, in International Patent Application No. PCT/US2015/016963, filed Feb. 20, 2015, by Mohammad Reza Masjedizadeh et al. (10 pages).
International Search Report and Written Opinion dated Mar. 9, 2016, in International Patent Application No. PCT/US2015/066868, filed Dec. 18, 2015, by Steven Gourlay (13 pages).
International Search Report and Written Opinion dated Apr. 18, 2016, in International Patent Application No. PCT/US2015/000515, filed Dec. 23, 2015, by Philip A. Nunn et al. (11 pages).
International Search Report and Written Opinion dated Mar. 21, 2016, in International Patent Application No. PCT/US2015/000303, filed Dec. 23, 2015, by Philip Nunn et al. (12 pages).
International Search Report and Written Opinion dated Aug. 16, 2016, in International Patent Application No. PCT/US2016/035588, filed Jun. 2, 2016, by Principia Biopharma Inc. (10 pages).
International Search Report and Written Opinion dated Oct. 6, 2016, in International Patent Application No. PCT/US2016/039070, filed Jun. 23, 2016, by Principia Biopharma Inc. (18 pages).
International Search Report and Written Opinion dated Oct. 2, 2017, in International Patent Application No. PCT/US2017/040075, filed Jun. 29, 2017, by Principia Biopharma Inc. (9 pages).
U.S. Appl. No. 15/072,244, filed Mar. 16, 2016, by Principia Biopharma Inc.
U.S. Appl. No. 15/188,941, filed Jun. 21, 2016, by Principia Biopharma Inc.
U.S. Appl. No. 16/312,258, filed Dec. 20, 2018, by Principia Biopharma Inc.

SUBSTITUTED PYRAZOLO[3,4-D]PYRIMIDINES AS KINASE INHIBITORS

CROSS-REFERENCE TO RELATED APPLICATIONS

This application is a continuation of U.S. application Ser. No. 14/997,330, filed Jan. 15, 2016, which is continuation of U.S. application Ser. No. 14/374,788, now U.S. Pat. No. 9,266,895, filed Jul. 25, 2014, which is a national stage entry of International Application No. PCT/US2013/058614, filed Sep. 6, 2013, which claims the benefit of priority to U.S. Provisional Application No. 61/782,605, filed Mar. 14, 2013, U.S. Provisional Application No. 61/728,693, filed Nov. 20, 2012, and U.S. Provisional Application No. 61/699,038, filed Sep. 10, 2012, each of which is incorporated herein by reference in their entirety.

BACKGROUND OF THE INVENTION

Field of the Invention

The present disclosure provides certain small-molecule compounds that are tyrosine kinase inhibitors, in particular Bruton's tyrosine kinase (BTK) inhibitors, and are therefore useful for the treatment of diseases treatable by inhibition of tyrosine kinases such as cancer and inflammatory diseases. Also provided are certain pharmaceutical compositions containing such compounds and processes for preparing such compounds.

Description of Related Art

The human genome contains at least 500 genes encoding protein kinases. Many of these kinases have been implicated in human disease and as such represent potentially attractive therapeutic targets. BTK, a member of the Tec family non-receptor tyrosine kinases, is essential for B cell signaling downstream from the B-cell receptor. It is expressed in B cells and other hematopoietic cells such as monocytes, macrophages, and mast cells. BTK is reported to function in various aspects of B cell function that maintain the B cell repertoire (see Gauld S. B. et al., B cell antigen receptor signaling: roles in cell development and disease. *Science*, 296:1641-2. 2002)). Clinical validation of the role of B cells in RA has been provided by the efficacy of the biologic Rituxan (an anti-CD20 antibody), which depletes B cells as a mechanism of action (see Perosa F., et al., CD20-depleting therapy in autoimmune diseases: from basic research to the clinic. *J Intern Med.* 267:260-77. 2010 and Dörner T, et al. Targeting B cells in immune-mediated inflammatory disease: a comprehensive review of mechanisms of action and identification of biomarkers. *Pharmacol Ther.* 125:464-75. 2010). BTK is reported to be required for B cell development because patients with the disease X-linked agammaglobulinemia (see Rosen F. S., et al., The primary immunodeficiencies. *N Engl J Med.* 333:431-40. 1995) lack of antibodies in their bloodstream. Notably, small-molecule BTK inhibitors in pre-clinical development have been reported to be efficacious in collagen-induced arthritis (see Pan Z., et al., Discovery of selective irreversible inhibitors for Bruton's tyrosine kinase. *J. Med. Chem.* 2:58-61. 2007). The potential advantage of a small molecule BTK inhibitor (beyond the inherent advantage of a small-molecule over a biologic) is that modulation of BTK can inhibit B cell function without permanent removal of the B cell itself. Therefore, the long periods of low B cell levels experienced with the biologic Rituxan should be avoidable by targeting BTK with a small molecule BTK inhibitor.

In addition, the disease modifying activities of BTK are expected to extend beyond those of Rituxan because of effects on addition cellular targets that are involved in propagation of disease. For instance, antigen induced mast cell degranulation is reportedly impaired in mast cells derived from the bone marrow of BTK deficient mice, demonstrating that BTK is downstream of the FcεR1 receptor (see Setoguchi R., et al., Defective degranulation and calcium mobilization of bone-marrow derived mast cells from Xid and BTK-deficient mice. *Immunol Lett.* 64:109-18. 1998). A similar signaling module exists in monocytes and macrophages for the FcγR1 receptor indicating BTK inhibition is highly likely to modulate TNF production in response to IgG. Both mast cells and macrophages are thought to contribute to propagation of the inflammatory cytokine environment of the diseased synovium.

In addition to the peripheral and synovial effects of BTK inhibition described above, BTK inhibition reportedly will have bone protective effects in an inflamed joint (see Gravallese E. M., et al., Synovial tissue in rheumatoid arthritis is a source of osteoclast differentiation factor. *Arthritis Rheum.* 43:250-8. 2000). Studies with mice that are either deficient in BTK or have impaired BTK function have reportedly demonstrated that Rank ligand-induced osteoclast differentiation is impaired in the absence of BTK function (see Lee S. H., et. al., The tec family tyrosine kinase BTK Regulates RANKL-induced osteoclast maturation. *J. Biol. Chem.* 283:11526-34. 2008). Taken together, these studies can be interpreted as suggesting that a BTK inhibitor could inhibit or reverse the bone destruction that occurs in RA patients. Given the importance of B cells in autoimmune disease, BTK inhibitors could also have utility in other autoimmune diseases such as systemic lupus erythematosus (see Shlomchik M. J., et. al., The role of B cells in lpr/lpr-induced autoimmunity. *J. Exp Med.* 180:1295-1306. 1994). Notably, an irreversible BTK inhibitor has been reported to display efficacy in the mouse MRL.lpr lupus model, reducing autoantibody production and renal damage (see Honigberg L. A., The Bruton tyrosine kinase inhibitor PCI-32765 blocks B-cell activation and is efficacious in models of autoimmune disease and B-cell malignancy. *Proc. Natl. Acad. Sci.* 107:13075-80. 2010).

There is also potential for BTK inhibitors for treating allergic diseases (see Honigberg, L., et. al., The selective BTK inhibitor PCI-32765 blocks B cell and mast cell activation and prevents mouse collagen indiced arthritis. *Clin. Immunol.* 127 S1:S111. 2008). In addition, the irreversible inhibitor reportedly suppresses passive cutaneous anaphylaxis (PCA) induced by IgE antigen complex in mice (see Honigberg, L., et. al., The selective BTK inhibitor PCT-32765 blocks B cell and mast cell activation and prevents mouse collagen indiced arthritis. *Clin. Inununol.* 127 S1:S111. 2008). These reported findings are in agreement with those noted with BTK-mutant mast cells and knockout mice and can be interpreted as suggesting that BTK inhibitors may be useful for the treatment of asthma, an IgE-dependent allergic disease of the airway.

In addition, platelet aggregation in response to collagen or collagen-related peptide is reportedly impaired in XLA patients who lack BTK function (see Quek L. S, et al., A role for Bruton's tyrosine kinase (BTK) in platelet activation by collagen. *Curr. Biol.* 8:1137-40.1998). This is manifested by changes downstream from GPIV, such as phosphorylation of PLCgamma2 and calcium flux, which can be interpreted as suggesting potential utility in treating thrombocmbolic diseases.

Preclinical studies with a selective inhibitor of BTK have reportedly shown effects on spontaneous canine B cell lymphomas suggesting a potential utility in human lymphomas or other hematologic malignancies including chronic lymphocytic leukemia. In addition, clinical trials with PCI-32765 can be interpreted as indicating utility for a BTK inhibitor in both chronic lymphocytic leukemia and mantle cell lymphoma (see Fowler, N et al., The Btk inhibitor, PCI-32765, induces durable responses with minimal toxicity in patients with relapsed/refractory Bcell malignancies: results from a phase I study. *Blood* 2010; 116 (21):425; Byrd J. C., et al. Activity and tolerability of the Bruton's tyrosine kinase (Btk) inhibitor PCI-32765 in patients with chronic lymphocytic leukemia/small lymphocytic lymphoma (CLL/SLL): Interim results of a phase Ib/II study. *J Clin Oncol* 2011; 29:6508).

ITK, a member of the TEC kinase family, is reportedly involved in activation of T cells and mast cells (see Iyer A. S. et al., Absence of Tec Family Kinases Interleukin-2 Inducible T cell Kinase (Itk) and Bruton's Tyrosine Kinase (Btk) Severely Impairs Fc{epsilon}RI-dependent Mast Cell Responses. *J. Biol Chem.;* 286:9503-13. 2011) and is a potential target in inflammatory immune diseases such as asthma. Mice deficient in ITK are reportedly resistant to development of allergic asthma (see Sahu N, et al., Differential sensitivity to Itk kinase signals for T helper 2 cytokine production and chemokine-mediated migration. *J. Immunol.* 180:3833-8. 2008). Another family member, BMX, is reportedly involved in supporting tumor angiogenesis through it's role in the tumor vascular endothelium (see Tu T, et al., Bone marrow X kinase-mediated signal transduction in irradiated vascular endothelium. *Cancer Res.* 68:2861-9. 2008) and is also progressively up-regulated during bladder cancer progression (see Guo S., et al., Tyrosine Kinase ETK/BMX Is Up-Regulated in Bladder Cancer and Predicts Poor Prognosis in Patients with Cystectomy. *PLoS One.* 6:e17778. 2011), which can be interpreted to suggest a potential therapeutic target in this type cancer. The B lymphoid kinase (hereafter, sometimes expressed as "BLK") is reportedly linked through genetic association with a variety of rheumatic diseases including systemic lupus erythematosus and systemic sclerosis (see Ito I, et al., Association of the FAM167A-BLK region with systemic sclerosis. *Arthritis Rheum.* 62:890-5. 2010).

Accordingly, there is a need for compounds that inhibit tyrosine kinases, and particularly BTK inhibitors, thereby providing treatment for diseases such as autoimmune diseases, inflammatory diseases, thromboembolic diseases, and cancer. The present disclosure is directed to such treatment.

In an embodiment, provided is a compound of Formula (II):

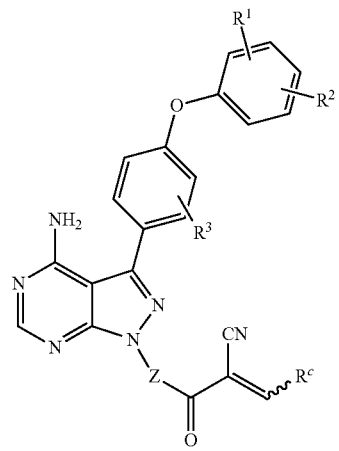

(II)

where:
—Z— is:

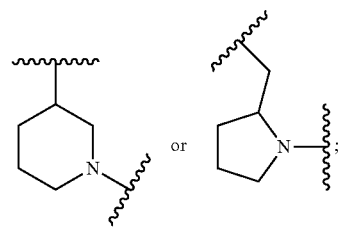 [SMILES: *C1CCCN(*)C1 ; *CC1CCCN1*]

$R^1$ and $R^2$ are independently hydrogen, alkyl, halo, or alkoxy;
$R^3$ is hydrogen or halo; and
$R^c$ is:
(a) —C(CH$_3$)$_2$-(4-R$^5$-piperazin-1-yl) where $R^5$ is hydrogen, alkyl, alkoxyalkyl, hydroxyalkyl, haloalkyl, alkylsulfonyl, alkoxycarbonyl, acyl, or oxetan-3-yl and the piperazinyl ring is additionally optionally substituted with one or two alkyl;
(b) —C(CH$_3$)$_2$-(2- or 3-oxo-4-R$^a$-piperazin-1-yl) where $R^a$ is hydrogen, alkyl, cycloalkyl, alkoxyalkyl, haloalkyl, or oxetan-3-yl and the piperazinyl ring is additionally optionally substituted with one or two alkyl;
(c) —C(CH$_3$)$_2$—NR$^b$oxetan-3-yl where $R^b$ is hydrogen, alkyl, hydroxyalkyl, alkoxyalkyl, or cycloalkyl;
(d) —C(CH$_3$)$_2$—R$^c$ where R$^c$ is

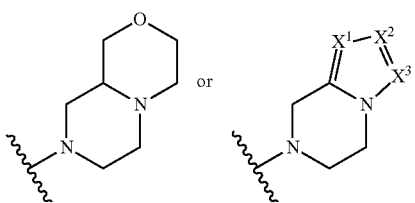

where one or two of $X^1$, $X^2$ and $X^3$ are nitrogen and the rest are carbon and the ring is optionally substituted with one or two substituents independently selected from alkyl, haloalkyl, or halo; or (e) —C(CH$_3$)$_2$-2-oxa-6-azaspiro[3.3]heptan-6-yl, or —C(CH$_3$)$_2$—CH$_2$morpholine-4-yl;

and/or a pharmaceutically acceptable salt thereof.

In one embodiment, the compound or salt thereof of Formula (II) is where R$^1$ is hydrogen, alkyl, halo, or alkoxy and R$^2$ is alkyl, halo, or alkoxy. Within this embodiment, in one group of compounds R$^3$ is fluoro.

In another embodiment, the compound or salt thereof of Formula (II) is where R$^1$ is hydrogen, alkyl, halo, or alkoxy and R$^2$ is alkyl, halo, or alkoxy and R$^c$ is —C(CH$_3$)$_2$-(4-R$^5$-piperazin-1-yl) where R$^5$ is hydrogen, alkyl, alkoxyalkyl, hydroxyalkyl, haloalkyl, alkylsulfonyl, alkoxycarbonyl, acyl, or oxetan-3-yl and the piperazinyl ring is additionally optionally substituted with one or two alkyl. Within this embodiment, in one group of compounds R$^3$ is fluoro.

In yet another embodiment, the compound or salt thereof of Formula (II) is where R$^1$ and R$^2$ are hydrogen and R$^c$ is —C(CH$_3$)$_2$-(4-R$^5$-piperazin-1-yl) where R$^5$ is hydrogen, alkyl, alkoxyalkyl, hydroxyalkyl, haloalkyl, alkylsulfonyl, alkoxycarbonyl, acyl, or oxetan-3-yl and the piperazinyl ring is additionally optionally substituted with one or two alkyl. Within this embodiment, in one group of compounds R$^3$ is fluoro. Within this embodiment, in another group of compounds R$^3$ is hydrogen and R$^c$ is —C(CH$_3$)$_2$-(4-R$^5$-piperazin-1-yl) where R$^5$ is hydrogen, alkyl, or oxetan-3-yl.

In another embodiment, provided is a compound of Formula (IA):

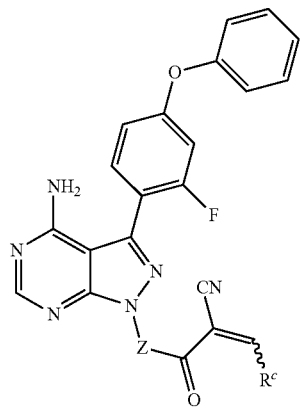

(IA)

where:
—Z— is:

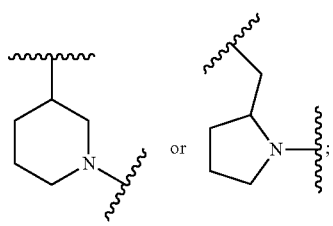 [SMILES: *C1CCCN(*)C1 ; *CC1CCCN1*]

and
R$^c$ is:
(a) —C(CH$_3$)$_2$-(4-R$^4$-piperazin-1-yl) where R$^4$ is hydrogen, alkyl, alkoxyalkyl, haloalkyl, alkylsulfonyl, alkoxycarbonyl, acyl, or oxetan-3-yl and the piperazinyl ring is additionally optionally substituted with one or two alkyl;

(b) —C(CH$_3$)$_2$-(3-oxo-4-R$^a$-piperazin-1-yl) where R$^a$ is hydrogen, alkyl, cycloalkyl, alkoxyalkyl, haloalkyl, or oxetan-3-yl and the piperazinyl ring is additionally optionally substituted with one or two alkyl;

(c) —C(CH$_3$)$_2$—NR$^b$oxetan-3-yl where R$^b$ is hydrogen, alkyl, alkoxyalkyl, or cycloalkyl;

(d) —C(CH$_3$)$_2$—R$^c$ where R$^c$ is

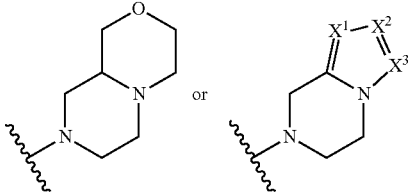

where one or two of X$^1$, X$^2$ and X$^3$ are nitrogen and the rest are carbon and the ring is optionally substituted with one or two substituents independently selected from alkyl, haloalkyl, or halo; or (e) —C(CH$_3$)$_2$-2-oxa-6-azaspiro[3.3]heptan-6-yl, or —C(CH$_3$)$_2$—CH$_2$morpholine-4-yl;

and/or a pharmaceutically acceptable salt thereof.

In one embodiment, the compound or salt thereof of Formula (IA) is where R$^c$ is —C(CH$_3$)$_2$-(piperazin-1-yl), —C(CH$_3$)$_2$-(4-methylpiperazin-1-yl), —C(CH$_3$)$_2$-(4-ethyl-piperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—N(cyclopropyl)-oxetan-3-yl, —C(CH$_3$)$_2$—NHoxetan-3-yl, —C(CH$_3$)$_2$-2-oxa-6-azaspiro-[3.3]heptan-6-yl, —C(CH$_3$)$_2$—CH$_2$morpholine-4-yl, —C(CH$_3$)$_2$-(4-methylsulfonyl-piperazin-1-yl), —C(CH$_3$)$_2$-(3-oxo-4-methylpiperazin-1-yl), —C(CH$_3$)$_2$-[4-(2-methoxyethyl)-piperazin-1-yl], —C(CH$_3$)$_2$-(4-tert-butylpiperazin-1-yl), —C(CH$_3$)$_2$-(4-acetylpiperazin-1-yl), —C(CH$_3$)$_2$-(4-2,2,2-trifluoroethyl-piperazin-1-yl), —C(CH$_3$)$_2$-(4-isopropylpiperazin-1-yl), —C(CH$_3$)$_2$-(2,5-dimethyl-piperazin-1-yl), —C(CH$_3$)$_2$-(3,5-dimethylpiperazin-1-yl), —C(CH$_3$)$_2$-(3,4,5-trimethylpiperazin-1-yl), —C(CH$_3$)$_2$-(2,4,5-trimethylpiperazin-1-yl), —C(CH$_3$)$_2$-(4-oxetan-3-ylpiperazin-1-yl), —C(CH$_3$)$_2$-(4-methoxycarbonylpiperazin-1-yl), —C(CH$_3$)$_2$-(3,5-dimethylpiperazin-1-yl),

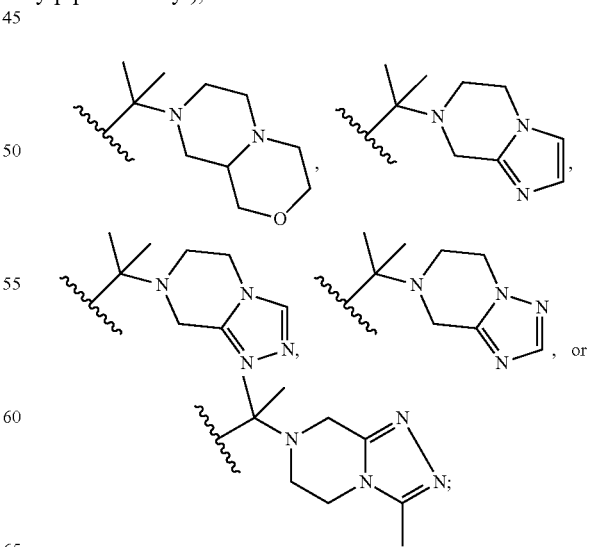

and/or a pharmaceutically acceptable salt thereof.

In another embodiment, the compound or salt thereof of Formula (IA) is where $R^c$ is —C(CH$_3$)$_2$-(piperazin-1-yl), —C(CH$_3$)$_2$-(4-methylpiperazin-1-yl), —C(CH$_3$)$_2$-(4-ethyl-piperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—N(cyclopropyl)-oxetan-3-yl, or —C(CH$_3$)$_2$—NHoxetan-3-yl.

In yet another embodiment, the compound or salt thereof of Formula (IA) is where $R^c$ is —C(CH$_3$)$_2$-(3-oxo-4-methylpiperazin-1-yl), —C(CH$_3$)$_2$-[4-(2-methoxyethyl)-piperazin-1-yl], —C(CH$_3$)$_2$-(4-tert-butylpiperazin-1-yl), —C(CH$_1$)$_2$-(4-isopropylpiperazin-1-yl), —C(CH$_3$)$_2$-(2,5-dimethyl-piperazin-1-yl), —C(CH$_3$)$_2$-(3,5-dimethylpiperazin-1-yl), —C(CH$_3$)$_2$-(3,4,5-trimethylpiperazin-1l-yl), —C(CH$_3$)$_2$-(2,4,5-trimethylpiperazin-1-yl), —C(CH$_3$)$_2$-(4-oxetan-3-ylpiperazin-1-yl), —C(CH$_3$)$_2$-(4-methoxycarbonylpiperazin-1-yl), —C(CH$_3$)$_2$-(3,5-dimethylpiperazin-1-yl), or

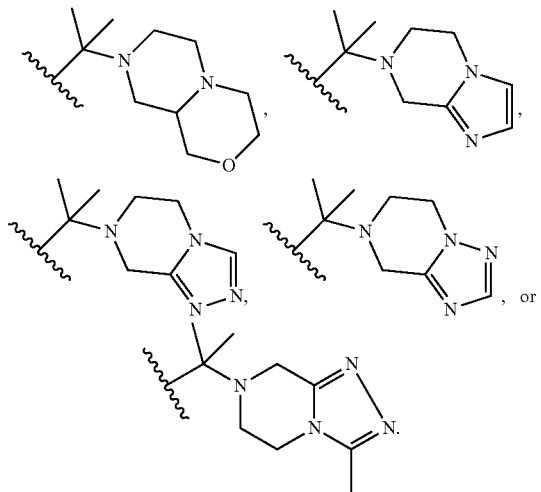

In yet another embodiment, the compound or salt thereof of Formula (IA) is where $R^c$ is —C(CH$_3$)$_2$-(3-oxo-4-methylpiperazin-1-yl) or —C(CH$_3$)$_2$-[4-(2-methoxyethyl)-piperazin-1-yl].

In yet another embodiment, the compound of Formula (IA) is chosen from:
2-[(2S)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile;
2-[(2R)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile;
2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile;
2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile;
2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile;
2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile;
2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile;
2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile;
2-[(3R)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile;
2-[(3S)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile;
2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile;
2-[[(3S)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile;
2-((R)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile;
2-((S)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-methyl-4-(ethyl(oxetan-3-yl)amino)pent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methyl-4-(ethyl(oxetan-3-yl)amino)pent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-methyl-4-(2-oxa-6-azaspiro[3.3]heptan-6-yl)pent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methyl-4-(2-oxa-6-azaspiro[3.3]heptan-6-yl)pent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(2-oxa-6-azaspiro[3.3]heptan-6-yl)pent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(2-oxa-6-azaspiro[3.3]heptan-6-yl)pent-2-enenitrile;
2-[(2S)-2-[[4-amino-3-(2-fluoro-4-phenoxyphenyl)pyrazolo[34-d]pyrimidin-1-yl]-methyl]pyrrolidine-1-carbonyl]-4-methyl-4-(4-ethylpiperazin-1-yl)pent-2-enenitrile;
2-[(2R)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-ethylpiperazin-1-yl)pent-2-enenitrile;
2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile;

2-[[(3S)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(oxetan-3-yl)aminopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(oxetan-3-yl)animopent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(cyclopropyl(oxetan-3-yl)amino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(cyclopropyl(oxetan-3-yl)amino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(4-isopropylpiperazin-1-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(4-isopropylpiperazin-1-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(4-(tert-butyl)piperazin-1-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(4-(tert-butyl)piperazin-1-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(4-(2-methoxyethyl)piperazin-1-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(4-(2-methoxyethyl)piperazin-1-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((R)-hexahydropyrazino[2,1-c][1,4]oxazin-8(1H)-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((R)-hexahydropyrazino[2,1-c][1,4]oxazin-8(1H)-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((S)-hexahydropyrazino[2,1-c][1,4]oxazin-8(1H)-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((S)-hexahydropyrazino[2,1-c][1,4]oxazin-8(1H)-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(2,2,2-trifluoroethyl)piperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(2,2,2-trifluoroethyl)piperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-((3S,5R)-3,4,5-trimethylpiperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-((3S,5R)-3,4,5-trimethylpiperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((3S,5R)-3,5-dimethylpiperazin-1-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((3S,5R)-3,5-dimethylpiperazin-1-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((2R,5S)-2,5-dimethylpiperazin-1-yl)-4-methylpent-2-enenitrile;

2-((S)-3-(4-amino-3-(2-fluoro-4-phenoxyphenyl)-1-pyrazolo[3,4-d]pyrimidin-1-yl)piperidine-1-carbonyl)-4-((2R,5S)-2,5-dimethylpiperazin-1-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-((2R,5S)-2,4,5-ti methylpiperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-((2R,5S)-2,4,5-trimethylpiperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((2S,5R)-2,5-dimethylpiperazin-1-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((2S,5R)-2,5-dimethylpiperazin-1-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-((2S,5R)-2,4,5-trimethylpiperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-((2S,5R)-2,4,5-trimethylpiperazin-1-yl)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(5,6-dihydroimidazo[1,2-a]pyrazin-7(8H)-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(5,6-dihydroimidazo[1,2-a]pyrazin-7(8H)-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(methylsulfonyl)piperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(methylsulfonyl)piperazin-1-yl)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-methyl-3-oxopiperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-methyl-3-oxopiperazin-1-yl)pent-2-enenitrile;

(R)-4-(4-acetylpiperazin-1-yl)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(S)-4-(4-acetylpiperazin-1-yl)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(R)-methyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate;

(S)-methyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate;

(R)-2-(3-(4-amino-3-(2-fluoro-4-phenoxyphenyl)-1H-pyrazolo[3,4-d]pyrimidin-1-yl)piperidine-1-carbonyl)-4,4-dimethyl-5-morpholinopent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4,4-dimethyl-5-morpholinopent-2-enenitrile;

or a mixture of R and S isomers thereof;

or an individual E or Z isomer of any of the above compounds; and/or a pharmaceutically acceptable salt of any of the above compounds.

In another embodiment, provided is a compound of Formula (I):

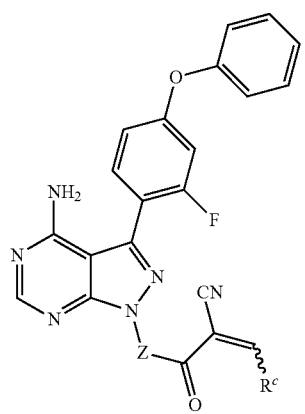

(I)

where:
—Z— is:

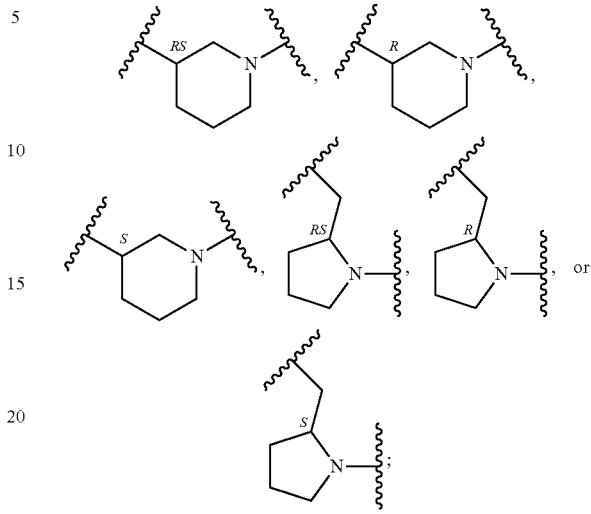

$R^c$ is —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—N(cyclopropyl)oxetan-3-yl, —C(CH$_3$)$_2$—NHoxetan-3-yl, or —C(CH$_3$)$_2$-2-oxa-6-azaspiro[3.3]heptan-6-yl;

and/or a pharmaceutically acceptable salt thereof.

In one embodiment, the compound of Formula (I) is chosen from:

2-[(2RS)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile;

2-[(2S)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile;

2-[(2R)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile;

2-[(2RS)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile;

2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile;

2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile;

2-[(2RS)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile;

2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile;

2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile;

2-[(2RS)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile;

2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile;

2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile;

2-[(3RS)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile;

2-[(3R)-3-[4-amino-3-(2-fluoro-4-phenoxy-phenyl)pyrazolo[3,4-d]pyrimidin-1-yl]piperidine-1-carbonyl]-4-methyl-[methyl(oxetan-3-yl)amino]pent-2-enenitrile;

2-[(3S)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile;

2-[[(3RS)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile;

2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile;

2-[[(3S)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile;

2-((RS)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile;

(RS)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrolidine-1-carbonyl)-4-(ethyl(oxetan-3-yl)amino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile;

(RS)-2-(3-(4-amino-3-(2-fluoro-4-phenoxyphenyl)-1H-pyrazolo[3,4-d]pyrimidin-1-yl)piperidine-1-carbonyl)-4-methyl-4-(ethyl(oxetan-3-yl)amino)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(ethyl(oxetan-3-yl)amino)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(ethyl(oxetan-3-yl)amino)pent-2-enenitrile;

(RS)-2-(3-(4-amino-3-(2-fluoro-4-phenoxyphenyl)-1H-pyrazolo[3,4-d]pyrimidin-1-yl)piperidine-1-carbonyl)-4-methyl-4-(2-oxa-6-azaspiro[3.3]heptan-6-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(2-oxa-6-azaspiro[3.3]heptan-6-yl)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(2-oxa-6-azaspiro[3.3]heptan-6-yl)pent-2-enenitrile;

(RS)-2-(2-((4-amino-3-(2-fluoro-4-phenoxyphenyl)-1H-pyrazolo[3,4-d]pyrimidine-1-yl)methyl)pyrrolidine-1-carbonyl)-4-methyl-4-(2-oxa-6-azaspiro[3.3]heptan-6-yl)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(2-oxa-6-azaspiro[3.3]heptan-6-yl)pent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(2-oxa-6-azaspiro[3.3]heptan-6-yl)pent-2-enenitrile;

2-[(2RS)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-ethylpiperazin-1-yl)pent-2-enenitrile;

2-[(2S)-2-[[4-amino-3-(2-fluoro-4-phenoxyphenyl)pyrazolo[3,4-d]pyrimidin-1-yl]-methyl]pyrrolidine-1-carbonyl]4-methyl-4-(4-ethylpiperazin-1-yl)pent-2-enenitrile;

2-[(2R)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-ethylpiperazin-1-yl)pent-2-enenitrile;

2-[[(3RS)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile;

2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile;

2-[[(3S)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile;

(RS)-2-(3-(4-amino-3-(2-fluoro-4-phenoxyphenyl)-1H-pyrazolo[3,4-d]pyrimidin-1-yl)piperidine-1-carbonyl)-4-methyl-4-(oxetan-3-yl)aminopent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(oxetan-3-yl)aminopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(oxetan-3-yl)aminopent-2-enenitrile;

(RS)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile;

(RS)-2-(3-(4-amino-3-(2-fluoro-4-phenoxyphenyl)-1H-pyrazolo[3,4-d]pyrimidin-1-yl)piperidine-1-carbonyl)-4-(cyclopropyl(oxetan-3-yl)amino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(cyclopropyl(oxetan-3-yl)amino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(cyclopropyl(oxetan-3-yl)amino)-4-methylpent-2-enenitrile;
or an individual E or Z isomer of any of the above compounds; and/or a pharmaceutically acceptable salt of any of the above compounds.

In yet another embodiment, provided is a compound of Formula (IB):

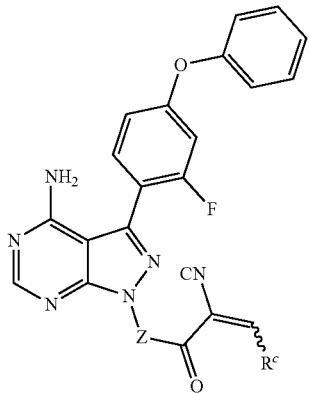

(IB)

where:
—Z— is:

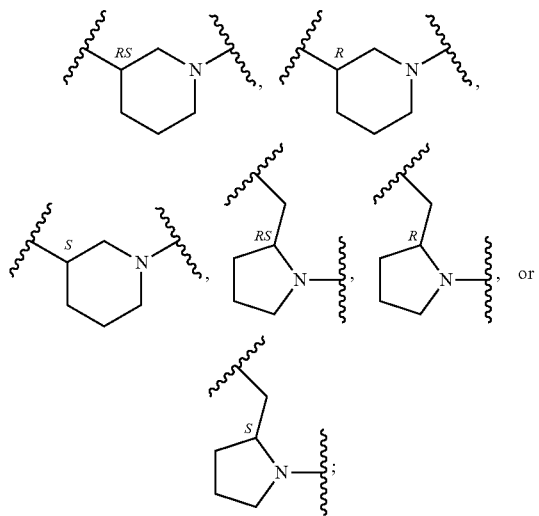

$R^c$ is 3-methyloxetan-3-yl, —C(CH$_3$)$_2$-(azetidin-1-yl), —C(CH$_3$)$_2$-(3-hydroxyazetidine-1-yl), —C(CH$_3$)$_2$-(4-hydroxypiperidin-1-yl), —C(CH$_3$)$_2$-(pyrrolidin-1-yl), or —C(CH$_3$)$_2$CH$_2$OH; and/or a pharmaceutically acceptable salt thereof;
provided that when Z is

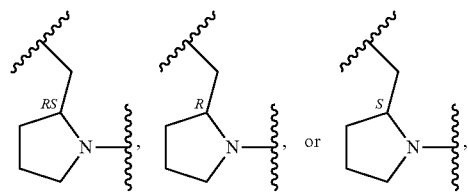

then $R^c$ is not 3-methyloxetan-3-yl, and/or a pharmaceutically acceptable salt thereof.

In one embodiment, the compound of Formula (IB) is chosen from:
(RS)-2-(3-(4-amino-3-(2-fluoro-4-phenoxyphenyl)-1H-pyrazolo[3,4-d]pyrimidin-1-yl)piperidine-1-carbonyl)-4-(4-hydroxypiperidin-1-yl)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(4-hydroxypiperidin-1-yl)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(4-hydroxypiperidin-1-yl)-4-methylpent-2-enenitrile;
2-((RS)-3-(4-amino-3-(2-fluoro-4-phenoxyphenyl)-1H-pyrazolo[3,4-d]pyrimidin-1-yl)piperidine-1-carbonyl)-4-(azetidin-1-yl)-4-methylpent-2-enenitrile;
2-((R)-3-(4-amino-3-(2-fluoro-4-phenoxyphenyl)-1H-pyrazolo[3,4-d]pyrimidin-1-yl) piperidine-1-carbonyl)-4-(azetidin-1-yl)-4-methylpent-2-enenitrile;
2-((S)-3-(4-amino-3-(2-fluoro-4-phenoxyphenyl)-1H-pyrazolo[3,4-d]pyrimidin-1-yl) piperidine-1-carbonyl)-4-(azetidin-1-yl)-4-methylpent-2-enenitrile;
(RS)-2-(3-(4-amino-3-(2-fluoro-4-phenoxyphenyl)-1H-pyrazolo[3,4-d]pyrimidin-1-yl)piperidine-1-carbonyl)-5-hydroxy-4,4-dimethylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-5-hydroxy-4,4-dimethylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-5-hydroxy-4,4-dimethylpent-2-enenitrile;
2-((RS)-3-(4-amino-3-(2-fluoro-4-phenoxyphenyl)-1H-pyrazolo[3,4-d]pyrimidin-1-yl)piperidine-1-carbonyl)-3-(3-methyloxetan-3-yl)acrylonitrile;
2-((R)-3-(4-amino-3-(2-fluoro-4-phenoxyphenyl)-1H-pyrazolo[3,4-d]pyrimidin-1-yl)piperidine-1-carbonyl)-3-(3-methyloxetan-3-yl)acrylonitrile;
2-((S)-3-(4-amino-3-(2-fluoro-4-phenoxyphenyl)-1H-pyrazolo[3,4-d]pyrimidin-1-yl)piperidine-1-carbonyl)-3-(3-methyloxetan-3-yl)acrylonitrile;
(RS)-2-(2-((4-amino-3-(2-fluoro-4-phenoxyphenyl)-1H-pyrazolo[3,4-d]-pyrimidin-1-yl)methyl)pyrrolidine-1-carbonyl)-4-methyl-4-(pyrrolidin-1-yl)pent-2-enenitrile;
(S)-2-(2-((4-amino-3-(2-fluoro-4-phenoxyphenyl)-1H-pyrazolo[3,4-d]-pyrimidin-1-yl)methyl)pyrrolidine-1-carbonyl)-4-methyl-4-(pyrrolidin-1-yl)pent-2-enenitrile;
(R)-2-(2-((4-amino-3-(2-fluoro-4-phenoxyphenyl)-1H-pyrazolo[3,4-d]-pyrimidin-1-yl)methyl)pyrrolidine-1-carbonyl)-4-methyl-4-(pyrrolidin-1-yl)pent-2-enenitrile;
2-((RS)-3-(4-amino-3-(2-fluoro-4-phenoxyphenyl)-1H-pyrazolo[3,4-d]pyrimidin-1-yl)piperidine-1-carbonyl)-4-(3-hydroxyazetidine-1-yl)-4-methylpent-2-enenitrile;
2-((R)-3-(4-amino-3-(2-fluoro-4-phenoxyphenyl)-1H-pyrazolo[3,4-d]pyrimidin-1-yl)piperidine-1-carbonyl)-4-(3-hydroxyazetidin-1-yl)-4-methylpent-2-enenitrile;
2-((S)-3-(4-amino-3-(2-fluoro-4-phenoxyphenyl)-1H-pyrazolo[3,4-d]pyrimidin-1-yl)piperidine-1-carbonyl)-4-(3-hydroxyazetidin-1-yl)-4-methylpent-2-enenitrile;
(RS)-2-(2-((4-amino-3-(2-fluoro-4-phenoxyphenyl)-1H-pyrazolo[3,4-d]pyrimidin-1-yl)methyl)pyrrolidine-1-carbonyl)-4-(3-hydroxyazetidin-1-yl)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(3-hydroxyazetidin-1-yl)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(3-hydroxyazetidin-1-yl)-4-methylpent-2-enenitrile; or an individual E or Z isomer of any of the above compounds; and/or a pharmaceutically acceptable salt of any of the above compounds.

In yet another embodiment, provided is a compound chosen from:
(RS)-2-[2-[[4-amino-3-(2-fluoro-4-phenoxy-phenyl)pyrazolo[3,4-d]pyrimidin-1-yl]methyl]azetidine-1-carbonyl]-4-methyl-pent-2-enenitrile;
(R)-2-[2-[[4-amino-3-(2-fluoro-4-phenoxy-phenyl)pyrazolo[3,4-d]pyrimidin-1-yl]methyl]azetidine-1-carbonyl]-4-methyl-pent-2-enenitrile;
(S)-2-[2-[[4-amino-3-(2-fluoro-4-phenoxy-phenyl)pyrazolo[3,4-d]pyrimidin-1-yl]methyl]azetidine-1-carbonyl]-4-methyl-pent-2-enenitrile;
2-[3-[[4-amino-3-(2-fluoro-4-phenoxy-phenyl)pyrazolo[3,4-d]pyrimidin-1-yl]methyl]azetidine-1-carbonyl]-4-methyl-pent-2-enenitrile;
(RS)-2-[2-[[4-amino-3-(2-fluoro-4-phenoxy-phenyl)pyrazolo[3,4-d]pyrimidin-1-yl]methyl]azetidine-1-carbonyl]-4-methyl-4-morpholino-pent-2-enenitrile;
(R)-2-[2-[[4-amino-3-(2-fluoro-4-phenoxy-phenyl)pyrazolo[3,4-d]pyrimidin-1-yl]methyl]azetidine-1-carbonyl]-4-methyl-4-morpholino-pent-2-enenitrile;
(S)-2-[2-[[4-amino-3-(2-fluoro-4-phenoxy-phenyl)pyrazolo[3,4-d]pyrimidin-1-yl]methyl]azetidine-1-carbonyl]-4-methyl-4-morpholino-pent-2-enenitrile;
(RS)-2-[2-[[4-amino-3-(2-fluoro-4-phenoxy-phenyl)pyrazolo[3,4-d]pyrimidin-1-yl]methyl]azetidine-1-carbonyl]-4-methyl-4-(4-methylpiperazin-1-yl)pent-2-enenitrile;
(R)-2-[2-[[4-amino-3-(2-fluoro-4-phenoxy-phenyl)pyrazolo[3,4-d]pyrimidin-1-yl]methyl]azetidine-1-carbonyl]-4-methyl-4-(4-methylpiperazin-1-yl)pent-2-enenitrile;
(S)-2-[2-[[4-amino-3-(2-fluoro-4-phenoxy-phenyl)pyrazolo[3,4-d]pyrimidin-1-yl]methyl]azetidine-1-carbonyl]-4-methyl-4-(4-methylpiperazin-1-yl)pent-2-enenitrile;
2-[3-[4-amino-3-(2-fluoro-4-phenoxy-phenyl)pyrazolo[3,4-d]pyrimidin-1-yl]-azetidine-1-carbonyl]-4-methyl-pent-2-enenitrile; or an individual E or Z isomer of any of the above compounds; and/or a pharmaceutically acceptable salt of any of the above compounds.

In yet another embodiment, the compound or a pharmaceutical acceptable salt is:
(R)-2-(3-(4-amino-3-(2-fluoro-4-(3-hydroxyphenoxy)phenyl)-1H-pyrazolo[3,4-d]pyrimidin-1-yl)piperidine-1-carbonyl)-4,4-dimethylpent-2-enenitrile;
(R)-2-(3-(4-amino-3-(2-fluoro-4-(4-hydroxyphenoxy)phenyl)-1H-pyrazolo[3,4-d]pyrimidin-1-yl)piperidine-1-carbonyl)-4,4-dimethylpent-2-enenitrile; or an individual E or Z isomer thereof.

In another embodiment, the compound is chosen from 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile, or an individual E or Z isomer thereof; and/or a pharmaceutically acceptable salt of any of the foregoing compounds.

In another embodiment, the compound is chosen from 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-[ethyl(oxetan-3-yl)amino]pent-2-enenitrile, or an individual E or Z isomer thereof; and/or a pharmaceutically acceptable salt of any of the foregoing compounds.

In another embodiment, the compound is chosen from 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile, or an individual E or Z isomer thereof; and/or a pharmaceutically acceptable salt of any of the foregoing compounds.

In another embodiment, the compound is chosen from 2-[(3R)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile, or an individual E or Z isomer thereof; and/or a pharmaceutically acceptable salt of any of the foregoing compounds.

In another embodiment, the compound is chosen from 2-[(3R)-3-[4-amino-3-(2-fluoro-4-phenoxy-phenyl)pyrazolo[3,4-d]pyrimidin-1-yl]piperidine-1-carbonyl]-4-methyl-4-[ethyl(oxetan-3-yl)amino]pent-2-enenitrile, or an individual E or Z isomer thereof; and/or a pharmaceutically acceptable salt of any of the foregoing compounds.

In another embodiment, the compound is chosen from 2-[(3R)-3-[4-amino-3-(2-fluoro-4-phenoxy-phenyl)pyrazolo[3,4-d]pyrimidin-1-yl]piperidine-1-carbonyl]-4-methyl-4-(oxetan-3-yl)aminopent-2-enenitrile, or an individual E or Z isomer thereof; and/or a pharmaceutically acceptable salt of any of the foregoing compounds.

In another embodiment, the compound is chosen from 2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile, or an individual E or Z isomer thereof; and/or a pharmaceutically acceptable salt of any of the foregoing compounds.

In another embodiment, the compound is chosen from 2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile, or an individual E or Z isomer thereof; and/or a pharmaceutically acceptable salt of any of the foregoing compounds.

In another embodiment, the compound is chosen from 2-((R)-3-(4-amino-3-(2-fluoro-4-phenoxy-phenyl)-1H-pyrazolo[3,4-d]pyrimidin-1-yl)piperidine-1-carbonyl)-4-(3-hydroxyazetidin-1-yl)-4-methylpent-2-enenitrile, or an individual E or Z isomer thereof; and/or a pharmaceutically acceptable salt of any of the foregoing compounds.

In another embodiment, the compound is chosen from (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-methyl-3-oxopiperazin-1-yl)pent-2-enenitrile; or an individual E or Z isomer thereof; and/or a pharmaceutically acceptable salt of any of the foregoing compounds.

In another embodiment, the compound is chosen from (R)-2-(3-(4-amino-3-(2-fluoro-4-phenoxyphenyl)-1H-pyrazolo[3,4-d]pyrimidin-1-yl)piperidine-1-carbonyl)-4-(4-(2-methoxyethyl)piperazin-1-yl)-4-methylpent-2-enenitrile; or an individual E or Z isomer thereof; and/or a pharmaceutically acceptable salt of any of the foregoing compounds.

In another embodiment, the compound is chosen from 2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(piperazin-1-yl)pent-2-enenitrile, or an individual E or Z isomer thereof; and/or a pharmaceutically acceptable salt of any of the foregoing compounds.

In another embodiment, the compound is chosen from (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile; or an individual E or Z isomer thereof; and/or a pharmaceutically acceptable salt of any of the foregoing compounds.

In another embodiment, the compound is chosen from (S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile; or an individual E or Z isomer thereof; and/or a pharmaceutically acceptable salt of any of the foregoing compounds.

In another embodiment, the compound is chosen from (R)-2-(3-(4-amino-3-(4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile; or an individual E or Z isomer thereof; and/or a pharmaceutically acceptable salt of any of the foregoing compounds.

In another embodiment, the compound is chosen from (S)-2-(3-(4-amino-3-(4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile; or an individual E or Z isomer thereof; and/or a pharmaceutically acceptable salt of any of the foregoing compounds.

In another embodiment, the compound is chosen from (R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(4-(oxetan-3-yl)piperazin-1-yl)pent-2-enenitrile; or an individual E or Z isomer thereof; and/or a pharmaceutically acceptable salt of any of the foregoing compounds.

In another embodiment, the compound is chosen from (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(4-(oxetan-3-yl)piperazin-1-yl)pent-2-enenitrile; or an individual E or Z isomer thereof; and/or a pharmaceutically acceptable salt of any of the foregoing compounds.

In one embodiment, the compounds of the present disclosure are reversible covalent inhibitors.

In another embodiment, the compounds of the present disclosure form a reversible covalent bond to Cys 481 of BTK.

Another embodiment disclosed herein is a pharmaceutical composition comprising a compound and/or a pharmaceutically salt of any embodiment disclosed herein and a pharmaceutically acceptable excipient.

Another embodiment disclosed herein is a method of treating a disease treatable by inhibition of a tyrosine kinase such as BLK, BMX, HER2, HER4, ITK, TEC, BTK, and TXK, such as BTK, in a patient in need of such treatment which method comprises administering to the patient in recognized need thereof, a pharmaceutical composition comprising a compound and/or a pharmaceutically acceptable salt of any embodiment disclosed herein and a pharmaceutically acceptable excipient in an amount effective to achieve the treatment (therapeutic amount). In one embodiment, the patient is in recognized need of such treatment. In one embodiment, the disease is chosen from autoimmune diseases, inflammatory diseases, and cancers.

In one aspect of above embodiment, the patient in need or recognized need is suffering from an autoimmune disease, e.g., inflammatory bowel disease, such as ulcerative colitis, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, Sjogren's dry eye, non-Sjogren's dry eye disease, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, and vulvodynia. In one embodiment, the disease is rheumatoid arthritis or psoriatic arthritis. In another embodiment, the autoimmune disease is lupus.

In yet another embodiment disclosed herein, the patient in need or recognized need is suffering from a heteroimmune condition or disease, e.g., graft versus host disease, transplantation, transfusion, anaphylaxis, allergy, type I hypersensitivity, allergic conjunctivitis, allergic rhinitis, and atopic dermatitis.

In yet another embodiment disclosed herein, the patient in need or recognized need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fascitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis, such as asthma. In yet another embodiment disclosed herein, the patient in need or recognized need is suffering from inflammatory skin disease, such as dermatitis, contact dermatitis, eczema, urticaria, rosacea, and scarring psoriatic lesions in the skin, joints, or other tissues or organs.

In yet another embodiment disclosed herein, the patient in need or recognized need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-ALL, B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In yet another embodiment, the patient in need or recognized need is suffering from a thromboembolic disorder, e.g., myocardial infarction, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

The disclosure is also directed to the use of any compound and/or a pharmaceutical salt thereof disclosed herein as a medicament. In one embodiment, the use of any of the compounds and/or a pharmaceutically acceptable salt thereof disclosed herein is for treating a disease mediated by a kinase, in particular BTK, for treating a disease chosen from autoimmune and inflammatory diseases and proliferative diseases, such as cancers.

The disclosure is also directed to the use of any compound and/or a pharmaceutically acceptable salt thereof in the manufacture of a medicament for treating an inflammatory disease in a patient in need of such treatment in which the activity of a tyrosine kinase, such as BLK, BMX, HER2, HER4, ITK, TEC, BTK, and TXK, in particular BTK, contributes to the pathology and/or symptoms of the disease. In one embodiment, the patient is in recognized need of such treatment. In one embodiment the disease is an autoimmune or inflammatory disease (e.g., arthritis, asthma) or a proliferative disease e.g., B-cell proliferative disorder, e.g., diffuse large B cell lymphoma, follicular lymphoma, chronic lymphocytic lymphoma, chronic lymphocytic leukemia, B-ALL, B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In any of the aforementioned embodiments disclosed herein involving the treatment of proliferative disorders, including cancer, combination therapy can also be implicated, i.e., the compounds and/or a pharmaceutically acceptable salt disclosed herein can be administered in combination with at least one additional antiproliferative and/or anticancer agent. In one embodiment, the at least additional agent is chosen from alemtuzumab, arsenic trioxide, asparaginase (pegylated or non-), bevacizumab, cetuximab, platinum-based compounds, such as cisplatin, cladribine, daunorubicin/doxorubicin/idarubicin, irinotecan, fludarabine, 5-fluorouracil, gemtuzamab, methotrexate, paclitaxel, Taxol™, docetaxol, temozolomide, thioguanine, and classes of drugs including hormones (an antiestrogen, an antiandrogen, or gonadotropin releasing hormone analogues, interferons such as alpha interferon, nitrogen mustards such as busulfan or melphalan or mcchlorethamine, retinoids such as tretinoin, topoisomerase inhibitors such as irinotecan or topotecan, tyrosine kinase inhibitors such as gefinitinib or imatinib, ofatumumab, bendamustine, rituximab, obinutuzumab, IPI-145, GS-1101, BKM-120, GDC-0941, DGDC-0980, GS-9820, CAL-263, Revlimid®, Thalidomide®, Pomalidomide®, Velcade®, Kyprolis®, delanzomib, U0126, PD98059, PD184352, PD0325901, ARRY-142886, SB239063, SP600125, BAY 43-9006, wortmannin, Nexavar®, Tarceva®, Sutent®, Tykerb@, Sprycel®, Crizotinib, Xalkori®, or LY294002 or agents to treat signs or symptoms induced by such therapy including allopurinol, filgrastim, granisetron/ondansetron/palonosetron, dronabinol. When combination therapy is used, the agents can be administered simultaneously or sequentially.

Also disclosed herein is a process of preparing a compound of Formula (IA):

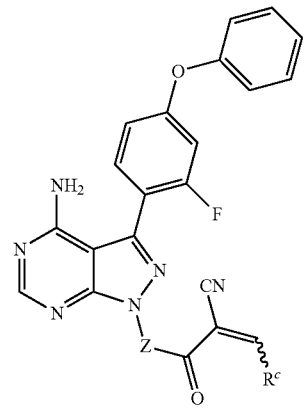

(IA)

where:
—Z— is:

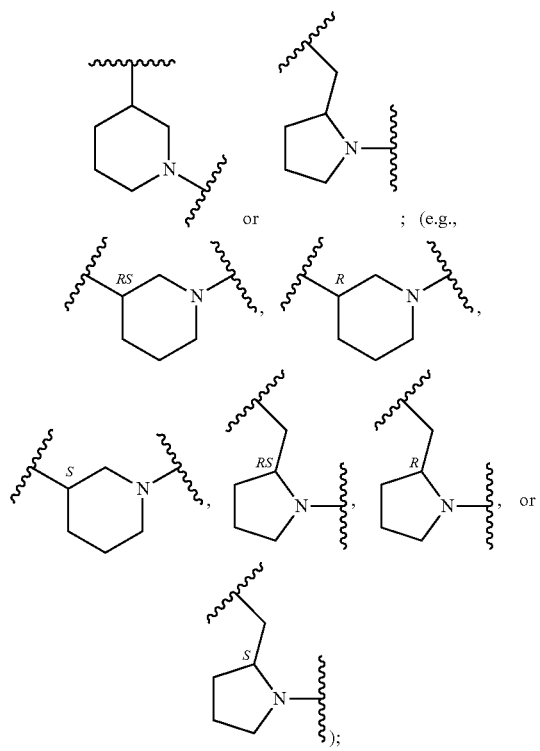

and
$R^c$ is:
(a) —C(CH$_3$)$_2$-(4-R$^4$-piperazin-1-yl) where $R^4$ is hydrogen, alkyl, alkoxyalkyl, haloalkyl, alkylsulfonyl, alkoxycarbonyl, acyl, or oxetan-3-yl and the piperazinyl ring is additionally optionally substituted with one or two alkyl;
(b) —C(CH$_3$)$_2$-(3-oxo-4-R$^a$-piperazin-1-yl) where $R^a$ is hydrogen, alkyl, alkoxyalkyl, haloalkyl, or oxetan-3-yl and the piperazinyl ring is additionally optionally substituted with one or two alkyl;
(c) —C(CH$_3$)$_2$—NR$^b$oxetan-3-yl where $R^a$ is hydrogen, alkyl, or cycloalkyl;
(d) —C(CH$_3$)$_2$—R$^c$ where R$^c$ is

23

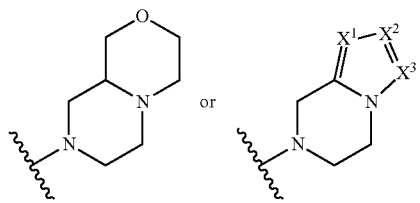 or where one or two of $X^1$, $X^2$ and $X^3$ are nitrogen and the rest are carbon and the ring is optionally substituted with one or two substituents independently selected from alkyl, haloalkyl, or halo; or (e) —C(CH$_3$)$_2$-2-oxa-6-azaspiro[3.3]heptan-6-yl, or —C(CH$_3$)$_2$—CH$_2$morpholine-4-yl; ((in one embodiment R$^c$ is —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—NHoxetan-3-yl, or —C(CH$_3$)$_2$-2-oxa-6-azaspiro[3.3]heptan-6-yl); and/or a pharmaceutically acceptable salt thereof;

comprising:

(a) reacting a compound of formula (1):

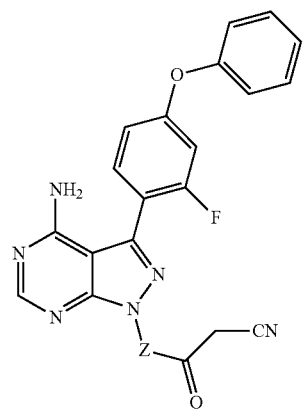

(1)

where:
—Z— is as defined above;
with an aldehyde of formula R$^c$CHO where R$^c$ is:
(a) —C(CH$_3$)$_2$-(4-R$^4$-piperazin-1-yl) where R$^4$ is hydrogen, alkyl, alkoxyalkyl, haloalkyl, alkylsulfonyl, alkoxycarbonyl, acyl, or oxetan-3-yl and the piperazinyl ring is additionally optionally substituted with one or two alkyl;
(b) —C(CH$_3$)$_2$-(3-oxo-4-R$^a$-piperazin-1-yl) where R$^a$ is hydrogen, alkyl, alkoxyalkyl, haloalkyl, or oxetan-3-yl and the piperazinyl ring is additionally optionally substituted with one or two alkyl;
(c) —C(CH$_3$)$_2$—NR$^b$oxetan-3-yl where R$^b$ is hydrogen, alkyl, or cycloalkyl;

24

(d) —C(CH$_3$)$_2$—R$^c$ where R$^c$ is

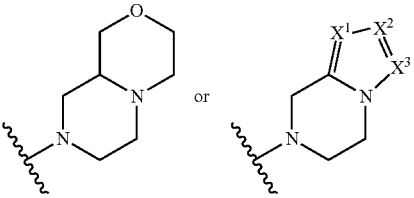 or where one or two of $X^1$, $X^2$ and $X^3$ are nitrogen and the rest are carbon and the ring is optionally substituted with one or two substituents independently selected from alkyl, haloalkyl, or halo; or (e) —C(CH$_3$)$_2$-2-oxa-6-azaspiro[3.3]heptan-6-yl, or —C(CH$_3$)$_2$—CH$_2$morpholine-4-yl; (in one embodiment R$^c$ is —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—NHoxetan-3-yl, or —C(CH$_3$)$_2$-2-oxa-6-azaspiro[3.3]heptan-6-yl); or (b) reacting a compound of formula (2):

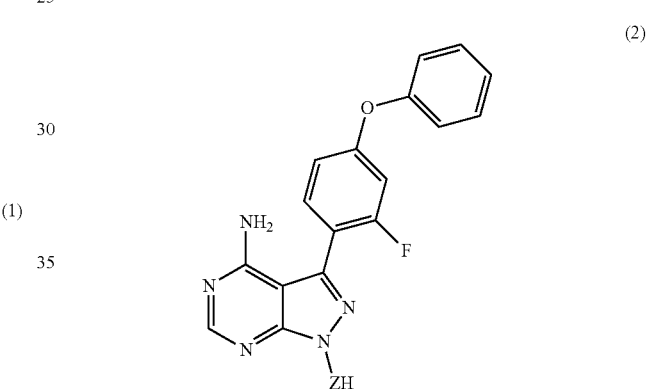

(2)

where:
—Z— is as defined above;
with a compound of formula R$^c$CH=C(CN)CO$_2$H or R$^c$CH—C(CN)COX where R$^c$ is:
(a) —C(CH$_3$)$_2$-(4-R$^4$-piperazin-1-yl) where R$^4$ is hydrogen, alkyl, alkoxyalkyl, haloalkyl, alkylsulfonyl, alkoxycarbonyl, acyl, or oxetan-3-yl and the piperazinyl ring is additionally optionally substituted with one or two alkyl;
(b) —C(CH$_3$)$_2$-(3-oxo-4-R$^a$-piperazin-1-yl) where R$^e$ is hydrogen, alkyl, alkoxyalkyl, haloalkyl, or oxetan-3-yl and the piperazinyl ring is additionally optionally substituted with one or two alkyl;
(c) —C(CH$_3$)$_2$—NR$^b$oxetan-3-yl where R$^b$ is hydrogen, alkyl, or cycloalkyl;
(d) —C(CH$_3$)$_2$—R$^c$ where R$^c$ is

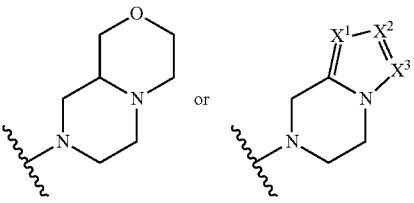

where one or two of $X^1$, $X^2$ and $X^3$ are nitrogen and the rest are carbon and the ring is optionally substituted with one or two substituents independently selected from alkyl, haloalkyl, or halo; or (e) —C(CH$_3$)$_2$-2-oxa-6-azaspiro[3.3]heptan-6-yl, or —C(CH$_3$)$_2$—CH$_2$morpholine-4-yl; (in one embodiment R$^c$ is —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—NHoxetan-3-yl, or —C(CH$_3$)$_2$-2-oxa-6-azaspiro[3.3]heptan-6-yl);

where X is a leaving group, capable of being displaced by the nitrogen atom of the Z group under amide coupling reaction conditions;

(c) optionally making an acid addition salt of a compound obtained from Steps (a) or (b) above;

(d) optionally making a free base of a compound obtained from Steps (a), (b), or (c) above;

(e) optionally separating individual stereoisomers of the compounds obtained from Steps (a), (b), (c), or (d) above; and (f) optionally separating individual (E) and (Z) isomers of the compounds obtained from Steps (a), (b), (c), (d), or (e) above.

In one embodiment of the disclosed process, Z is

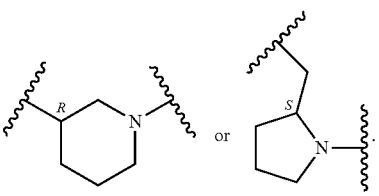

In another embodiment of the disclosed process, Z is

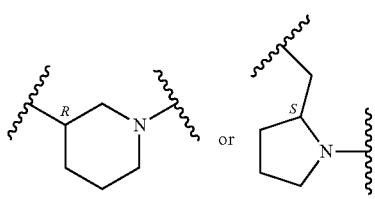

and R$^c$ is —C(CH$_3$)$_2$-(4-methylpiperazin-1-yl).

In yet another embodiment of the disclosed process, Z is

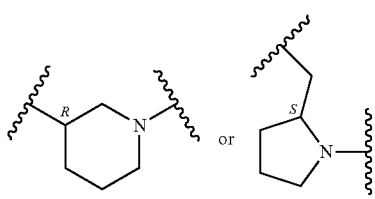

and R$^c$ is —C(CH$_3$)$_2$-(piperazin-1-yl).

In yet another embodiment of the disclosed process, Z is

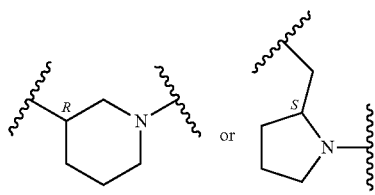

and R$^c$ is —C(CH$_3$)$_2$—N(CH$_3$)oxetan-3-yl.

In yet another embodiment of the disclosed process, Z is

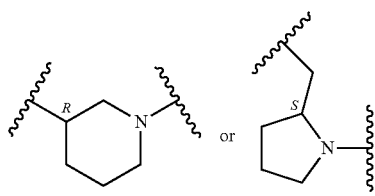

and R$^c$ is —C(CH$_3$)$_2$—NHoxetan-3-yl.

In yet another embodiment of the disclosed process, Z is

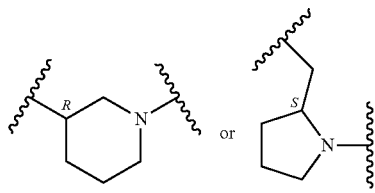

and R$^c$ is —C(CH$_3$)$_2$—N(ethyl)oxetan-3-yl.

In yet another embodiment of the disclosed process, Z is

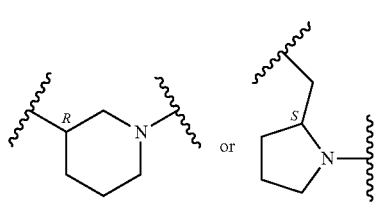

and R$^c$ is —C(CH$_3$)$_2$—N(ethyl)piperazin-1-yl.

In yet another embodiment of the disclosed process, Z is

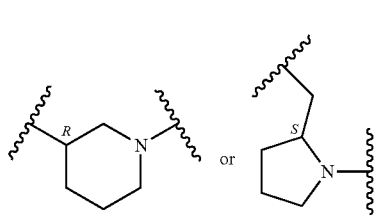

and R$^c$ is —C(CH$_3$)$_2$-(4-methyl-3-oxopiperazin-1-yl).

In yet another embodiment of the disclosed process, Z is

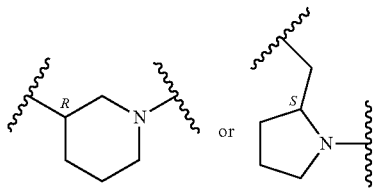

and R$^c$ is —C(CH$_3$)$_2$-(4-(2-ethoxyethyl)-piperazin-1-yl).

In yet another embodiment of the disclosed process, Z is

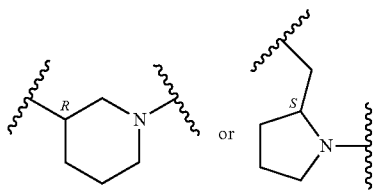

and R$^c$ is —C(CH$_3$)$_2$-4-(oxetan-3-yl)-piperazin-1-yl.

In another embodiment of the disclosed process, the compound of Formula (IA) (and embodiments thereof) is prepared by method (a) by reacting a compound of formula (1):

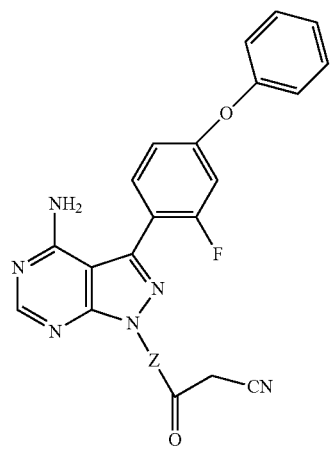

where:
—Z— is as defined above;
with an aldehyde of formula R$^c$CHO where R$^c$ is:
(a) —C(CH$_3$)$_2$-(4-R$^4$-piperazin-1-yl) where R$^4$ is hydrogen, alkyl, alkoxyalkyl, haloalkyl, alkylsulfonyl, alkoxycarbonyl, acyl, or oxetan-3-yl and the piperazinyl ring is additionally optionally substituted with one or two alkyl;
(b) —C(CH$_3$)$_2$-(3-oxo-4-R$^a$-piperazin-1-yl) where R$^a$ is hydrogen, alkyl, alkoxyalkyl, haloalkyl, or oxetan-3-yl and the piperazinyl ring is additionally optionally substituted with one or two alkyl;
(c) —C(CH$_3$)$_2$—NR$^b$oxetan-3-yl where R$^b$ is hydrogen, alkyl, or cycloalkyl;

(d) —C(CH$_3$)$_2$—R$^c$ where R$^c$ is

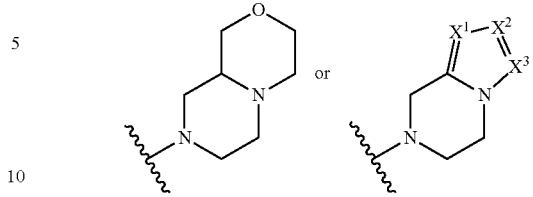

where one or two of X$^1$, X$^2$ and X$^3$ are nitrogen and the rest are carbon and the ring is optionally substituted with one or two substituents independently selected from alkyl, haloalkyl, or halo; or
(e) —C(CH$_3$)$_2$-2-oxa-6-azaspiro[3.3]heptan-6-yl, or —C(CH$_3$)$_2$—CH$_2$morpholine-4-yl; (in one embodiment R$^c$ is —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—NHoxetan-3-yl, —C(CH$_3$)$_2$-2-oxa-6-azaspiro[3.3]heptan-6-yl, —C(CH$_3$)$_2$-(4-methyl-3-oxopiperazin-1-yl, or —C(CH$_3$)$_2$-(4-(2-ethoxyethyl)-piperazin-1-yl), such as —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—NHoxetan-3-yl, —C(CH$_3$)$_2$-2-oxa-6-azaspiro[3.3]heptan-6-yl);
in the presence of pyrrolidine and trimethylsilyl chloride.

In another embodiment of the disclosed process, the compound of Formula (IA) (and embodiments thereof) is prepared by method (b) by reacting a compound of formula (2):

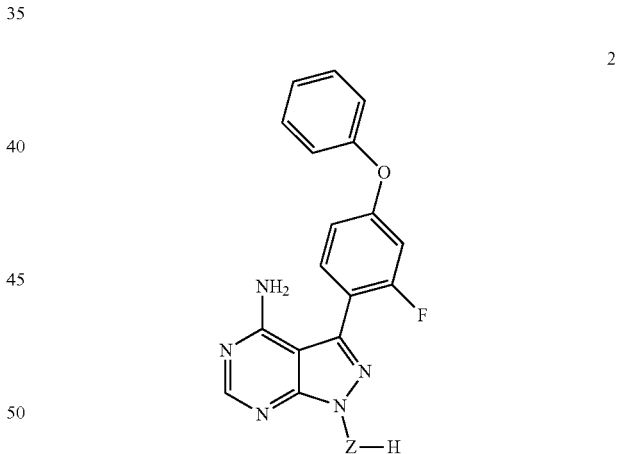

where:
—Z— is as defined above;
with a compound of formula R$^c$CH═C(CN)COOH or R$^c$CH═C(CN)COX where R$^c$ is:
(a) —C(CH$_3$)$_2$-(4-R$^4$-piperazin-1-yl) where R$^4$ is hydrogen, alkyl, alkoxyalkyl, haloalkyl, alkylsulfonyl, alkoxycarbonyl, acyl, or oxetan-3-yl and the piperazinyl ring is additionally optionally substituted with one or two alkyl;
(b) —C(CH$_3$)$_2$-(3-oxo-4-R$^a$-piperazin-1-yl) where R$^a$ is hydrogen, alkyl, alkoxyalkyl, haloalkyl, or oxetan-3-yl and the piperazinyl ring is additionally optionally substituted with one or two alkyl;
(c) —C(CH$_3$)$_2$—NR$^b$oxetan-3-yl where R$^b$ is hydrogen, alkyl, or cycloalkyl;

(d) —C(CH$_3$)$_2$—R$^c$ where R$^c$ is

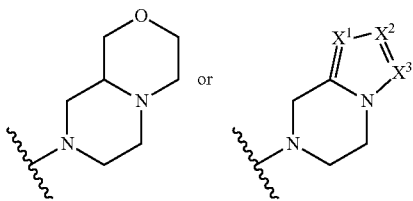

where one or two of X$^1$, X$^2$ and X$^3$ are nitrogen and the rest are carbon and the ring is optionally substituted with one or two substituents independently selected from alkyl, haloalkyl, or halo; or (e) —C(CH$_3$)$_2$-2-oxa-6-azaspiro[3.3]heptan-6-yl, or —C(CH$_3$)$_2$—CH$_2$morpholine-4-yl; (in one embodiment R$^c$ is —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—NHoxetan-3-yl, —C(CH$_3$)$_2$-2-oxa-6-azaspiro[3.3]heptan-6-yl, —C(CH$_3$)$_2$-(4-methyl-3-oxopiperazin-1-yl, or —C(CH$_3$)$_2$-(4-(2-ethoxyethyl)-piperazin-1-yl), such as —C(CH$_3$)$_2$-(piperazin-1-yl), —C(CH$_3$)$_2$-(4-methylpiperazin-1-yl), —C(CH$_3$)$_2$-(4-ethylpiperazin-1-yl), —C(CH$_3$)$_2$—N(CH$_3$)oxetan-3-yl, —C(CH$_3$)$_2$—N(CH$_2$CH$_3$)oxetan-3-yl, —C(CH$_3$)$_2$—NHoxetan-3-yl, —C(CH$_3$)$_2$-2-oxa-6-azaspiro[3.3]heptan-6-yl);

where X is a leaving group, capable of being displaced by the nitrogen atom of the Z group under amide coupling reaction conditions.

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl(including all isomeric forms), and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with an alkoxy group, as defined above, e.g., 2-methoxyethyl, 1-, 2-, or 3-methoxypropyl, 2-ethoxyethyl, and the like.

"Hydroxyalkyl" means a linear monovalent hydrocarbon radical of one to six carbon atoms or a branched monovalent hydrocarbon radical of three to six carbons substituted with a hydroxy group, as defined above, e.g., 2-hydroxyethyl, 1,3-dihydroxypropyl, and the like.

"Alkylsulfonyl" means a —SO$_2$R radical where R is alkyl as defined above, e.g., methylsulfonyl, ethylsulfonyl, and the like.

"Alkoxycarbonyl" means a —C(O)OR radical where R is alkyl as defined above, e.g., methoxycarbonyl, ethoxycarbonyl, and the like.

"Acyl" means a —COR radical where R is alkyl as defined above.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Halo" means fluoro, chloro, bromo, or iodo, such as fluoro or chloro.

"Haloalkyl" means alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like.

The present disclosure also includes amorphous and polymorphic forms and deuterated forms of compounds disclosed herein.

A "pharmaceutically acceptable salt" of a compound means a salt that is pharmaceutically acceptable and that possesses the desired pharmacological activity of the compound from which the salt is made (hereafter, sometimes referred to as "parent compound."). Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985 and Berge et al., *Journal of Pharmaceutical Sciences,* January 1977, Volume 66, Number 1, 1-19 which is incorporated herein by reference.

The compounds of the present disclosure may have asymmetric centers. Certain compounds of the present disclosure containing an asymmetrically substituted atom may be isolated in optically active or racemic forms. It is well-known in the art how to prepare optically active forms, such as by resolution of materials. All chiral, diastereomeric, and racemic forms are within the scope of this disclosure, unless the specific stereochemistry or isomeric form is specifically indicated.

Certain compounds of the present disclosure can exist as tautomers and/or geometric isomers. All possible tautomers and cis and trans isomers, as individual forms and mixtures thereof are within the scope of this disclosure.

"Optional" or "optionally" means that the subsequently described event or circumstance may but need not occur, and that the description includes instances where the event or circumstance occurs and instances in which it does not.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for human pharmaceutical use.

"A pharmaceutically acceptable carrier/excipient" as used in the specification and claims includes both one and more than one such excipient.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or
(3) relieving the disease, i.e., causing regression of the disease or its clinical symptoms.

A "therapeutically effective amount" means the amount of a compound of the present disclosure that, when administered to a patient in need or recognized need of treatment for treating a disease, is sufficient to effect such treatment for the disease. The "therapeutically effective amount" will vary depending on the compound, the disease and its severity, and the age, weight, etc., of the mammal to be treated.

The compounds disclosed herein are tyrosine kinase inhibitors, in particular BTK and hence are useful in the treatment of autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, including Sjogren's dry eye, non-Sjogren's dry eye, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, and vulvodynia.

The compounds disclosed herein are also useful in the treatment of a heteroimmune condition or disease. In another embodiment described herein, the patient in need or recognized need is suffering from a heteroimmune condition or disease, e.g., graft versus host disease, transplantation, transfusion, anaphylaxis, allergy, type I hypersensitivity, allergic conjunctivitis, allergic rhinitis, and atopic dermatitis.

In another embodiment disclosed herein, the patient in need or recognized need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis. In one embodiment, the inflammatory disease is asthma.

In another embodiment disclosed herein, the patient in need or recognized need is suffering from inflammatory skin disease which includes, by way of example, dermatitis, contact dermatitis, eczema, rosacea, and scarring psoriatic lesions in the skin, joints, or other tissues or organs.

In yet another embodiment disclosed herein, the patient in need or recognized need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, chromic myleogenous leukemia, B-ALL, Philadelphia chromosome positive B-ALL lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, the compound disclosed herein is administered in combination with another an anti-cancer agent e.g., the anti-cancer agent is an inhibitor of mitogen-activated protein kinase signaling, e.g., U0126, PD98059, PD184352, PD0325901, ARRY-142886, SB239063. SP600125, BAY 43-9006, wortmannin, or LY294002.

In yet another embodiment disclosed herein, the patient in need or recognized need is suffering from a thromboembolic disorder, e.g., myocardial infarction, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

Yet another embodiment disclosed herein is the use of compounds and/or a pharmaceutically acceptable salt thereof disclosed herein for use as a medicament. In one embodiment, the use is for treating inflammatory disease or proliferative diseases.

In yet another embodiment disclosed herein is the use of a compound and/or a pharmaceutically acceptable salt thereof disclosed herein in the manufacture of a medicament for treating an inflammatory disease in a patient in need or recognized need of such treatment in which the activity of BTK or other tyrosine kinases contribute to the pathology and/or symptoms of the disease. In one embodiment the tyrosine kinase protein is BTK. In another embodiment, the disease is chosen from respiratory, cardiovascular, and proliferative diseases.

In any of the aforementioned embodiments disclosed herein involving the treatment of proliferative disorders, including cancer, are further embodiments involving combination therapy. In those embodiments, the compound and/or a pharmaceutically acceptable salt thereof disclosed herein is administered in combination with at least one additional agent chosen from alemtuzumab, arsenic trioxide, asparaginase (pegylated or non-), bevacizumab, cetuximab, platinum-based compounds such as cisplatin, cladribine, aunorubicin/doxorubicin/idarubicin, irinotecan, fludarabine, 5-fluorouracil, gemtuzamab, methotrexate, paclitaxel, Taxol™, docetaxol, temozolomide, thioguanine, or classes of drugs including hormones (an antiestrogen, an antiandrogen, and gonadotropin releasing hormone analogues, interferons such as alpha interferon, nitrogen mustards, such as busulfan, melphalan, and mechlorethamine, retinoids, such as tretinoin, topoisomerase inhibitors, such as irinotecan and topotecan, tyrosine kinase inhibitors such as gefinitinib and imatinib, and agents to treat signs or symptoms induced by such therapy including, for example, allopurinol, filgrastim, granisetron/ondansetron/palonosetron, and dronabinol. When combination therapy is used, the agents can be administered simultaneously or sequentially. The kinase inhibitory activity of the compounds of the present disclosure can be tested by methods well known the the art. The BTK inhibitory activity of the compounds and/or a pharmaceutically acceptable salt thereof of the present disclosure can be tested using the in vitro and in vivo assays described in Biological Examples 1-3 below. A determination of kinase inhibitory activity by any of those assays is considered to be kinase inhibitory activity within the scope of this disclosure even if any or all of the other assays do not result in a determination of kinase inhibitory activity.

Without being bound to any specific mechanistic theory, in those embodiments wherein the compound of the present disclosure is a reversible covalent inhibitor, it is believed that the cysteine sulfhydryl group and a carbon atom forming part of the carbon-carbon double bond (i.e. olefin) of the compound of the present disclosure can form a reversible, i.e., labile, covalent bond, defined herein, such as wherein Cys 481 attacks an electron deficient carbon atom of the carbon-carbon double bond (olefin) in the compound of present disclosure to form a thiol adduct (e.g., Michael reaction with cysteine).

In some embodiments, the electron deficient carbon atom of the olefin is distal to the carbon attached to the cyano group and to the electron withdrawing —Z—CO— moiety (see Formula I, IA, IB, III) in the compounds of the present disclosure. Therefore, the combination of the cyano and the "—Z—CO—" moieties and the olefinic moiety to which they are bonded in the compounds of the present disclosure can increase the reactivity of the olefin to form a thiol adduct with the active site cysteine residue in BTK.

The compounds of the present disclosure bind with BTK in two different manners. In addition to the labile covalent binding, discussed above, they also form non-covalent binding (e.g., via van der Waals binding, hydrogen binding, hydrophobic binding, hydrophilic binding, and/or electrostatic charge binding) with BTK, the non-covalent binding being sufficient to at least partially inhibit the kinase activity of the BTK.

As disclosed herein, the labile covalent binding between the the compound of the disclosure and BTK occurs between the olefin in the inhibitor and the cysteine 481 residue thiol side chain at or near the site where the compound has the aforementioned non-covalent binding with the BTK.

As is evident, the compounds of the present disclosure which are reversible covalent inhibitors have both a cysteine-mediated covalent binding and a non-covalent binding with the BTK. This is in contrast with non-covalent reversible inhibitors which inhibit the BTK only via non-covalent binding and lack the cysteine-mediated covalent binding.

The result of the binding of the compounds of the present disclosure with BTK in the two different manners is a reversible covalent inhibitor having a slow off-rate and a protracted duration of action, in some instances comparable to an irreversible covalent inhibitor without forming permanent irreversible protein adducts. The difference between irreversible and reversible covalent inhibitors, particulary the compounds disclosed herein, can be ascertained utilizing assays disclosed herein.

In general, the binding involved in an inhibitor that forms a reversible covalent bond with BTK, i.e., the compounds disclosed herein, is stable when the BTK is in certain configurations and susceptible to being broken when the BTK is in different configurations (in both cases under physiologic conditions), whereas the interaction between an inhibitor that forms an irreversible covalent bond is stable under physiologic conditions even when the BTK is in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drug-target residence time and its implications for lead optimization. Nat. Rev. Drug Discov. 5(9), 730-739 (2006).

The presence of a reversible covalent bond in a reversible covalent inhibitor as disclosed herein can lead to an extended residence time when compared to a compound that does not form a covalent bond with BTK. In one embodiment disclosed herein the compounds of the present disclosure that are reversible covalent inhibitors have a residence time of at least about 1 h, residence time may be measured using an occupancy assay in a biochemical or cellular environment (see Biological Example 7 below). Additionally, residence time may be measured using a functional assay following a defined wash-out period.

Compounds that form an irreversible covalent bond in an irreversible covalent inhibitor share these extended residence time properties but may nonetheless be differentiated from a reversible covalent inhibitor using a reversibility assay. The ability of the compound of the disclosure to form reversible covalent bond with Cys481 of BTK (UniprotKB Sequence ID Q06187) and the olefinic bond in the compound of the disclosure, can be determined by the assays described in Biological Examples 5-8 below. A determination of the binding reversibility of the covalent bond between the cysteine residue and the olefinic bond of the compound of the disclosure by any of Biological Examples 5-8 below is considered to be binding reversibility within the scope of this disclosure even if one or more of the other methods does not result in a determination of binding reversibility.

In general, the compounds of this disclosure will be administered in a therapeutically effective amount by any of the accepted modes of administration for agents that serve similar utilities. Therapeutically effective amounts of the compounds disclosed herein may range from about 0.01 to about 500 mg per kg patient body weight per day, which can be administered in single or multiple doses. A suitable dosage level may be about 0.01 to about 250 mg/kg per day, about 0.05 to about 100 mg/kg per day, or about 0.1 to about 50 mg/kg per day. Within this range, the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount administered of the compound and/or a pharmaceutically acceptable salt thereof of this disclosure, i.e., the active ingredient, will depend upon numerous factors such as the severity of the disease to be treated, the age and relative health of the patient, the potency of the compound and/or pharmaceutically acceptable salt thereof being utilized, the route and form of administration, and other factors.

In general, compounds and/or pharmaceutically acceptable salts of this disclosure will be administered as pharmaceutical compositions by any one of the following routes: oral, systemic (e.g., transdermal, intranasal or by suppository), topically, or parenteral (e.g., intramuscular, intravenous or subcutaneous) administration. The preferred manner of administration is oral using a convenient daily dosage regimen, which can be adjusted according to the degree of affliction. Compositions can take the form of tablets, capsules, semisolids, powders, sustained release formulations, enteric coated or delayed release formulation, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound and/or pharmaceutically acceptable salt disclosed herein in combination with at least one pharmaceutically acceptable excipient such as binders, surfactants, diluents, buffering agents, antiadherents, glidants, hydrophilic or hydrophobic polymers, retardants, stabilizing agents or stabilizers, disintegrants or superdisintegrants, antioxidants, antifoaming agents, fillers, flavors, colors, lubricants, sorbents, preservatives, plasticizers, and sweeteners. Acceptable excipients are non-toxic, aid administration, and do not adversely affect the therapeutic benefit of the compound disclosed herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols.

The compounds and/or pharmaceutically acceptable salt of the present disclosure can also be administered intranasally. Intranasal formulations are known in the art e.g., see U.S. Pat. Nos. 4,476,116, 5,116,817 and 6,391,452, each of which is incorporated herein by reference. The choice of excipients will depend upon the nature of the nasal dosage form e.g., solutions, suspensions, or powder. For administration by inhalation, the compounds and/or pharmaceutically acceptable salts of the present disclosure may be in the form of solutions, suspensions, and powders. These formulations are administered as an aerosol, a mist, or a powder and can be delivered from pressurized packs or a nebulizer with a suitable propellant such as dichlorodifluoromethane, trichlorofluoromethane, nitrogen, carbon dioxide, etc. In the case of a pressurized aerosol, the dosage unit may be determined by providing a valve to deliver a metered amount. Capsules and cartridges for use in an inhaler may be formulated containing a powder mix of the compound disclosed herein and a suitable powder base such as lactose or starch.

Topical formulation can be liquids, suspension, emulsions, and the like, and can be prepared by methods well known in the art. The formulation will contain, on a weight percent (wt %) basis, from about 0.01-99.99 wt % of a compound and/or pharmaceutically acceptable salt disclosed herein based on the total formulation, with the balance being one or more suitable pharmaceutical excipients amd can be administered in single or multiple doses. Suitable excipients include polymers, surfactants, buffering or pH adjusting agents, tonicity and osmotic adjusting agent(s), preservatives, and dispersing agents.

Other suitable pharmaceutical excipients and their formulations are described in Remington's Pharmaceutical Sciences, edited by E. W. Martin (Mack Publishing Company, $20^{th}$ ed., 2000).

The level of the compound in a formulation can vary within the full range employed by those skilled in the art. Typically, the formulation will contain, on a weight percent (wt %) basis, from about 0.01-99.99 wt % of a compound and/or pharmaceutically acceptable salt disclosed herein based on the total formulation, with the balance being one or more suitable pharmaceutical excipients.

The compounds and/or pharmaceutically acceptable salts of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound and/or pharmaceutically acceptable salt of the present disclosure is used contemporaneously with one or more other drugs, a pharmaceutical composition in unit dosage form containing such other drugs and the compound and/or pharmaceutically acceptable salt of the present disclosure is preferred. However, the combination therapy may also include therapies in which the compound and/or pharmaceutically acceptable salt of the present disclosure and one or more other drugs are administered on different overlapping schedules. It is also contemplated that when used in combination with one or more other active ingredients, the compounds and/or pharmaceutically acceptable salts of the present disclosure and the other active ingredients may be used in lower doses than when each is used singly.

Accordingly, the pharmaceutical compositions of the present disclosure also include those that contain one or more other active ingredients, in addition to a compound and/or pharmaceutically acceptable salt of the present disclosure.

The above combinations include combinations of a compound of the present disclosure not only with one other active compound, but also with two or more other active compounds. Likewise, compounds and/or pharmaceutically acceptable salts of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore by those skilled in the art, contemporaneously or sequentially with a compound and/or pharmaceutically acceptable salt of the present disclosure. When a compound and/or pharmaceutically acceptable salt of the present disclosure is used contemporaneously with one or more other drugs, a pharmaceutical composition containing such other drugs in addition to the compound and/or pharmaceutically acceptable salt of the present disclosure is preferred. Accordingly, the pharmaceutical compositions of the present disclosure also include those that also contain one or more other active ingredients, in addition to a compound and/or pharmaceutically acceptable salt of the present disclosure. The weight ratio of the compound and/or pharmaceutically acceptable salt of the present disclosure to the second active ingredient may be varied and will depend upon the effective dose of each ingredient. Generally, an effective dose of each will be used.

Where the patient is suffering from or at risk of suffering from an autoimmune disease, an inflammatory disease, or an allergy disease, a compound and/or pharmaceutically acceptable salt of present disclosure can be used in with one or more of the following therapeutic agents in any combination: immunosuppressants (e.g., tacrolimus, diethylstilbestrol, rapamicin, methotrexatc, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, and anticholinergics.

Where the patient is suffering from or at risk of suffering from a B-cell proliferative disorder (e.g., plasma cell myeloma), the patient can be treated with a compound and/or pharmaceutically acceptable salt disclosed herein in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygcldanamycin (17-AAG), flavopiridol, LY294002, bortezomib, trastuzumab, BAY 11-7082, PKC412, or PD 184352, Taxol™, also referred to as "paclitaxel", which is a well-known anti-cancer drug which acts by enhancing and stabilizing microtubule formation, and docetaxol, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound disclosed herein include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound disclosed herein include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a: interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansinc; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound and/or pharmaceutically acceptable salt disclosed herein include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin mI derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselcn; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium tcxaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobcnguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+diethylstilbestrol cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound disclosed herein include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound or a pharmaceutically acceptable salt disclosed herein include but are not limited to *vinca* alkaloids (e.g., diethylstilbestrol, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound or a pharmaceutically acceptable salt disclosed herein include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound or a pharmaceutically acceptable salt disclosed herein include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an BTK inhibitor compound and/or a pharmaceutically acceptable salt of the disclosure include without limitation the following marketed drugs and drugs in development: Erbulozole (also known as R-55104), Dolastatin 10 (also known as DLS-10 and NSC-376128), Mivobulin isethionate (also known as CT-980), Vincristine, NSC-639829. Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651). SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067). COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607). RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B. D-64131 (Asta Medica), D-68144 (Asta Medica), Diazonamide A, A-293620 (Abbott), NPI-2350 (Ncrcus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the patient is suffering from or at risk of suffering from a thromboembolic disorder (e.g., stroke), the patient can be treated with a compound and/or pharmaceutically acceptable salt disclosed herein in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

EXAMPLES

The following preparations of intermediates (References) and final compounds (Examples) disclosed herein are given to enable those skilled in the art to more clearly understand and to practice the present disclosure. They should not be considered as limiting the scope of the disclosure, but merely as being illustrative and representative thereof. The ⌇ line at the alkene carbon, in the compounds below, denotes that the compounds are isolated as an undefined mixture of (E) and (Z) isomers.

Reference 1

Synthesis of 3-iodo-1H-pyrazolo[3,4-d]pyrimidin-4-amine

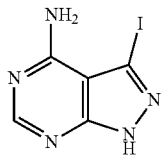

A mixture of 1H-pyrazolo[3,4-d]pyrimidin-4-amine (150 g, 1.11 mol, 1.00 equiv) and N-iodo-succinimide (375 g, 1.67 mol, 1.58 equiv) in N,N-dimethylformamide (2.5 L) was stirred at 80° C. for 5 h. The reaction mixture was cooled to room temperature and then diluted with 10 L of water. The solid was collected by filtration, washed with 2×1 L of saturated aqueous sodium sulfite, and dried under vacuum to give 150 g of 3-iodo-1H-pyrazolo[3,4-d]pyrimidin-4-amine as a yellow solid.

Reference 2

Synthesis of (R)-tert-butyl 3-(4-amino-3-iodo-1H-pyrazolo[3,4-d]pyrimidin-1-yl)piperidine-1-carboxylate

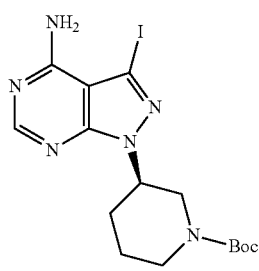 [SMILES: CC(C)(C)OC(=O)N1CCC[C@@H](n2nc(I)c3c(N)ncnc32)C1]

To a stirred mixture of 3-iodo-1H-pyrazolo[3,4-d]pyrimidin-4-amine (5.9 g, 22.6 mmol, 1.00 equiv), (S)-tert-butyl 3-hydroxypiperidine-1-carboxylate (10 g, 50 mmol, 2.2 equiv) and triphenylphosphine (11.8 g, 45 mmol, 2.0 equiv) in tetrahydrofuran (300 mL) at 10° C. was added a solution of diisopropyl azodicarboxylate in tetrahydrofuran (30 mL) dropwise in 30 min. The resulting mixture was stirred at room temperature for 12 h and then concentrated under vacuum. The residue was purified on a silica gel column eluted with dichloromethane/methanol (100/1) to give 3 g of (R)-tert-butyl 3-(4-amino-3-iodo-1H-pyrazolo[3,4-d]pyrimidin-1-yl)piperidine-1-carboxylate as a yellow solid.

Proceeding as described above but substituting (S)-tert-butyl 3-hydroxypiperidine-1-carboxylate with (S)-tert-butyl 2-(hydroxymethyl)-pyrrolidine-1-carboxylate gave tert-butyl (S)-2-([4-amino-3-iodo-1H-pyrazolo[3,4-d]pyrimidin-1-yl]methyl)pyrrolidine-1-carboxylate Reference 3

Synthesis of (2-fluoro-4-phenoxyphenyl)-boronic acid

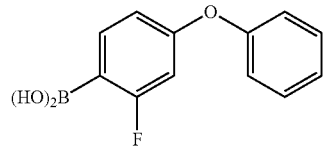 [SMILES: OB(O)c1ccc(Oc2ccccc2)cc1F]

Step 1

Into a 250 mL round-bottom flask, was placed a solution of 4-bromo-3-fluorophenol (5 g, 26.18 mmol, 1.00 equiv) in dichloromethane (100 mL), phenylboronic acid (3.5 g, 28.70 mmol, 1.10 equiv), Cu(AcO)$_2$ (5.7 g), triethylamine (5.3 g), and 4A molecular sieves (15 g). The resulting solution was stirred overnight at room temperature. The solids were filtered out. The filtrate was dried over anhydrous sodium sulfate and concentrated under vacuum. The residue was loaded onto a silica gel column and eluted with ethyl acetate/petroleum ether (1:100-1:50). This resulted in 2 g of 1-bromo-2-fluoro-4-phenoxybenzene as colorless oil.

Step 2

Into a 100 mL 3-necked round-bottom flask purged and maintained under an inert atmosphere of nitrogen, was placed a solution of 1-bromo-2-fluoro-4-phenoxybenzene (2 g, 7.49 mmol, 1.00 equiv) in tetrahydrofuran (20 mL). BuLi (1M, 8 mL) was added dropwise with stirring at −70 to −80° C. The resulting solution was stirred for 30 min at −70-−80° C. in a liquid nitrogen bath. Tris(propan-2-yl)borate (1.7 g, 9.04 mmol, 1.21 equiv) was added dropwise with stirring at −70 to −80° C. The resulting solution was allowed to react, with stirring, for an additional 2 h while the temperature was maintained at −70 to −80° C. The reaction was then quenched by the addition of 100 mL of water, extracted with ethyl acetate and the organic layers were combined and dried over anhydrous sodium sulfate and concentrated under vacuum. The residue was loaded onto a silica gel column and eluted with ethyl acetate/petroleum ether (1:20) to give 1.6 g of (2-fluoro-4-phenoxyphenyl)boronic acid as a white solid.

Reference 4

Synthesis of 2-cyano-4-methylpent-2-enoic acid

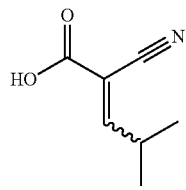

To a solution of 2-cyanoacetic acid (8.7 g, 102 mmol) in methanol (200 mL) was added 2-methylpropanal (18.6 mL, 204 mmol) and the solution was stirred with a slight exotherm noted. After 30 minutes, added piperidine (11.1 mL, 112 mmol) and continued stirring for 1 h before removing solvent in vacuo with gentle heating. The thick material was diluted with ether and washed with 125 mL of 1.0M HCl and then washed with brine. The organic phase was dried over sodium sulfate and concentrated to afford a colorless oil weighing 11.2 g of 2-cyano-4-methylpent-2-enoic acid which precipitated on standing.

Reference 5

Synthesis of 2-cyano-4,4-dimethylpent-2-enoic acid

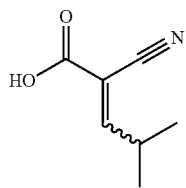

Following the procedure used in reference for but using pivalaldehyde in place of 2-methylpropanal affords. 2-cyano-4,4-dimethylpent-2-enoic acid.

Example 1

Synthesis of 2-((R)-3-(4-amino-3-(2-fluoro-4-phenoxyphenyl)-1H-pyrazolo[3,4-d]pyrimidin-1-yl) piperidine-1-carbonyl)-3-(3-methyloxetan-3-yl)acrylonitrile trifluoroacetic acid salt

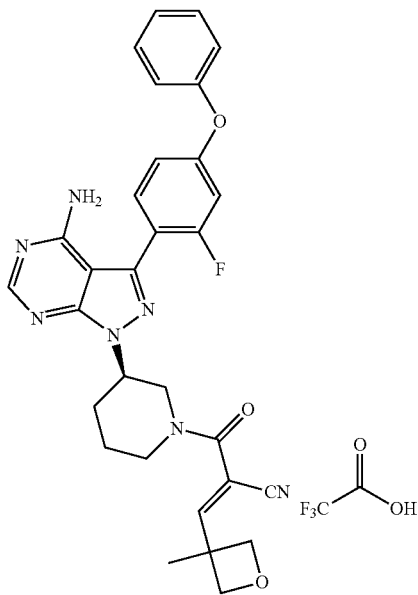

Step 1

Into a 100-mL round-bottom flask, was placed 1,4-dioxane (40 mL), water (10 mL), tert-butyl(3R)-3-[4-amino-3-iodo-1H-pyrazolo[3,4-d]pyrimidin-1-yl]piperidine-1-carboxylate (3.108 g, 7.00 mmol, 1.00 equiv), (2-fluoro-4-phenoxyphenyl)boronic acid (1.624 g, 7.00 mmol, 1.00 equiv), potassium carbonate (2.898 g, 32.89 mmol, 4.70 equiv) and Pd(dppf)Cl$_2$ (57.1 mg, 0.4 mmol, 0.06 equiv).

The resulting solution was stirred overnight at 80° C. in an oil bath. The solids were then filtered out and the resulting solution was diluted with water. The resulting mixture was extracted ethyl acetate. The organic layers were combined, washed with brine, dried over anhydrous sodium sulfate, filtrated, and concentrated. The residue was applied onto a silica gel column with ethyl acetate/petroleum ether (1:3). This resulted in 2.7 g of tert-butyl(3R)-3-[4-amino-3-(2-fluoro-4-phenoxyphenyl)-1H-pyrazolo[3,4-d]pyrimidin-1-yl]piperidine-1-carboxylate as a black solid.

Step 2

Into a 100-mL round-bottom flask, was placed tert-butyl (3R)-3-[4-amino-3-(2-fluoro-4-phenoxyphenyl)-1H-pyrazolo[3,4-d]pyrimidin-1-yl]piperidine-1-carboxylate (2.7 g, 5.35 mmol, 1.00 equiv) and dichloromethane (20 mL). This was followed by the addition of trifluoroacetic acid (5 mL). The resulting solution was stirred for 3 h at room temperature. The resulting mixture was concentrated under vacuum. This resulted in 2.6 g (crude) of 3-(2-fluoro-4-phenoxyphenyl)-1-[(3R)-piperidin-3-yl]-1H-pyrazolo[3,4-d]pyrimidin-4-amine as a brown oil.

Into a 50-mL round-bottom flask, was placed TEA (5.05 g, 49.91 mmol, 10.0 equiv) 3-(2-fluoro-4-phenoxyphenyl)-1-[(3R)-piperidin-3-yl]-1H-pyrazolo[3,4-d]pyrimidin-4-amine (2.02 g, 4.99 mmol, 1.00 equiv), 2-cyanoacetic acid (510 mg, 6.00 mmol, 1.20 equiv), HATU (2.28 g, 6.00 mmol, 1.20 equiv) and N,N-dimethylformamide (40 mL). The resulting solution was stirred for 4 h at room temperature and then diluted with 200 mL of water. The resulting solution was extracted with of ethyl acetate and the organic layers were combined, washed with brine, dried over anhydrous sodium sulfate, filtrated and concentrated under vacuum. This resulted in 600 mg of 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile as a light yellow solid.

Step 4

Into a 50-mL round-bottom flask, was placed a solution of 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile (300 mg, 0.64 mmol, 1.00 equiv) in toluene (10 mL), 3-methyloxetane-3-carbaldehyde (127.4 mg, 1.27 mmol, 2.00 equiv) and piperidine (108.2 mg, 1.27 mmol, 2.00 equiv). The resulting solution was stirred for 4 h at 110° C. in an oil bath and then cooled and concentrated under vacuum. The residue was applied onto a silica gel column and purified with ethyl acetate. This resulted in product (80 mg), which was re-purified by Prep-HPLC with the following conditions (i#-Pre-HPLC-005(Waters)): Column, SunFire Prep C18 19*150 mm 5 um; mobile phase, water with 0.05% trifluoroacetic acid and CH$_3$CN (10% CH$_3$CN up to 70% in 10 min); Detector, 254 nm. This resulted in 22.9 mg (5%) of 2-((R)-3-(4-amino-3-(2-fluoro-4-phenoxyphenyl)-1H-pyrazolo[3,4-d]pyrimidin-1-yl)piperidine-1-carbonyl)-3-(3-methyloxetan-3-yl)acrylonitrile trifluoroacetic acid salt as a white solid. LC-MS (ES, m/z): [M-CF$_3$COOH+H]$^+$ 554.

Proceeding as described in Steps 1, 2 and 3 above but substituting tert-butyl(3R)-3-[4-amino-3-iodo-1H-pyrazolo [3,4-d]pyrimidin-1-yl]piperidine-1-carboxylate with tert-butyl (S)-2-([4-amino-3-iodo-1H-pyrazolo[3,4-d]pyrimidin-1-yl]methyl)pyrrolidine-1-carboxylate, (S)-3-(2-((4-amino-3-(2-fluoro-4-phenoxyphenyl)-1H-pyrazolo[3,4-d] pyrimidin-1-yl)-methyl)pyrrolidin-1-yl)-3-oxopropanenitrile was synthesized.

47

Example 2

Synthesis of 2-((R)-3-(4-amino-3-(2-fluoro-4-phenoxyphenyl)-1H-pyrazolo[3,4-d]pyrimidin-1-yl)piperidine-1-carbonyl)-4-(azetidin-1-yl)-4-methylpent-2-enenitrile bis (2,2,2-trifluoroacetate)

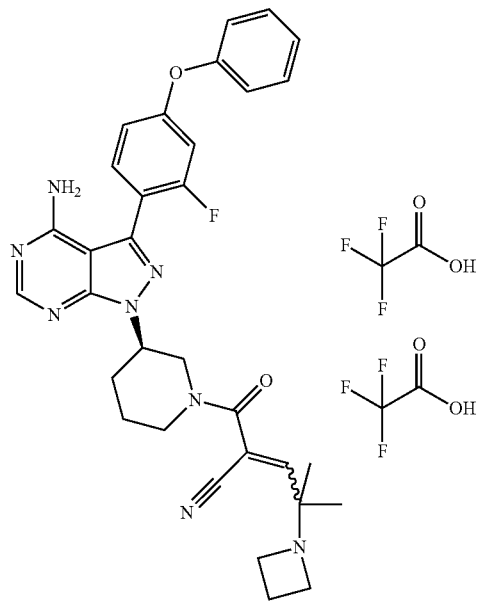

Step 1

To a solution of 2-bromo-2-methylpropanal (0.6 g, 4 mmol, 1.0 equiv) in Et$_2$O (20 mL) at 0° C. was added azetidine (684 mg, 12 mmol, 3.0 equiv) dropwise. The resulting mixture was stirred at 0° C. for 2 hours. The mixture was diluted with water, and extracted with Et$_2$O. The combined organic layer was dried over anhydrous sodium sulfate. The solids were filtered and the solvent concentrated under vacuum. This resulted in 208 mg (41%) of 2-(azetidin-1-yl)-2-methylpropanal as a colorless oil.

Step 2

A solution of 3-((R)-3-(4-amino-3-(2-fluoro-4-phenoxyphenyl)-1H-pyrazolo[3,4-d]pyrimidin-1-yl) piperidin-1-yl)-3-oxopropanenitrile (200 mg, 0.43 mmol, 1.0 equiv), 2-(azetidin-1-yl)-2-methylpropanal (136.5 mg, 2.15 mmol, 5.0 equiv) and piperidine (73.1 mg, 0.86 mmol, 2.0 equiv) in toluene (10 mL) was stirred at 120° C. for 3 hours. The mixture was then concentrated and the crude product was purified by prep-HPLC. This resulted in 39.8 mg of 2-((R)-3-(4-amino-3-(2-fluoro-4-phenoxyphenyl)-1H-pyrazolo[3,4-d]pyrimidin-1-yl) piperidine-1-carbonyl)-4-(azetidin-1-yl)-4-methylpent-2-enenitrile bis (2,2,2-trifluoroacetate) as a white solid. LCMS (ESI, pos. ion) m/z: 581 (M-2TFA+1).

48

Example 3

Synthesis of (R)-2-(3-(4-amino-3-(2-fluoro-4-phenoxyphenyl)-1H-pyrazolo[3,4-d]pyrimidin-1-yl)piperidine-1-carbonyl)-5-hydroxy-4,4-dimethylpent-2-enenitrile

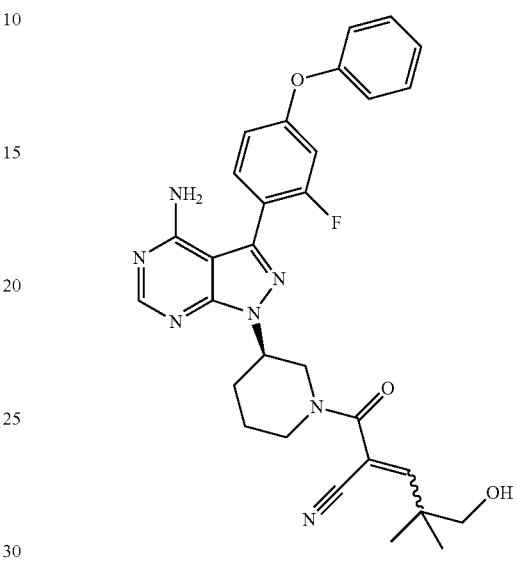

Step 1

To a mixture of 2,2-dimethylpropane-1,3-diol (5 g, 48.01 mmol) and imidazole (4.9 g, 71.97 mmol) in DCM (100 mL) was added TMS-Cl (7.9 g, 52.42 mmol) and the resultant slurry stirred at rt for 1 h. After washing with water and brine, the organic phase was dried over sodium sulfate, filtered, concentrated and purified via column chromatography with 90:10 Hexanes:ethyl acetate to yield 6.5 g of 3-((tert-butyldimethylsilyl)oxy)-2,2-dimethylpropan-1-ol as a colorless oil.

Step 2

A crude mixture of 3-[tert-butyl(dimethyl)silyl]oxy-2,2-dimethyl-propanal (1.15 g, 5.31 mmol) was prepared by addition of 1.1 equivalents of Dess-Martin periodinane to a solution of 3-((tert-butyldimethylsilyl)oxy)-2,2-dimethyl-propan-1-ol in 25 mL of DCM at 0° C. After 1 h, the slurry was diluted with hexanes and filtered over a plug of silica. The residue was concentrated to a thick oil and then dissolved in DCM (10 mL). 3-[(3R)-3-[4-Amino-3-(2-fluoro-4-phenoxy-phenyl)pyrazolo[3,4-d]pyrimidin-1-yl]-1-piperidyl]-3-oxo-propanenitrile (236.79 mg, 0.5000 mmol) was added, then TMS-Cl (0.2 mL, 1.59 mmol), followed by pyrrolidine (0.13 mL, 1.59 mmol). The solution was stirred at rt, monitoring the reaction by LCMS. After 16 h, the mixture was partitioned between water and DCM and then the organic phase was washed with brine and dried over sodium sulfate. Filtration and removal of solvents afforded a colorless oil that was purified by silica gel chromatography (9:1 to 90:10 methylene chloride:MeOH gradient) to afford ~350 mg of (R)-2-(3-(4-amino-3-(2-fluoro-4-phenoxyphenyl)-1H-pyrazolo[3,4-d]pyrimidin-1-yl)piperidine-1-carbonyl)-5-((tert-butyldimethylsilyl)oxy)-4,4-dimethylpent-2-enenitrile.

Step 3

To a solution of 2-[(3R)-3-[4-amino-3-(2-fluoro-4-phenoxy-phenyl)pyrazolo[3,4-d]pyrimidin-1-yl]piperidine-1- carbonyl]-5-[tert-butyl(dimethyl)silyl]oxy-4,4-dimethyl-pent-2-enenitrile (350 mg, 0.5200 mmol) in DCM (5 mL) was added approximately 2.5 ml of TFA and the solution was stirred at rt overnight. The next day the compound was partitioned between water and dichloromethane and the organic phase was dried over sodium sulfate. After filtration and removal of solvents the crude material was flash purified (99:1-92:8 gradient DCM:MeOH). The clean fractions were concentrated, dissolved in a minimum of acetonitrile and water, frozen and lyophilized to obtain a colorless powder weighing 46 mg of (R)-2-(3-(4-amino-3-(2-fluoro-4-phenoxyphenyl)-1H-pyrazolo[3,4-d]pyrimidin-1-yl)piperidine-1-carbonyl)-5-hydroxy-4,4-dimethylpent-2-enenitrile. LC-MS (ES, m/z): 557 [M+H].

Example 4

Synthesis of 2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methyl-piperazin-1-yl)pent-2-enenitrile

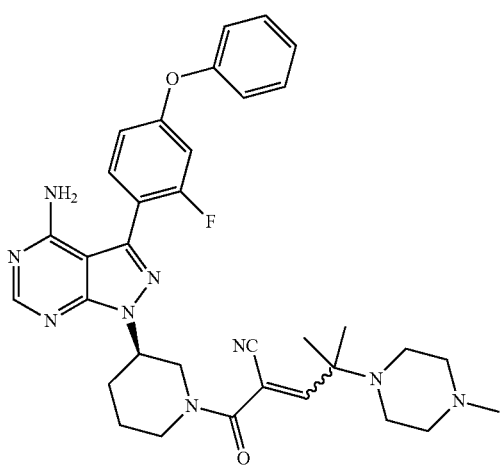 [SMILES: CN1CCN(C(C)(C)C=C(C#N)C(=O)N2CCC[C@@H](n3nc(-c4ccc(Oc5ccccc5)cc4F)c4c(N)ncnc43)C2)CC1]

Step 1

Into a 50-mL 3-necked round-bottom flask, was placed a solution of 2-bromo-2-methylpropanal (2 g, 13.24 mmol, 1.00 equiv) in ether (10 mL). This was followed by the addition of 1-methylpiperazine (4.66 g, 46.52 mmol, 3.51 equiv) dropwise at 0° C. The resulting solution was stirred at room temperature overnight. The solid was filtered off. The filtrate was diluted with water. The resulting mixture was washed with ether. The pH value of the aqueous layers was adjusted to 12 with potassium carbonate. The resulting solution was extracted with dichloromethane and the organic layers combined, washed with brine, dried over sodium sulfate and concentrated under vacuum. This resulted in 740 mg of 2-methyl-2-(4-methylpiperazin-1-yl)propanal as a yellow oil.

Step 2

Into a 500-mL round-bottom flask, was placed N,N-dimethylformamide (20 mL), 3-(2-fluoro-4-phenoxyphenyl)-1-[(3R)-piperidin-3-yl]-1H-pyrazolo[3,4-d]pyrimidin-4-amine (8.04 g, 19.88 mmol, 1.00 equiv), 2-cyanoacetic acid (2.0 g, 23.51 mmol, 1.18 equiv), HATU (9.12 g, 24.00 mmol, 1.21 equiv) and TEA (21.2 mL, 10.00 equiv). The resulting solution was stirred for 4 h at room temperature and then diluted with 500 mL of water. The resulting solution was extracted with 4×300 mL of ethyl acetate. The organic layers were combined, washed with brine, dried over sodium sulfate, filtrated and concentrated under vacuum. This resulted in 6.2 g of 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile as a yellow solid.

Step 3

Into a 100-mL round-bottom flask, was placed a solution of toluene (10 mL), 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile (300 mg, 0.64 mmol, 1.00 equiv), 2-methyl-2-(4-methylpiperazin-1-yl)propanal (541.45 mg, 3.18 mmol, 5.00 equiv), and piperidine (108.29 mg, 1.27 mmol, 2.00 equiv). The resulting solution was stirred for 3 h at 120° C. in an oil bath. The resulting mixture was concentrated under vacuum. The residue was applied onto a silica gel column with ethyl acetate:MeOH (5:1). The crude product (70 mg) was purified by Flash-Prep-HPLC with the following conditions (IntelFlash-1): Column, $C_{18}$ silica gel; mobile phase, $H_2O$ (0.5% TFA)/$CH_3CN$=10% increasing to $H_2O$ (0.5% TFA)/$CH_3CN$=40% within 10 min; Detector, UV 254 nm. This resulted in 46.4 mg (12%) of 2-[[(3R)-3-[4-amino-3-(2-fluoro-4-phenoxyphenyl)-1H-pyrazolo[3,4-d]pyrimidin-1-yl]piperidin-1-yl]carbonyl]-4-methyl-4-(4-methylpiperazin-1-yl)pent-2-enenitrile as a white solid. LC-MS—PH-PBF-003-96-0: (ES, m/z): $[M+H]^+$ 625

Example 5

Synthesis of (S)-2-(2-((4-amino-3-(2-fluoro-4-phenoxyphenyl)-1H-pyrazolo[3,4-d]-pyrimidin-1-yl)-methyl)pyrrolidine-1-carbonyl)-4-methyl-4-(pyrrolidin-1-yl)pent-2-enenitrile

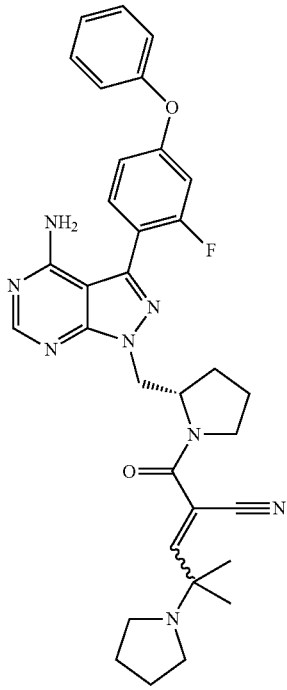 [SMILES: CC(C)(C=C(C#N)C(=O)N1CCC[C@H]1Cn1nc(-c2ccc(Oc3ccccc3)cc2F)c2c(N)ncnc21)N1CCCC1]

Step 1

To a solution of 2-methylpropanal (5.6 mL, 61.8 mmol) in DCM (75 mL) cooled with an ice bath was added bromine (3.2 mL, 61.8 mmol) dropwise. After 1 hr, the solution was evaporated, stirred in DCM (8 ml) at room temperature and pyrrolidine (0.94 mL, 11.26 mmol) was added. After stirring 4 h, the mixture was diluted with brine and the layers separated. The organic layer was washed with 1M HCl and then the aqueous layer was basified with KOH to pH=10-11. This was then extracted with DCM and the organic layers were combined, dried (MgSO$_4$), filtered and concentrated to isolate 2-methyl-2-pyrrolidin-1-yl-propanal oil as an oil.

Step 2

To a mixture of (S)-3-(2-((4-amino-3-(2-fluoro-4-phenoxyphenyl)-1H-pyrazolo[3,4-d]pyrimidin-1-yl)methyl)pyrrolidin-1-yl)-3-oxopropanenitrile (285 mg, 0.60 mmol), 2-methyl-2-pyrrolidin-1-yl-propanal (719 mg, 5.1 mmol) and pyrrolidine (0.23 mL, 2.8 mmol) in DCM (6 mL) at room temperature was added chloro(trimethyl)silane (0.23 mL, 1.8 mmol). After stirring 90 min, the solution was diluted with sat. NaHCO$_3$ and extracted with DCM. The organic layers were combined, dried (MgSO$_4$), filtered and concentrated. The crude material was purified by Isolera (10 g column:0%-15% iPrOH/DCM) to obtain 270 mg of (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(pyrrolidin-1-yl)pent-2-enenitrile. MS (pos. ion) m/z: 595 (M+1).

Example 6

Synthesis of 2-((R)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile

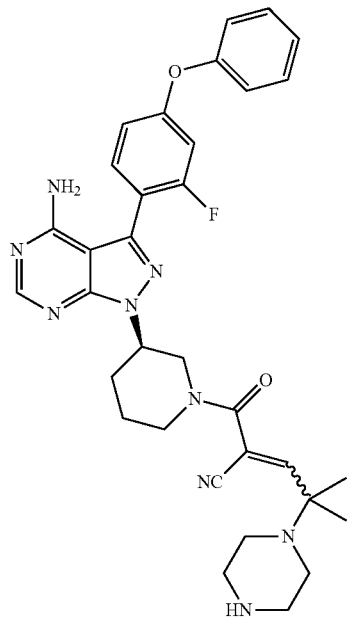 [SMILES: CC(C)(C=C(C#N)C(=O)N1CCC[C@@H](n2nc(-c3ccc(Oc4ccccc4)cc3F)c3c(N)ncnc32)C1)N1CCNCC1]

Step 1

Into a 250-mL round-bottom flask, was placed a solution of 2-bromo-2-methylpropanal (5 g, 33.11 mmol, 1.00 equiv) and tert-butyl piperazine-1-carboxylate (18.6 g, 99.87 mmol, 3.02 equiv) in ether (80 mL). The resulting solution was stirred overnight at 25° C. The solids were filtered out. The organic filtrate was washed with water, dried over anhydrous sodium sulfate and concentrated under vacuum to give 6 g of tert-butyl 4-(2-methyl-1-oxopropan-2-yl)piperazine-1-carboxylate as a white solid.

Step 2

Into a 100-mL round-bottom flask, was placed 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile (300 mg, 0.64 mmol, 1.00 equiv), piperidine (110 mg, 1.29 mmol, 2.03 equiv), toluene (30 mL) and tert-butyl 4-(2-methyl-1-oxopropan-2-yl)piperazine-1-carboxylate (820 mg, 3.20 mmol, 5.03 equiv). The resulting solution was heated to reflux overnight. The reaction was quenched by the addition of water. The resulting solution was extracted with ethyl acetate and the organic layers were combined, washed with brine, dried over anhydrous sodium sulfate, filtered and concentrated under vacuum. The residue was applied onto a silica gel column with ethyl acetate/petroleum ether (1:3 to 1:5). This resulted in 170 mg of (R)-tert-butyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate as yellow oil.

Step 3

Into a 30-mL round-bottom flask cooled to 0° C., was placed dichloromethane (8 mL), (R)-tert-butyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate (170 mg, 0.24 mmol, 1.00 equiv), and trifluoroacetic acid (2 mL). The resulting solution was stirred for 3 h at 25° C. The resulting mixture was concentrated under vacuum and the residue was dissolved in DCM. The resulting mixture was washed with 20 mL of aqueous potassium carbonate. The organic layer was dried over anhydrous sodium sulfate, concentrated to give the crude product. The crude product was purified by re-crystallization from ether. This resulted in 27 mg of 2-((R)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile as a light yellow solid. LCMS (ESI, pos. ion) m/z: 610 (M+1).

Example 7

Synthesis of 2-((R)-3-(4-amino-3-(2-fluoro-4-phenoxyphenyl)-1H-pyrazolo[3,4-d]pyrimidin-1-yl)piperidine-1-carbonyl)-4-(3-hydroxyazetidin-1-yl)-4-methylpent-2-enenitrile

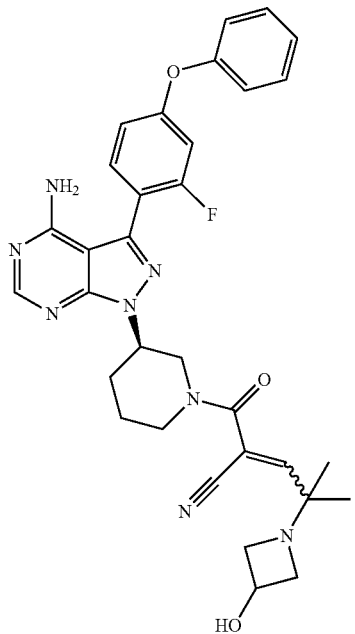 [SMILES: CC(C)(C=C(C#N)C(=O)N1CCC[C@@H](n2nc(-c3ccc(Oc4ccccc4)cc3F)c3c(N)ncnc32)C1)N1CC(O)C1]

Step 1

To a solution of azetidin-3-ol hydrochloride (5.11 g, 46.7 mmol, 1.0 equiv) and 1H-imidazole (9.52 g, 140 mmol, 3.0 equiv) in DCM (100 mL) at 0° C. was added TBDPSCl (19.18 g, 70 mmol, 1.5 equiv) dropwise. The resulting mixture was stirred at rt overnight and then diluted with water, and extracted with DCM. The combined organic layer was dried over anhydrous sodium sulfate, filtered and concentrated under vacuum. The crude product was eluted over a silica gel with DCM/McOH=100/1 to 10/1 to give 12 g of 3-(tert-butyldiphenylsilyloxy) azetidine as a colorless oil.

Step 2

To a solution of 2-bromo-2-methylpropanal (2.14 g, 14.3 mmol, 1.0 equiv) in Et$_2$O (150 mL) at 0° C. was added 3-(tert-butyldiphenylsilyloxy)azetidine (13.3 g, 42.9 mmol, 3.0 equiv) dropwise. The resulting mixture was stirred at 0° C. for 3 h. The mixture was diluted with water and then extracted with Et$_2$O. The combined organic layer was dried over anhydrous sodium sulfate, filtered and concentrated under vacuum. The crude product was applied onto a silica gel with petroleum ether/ethyl acetate=20/1 to 5/1. This resulted in 2.4 g (44%) of 2-(3-(tert-butyldiphenylsilyloxy)azetidin-1-yl)-2-methylpropanal as a colorless oil.

Step 3

To a solution of 3-((R)-3-(4-amino-3-(2-fluoro-4-phenoxyphenyl)-1H-pyrazolo[3,4-d]pyrimidin-1-yl)piperidin-1-yl)-3-oxopropanenitrile (471 mg, 1 mmol, 1.0 equiv), 2-(3-(tert-butyldiphenylsilyloxy)azetidin-1-yl)-2-methylpropanal (762 mg, 2 mmol, 2.0 equiv) and pyrrolidine (284 mg, 4 mmol, 4.0 equiv) in DCM (20 mL) was added dropwise chlorotrimethylsilane (216 mg, 2 mmol, 2.0 equiv). The resulting mixture was stirred at rt overnight. The mixture was concentrated and the crude product was purified by column chromatography using ethyl acetate/MeOH=(100/1 to 20/1). This resulted in 0.3 g (36%) of 2-((R)-3-(4-amino-3-(2-fluoro-4-phenoxyphenyl)-1H-pyrazolo[3,4-d]pyrimidin-1-yl) piperidine-1-carbonyl)-4-(3-(tert-butyldiphenylsilyloxy)azetidin-1-yl)-4-methylpent-2-enenitrile as a light yellow solid.

Step 4

To a solution of 2-((R)-3-(4-amino-3-(2-fluoro-4-phenoxyphenyl)-1H-pyrazolo[3,4-d]pyrimidin-1-yl)piperidine-1-carbonyl)-4-(3-(tert-butyldiphenylsilyloxy)azetidin-1-yl)-4-methylpent-2-enenitrile (300 mg, 0.36 mmol, 1.0 equiv) in THF (8 mL) was added a solution of 1 M TBAF in THF (0.432 mL, 0.432 mmoL). The resulting mixture was stirred at rt overnight. The mixture was concentrated and the crude product was purified by prep-HPLC eluting with CH$_3$CN/H$_2$O (0.05% TFA). The organic phase was removed under reduced pressure and the resulting aqueous solution was diluted with sat.Na$_2$CO$_3$ solution and extracted with DCM. The combined organic layer was washed with brine, dried over anhydrous sodium sulfate, filtered and concentrated under vacuum. This resulted in 18.1 mg of 2-((R)-3-(4-amino-3-(2-fluoro-4-phenoxyphenyl)-1H-pyrazolo[3,4-d]pyrimidin-1-yl)piperidine-1-carbonyl)-4-(3-hydroxyazetidin-1-yl)-4-methylpent-2-enenitrile as a white solid. LCMS (ESI, pos. ion) m/z: 597 (M+1).

Example 8

Synthesis of 2-[(2S)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile

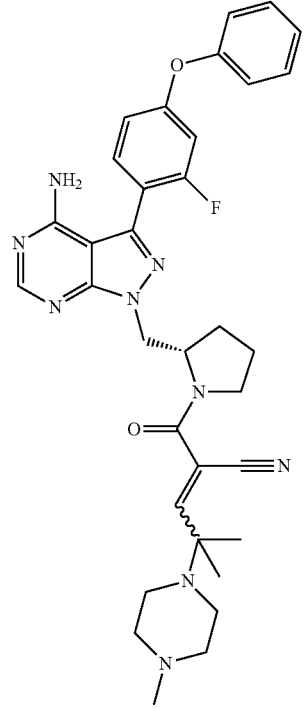 [SMILES: CN1CCN(C(C)(C)C=C(C#N)C(=O)N2CCC[C@H]2Cn2nc(-c3ccc(Oc4ccccc4)cc3F)c3c(N)ncnc32)CC1]

To a solution of 2-methyl-2-(4-methylpiperazin-1-yl)propanal (108.3 mg, 0.6400 mmol) in MeCN (6 mL), was added pyrrolidine (0.11 mL, 1.27 mmol). The reaction mixture was cooled to 0° C., followed by the addition TMS-Cl (0.11 mL, 0.85 mmol). The ice bath was removed and the mixture stirred for 10 min before adding 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (100 mg, 0.210 mmol). The mixture was stirred for 3 h at room temperature, checking progress by TLC and LC-MS. To the mixture was added 15 ml water and extracted with dichloromethane. The combined organic layer was washed by brine, dried over by $Na_2SO_4$, filtered, and evaporated. The residues was loaded on TLC plate and purified using MeOH:$CH_2Cl_2$=9:100 to get pure product 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(4-methylpiperazin-1-yl)pent-2-enenitrile (93 mg, 0.1491 mmol, 70.30 2% yield) as a light yellow powder. LC-MS (ES, m/z): 625 [M+H].

Example 8A

Proceeding as described above but substituting 2-methyl-2-(4-methylpiperazin-1-yl)propanal with 2-methyl-2-(4-ethylpiperazin-1-yl)propanal, 2-[(2S)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-ethylpiperazin-1-yl)pent-2-enenitrile was synthesized.

Example 9

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile

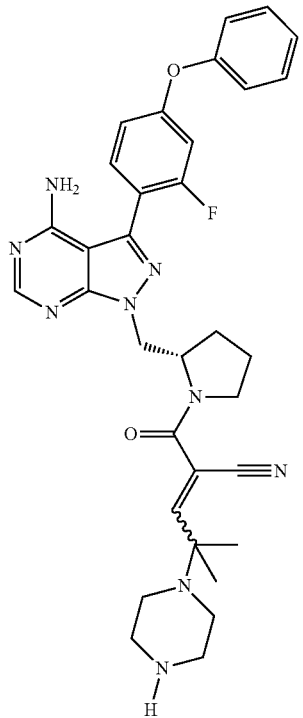 [SMILES: CC(C)(C=C(C#N)C(=O)N1CCC[C@H]1Cn1nc(-c2ccc(Oc3ccccc3)cc2F)c2c(N)ncnc21)N1CCNCC1]

Step 1
The 2-methylpropanal (1 mL, 10.96 mmol) was stirred in DCM (10 mL) while being cooled with an ice bath. Bromine (0.62 mL, 12.05 mmol) was slowly added via addition funnel over a 15 min period. After 1 hr of stirring at 0° C., the reaction was concentrated to a light yellow liquid. This was redissolved in DCM (10 mL) and cooled with an ice bath while the tert-butyl piperazine-1-carboxylate (2.04 g, 10.96 mmol) was slowly added (diluted with 5-10 mL, of DCM) over a 30 minute period. The cooling bath was removed and the reaction mixture was stirred at room temperature overnight, the mixture was washed with brine, then the remaining DCM layer was dried by $Na_2SO_4$, filtered and concentrated to collect tert-butyl 4-(1,1-dimethyl-2-oxo-ethyl)piperazine-1-carboxylate as a light yellow solid which was used directly without further purification.

Step 2

To a solution of tert-butyl 4-(1,1-dimethyl-2-oxo-ethyl)piperazine-1-carboxylate (326.2 mg, 1.27 mmol) in DCM (6 mL), was added pyrrolidine (0.17 mL, 2.04 mmol). The reaction mixture was cooled to 0° C., followed by the addition TMS-Cl (0.13 mL, 1.02 mmol). The ice bath was removed and the mixture stirred for 10 min before adding 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (120 mg, 0.250 mol). The mixture was stirred for 4 h at room temperature, at which point TLC and LC-MS showed the reaction was finished. To the mixture was added 30 ml water, the layers separated and the aq. layer was extracted with $CH_2Cl_2$. The combined organic layer was washed with brine, dried over $Na_2SO_4$, filtered, and the solvent removed in vacuo. The residue was dissolved in minimum $CH_2Cl_2$, loaded on a silica gel column and purified by MeOH/$CH_2Cl_2$ (¼): EtOAc 20-30% gradient to get pure product tert-butyl 4-[4-[(2S)-2-[[4-amino-3-(2-fluoro-4-phenoxy-phenyl)pyrazolo[3,4-d]pyrimidin-1-yl]methyl]pyrrolidin-1-yl]-3-cyano-1,1-dimethyl-4-oxo-but-2-enyl]piperazine-1-carboxylate as light yellow oil Step 3

To a solution of 4N HCl in dioxane (0.5 mL, 0.050 mmol) in THF (1mL) in the ice bath, was added tert-butyl 4-[4-[(2S)-2-[[4-amino-3-(2-fluoro-4-phenoxy-phenyl)pyrazolo[3,4-d]pyrimidin-1-yl]methyl]pyrrolidin-1-yl]-3-cyano-1,1-dimethyl-4-oxo-but-2-enyl]piperazine-1-carboxylate (32.9 mg, 0.050 mmol). The ice bath was removed, the reaction mixture was stirred for 4 h at room temperature at which point TLC and LC-MS showed the reaction was finished. The mixture was concentrated in vacuo, adjusted with $NaHCO_3$ to pH 6-7, and the aq. layer extracted with $CH_2Cl_2$. The combined organic layer was washed by brine, dried over $Na_2SO_4$, filtered, and the solvent removed to get product 2-[(2S)-2-[[4-amino-3-(2-fluoro-4-phenoxy-phenyl)pyrazolo[3,4-d]pyrimidin-1-yl]methyl]-pyrrolidine-1-carbonyl]-4-methyl-4-piperazin-1-yl-pent-2-enenitrile (24 mg, 0.039 mmol, 85% yield) as an off white powder. LC-MS (ES, m/z): 610 [M+H]

Example 10

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile

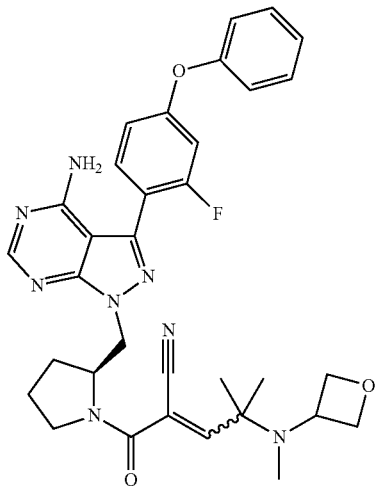 [SMILES: CN(C1COC1)C(C)(C)C=C(C#N)C(=O)N1CCC[C@H]1Cn1nc(-c2ccc(Oc3ccccc3)cc2F)c2c(N)ncnc21]

Step 1

The 2-methylpropanal (0.5 mL, 5.48 mmol) was stirred in DCM (10 mL) while being cooled with an ice bath. Bromine (0.31 mL, 6.03 mmol) was slowly added via addition funnel over a 15 min period. After 1 h of stirring at 0° C., the reaction was concentrated to a light yellow liquid. This was redissolved in DCM (5 mL) and cooled with an ice bath while the N-methyloxetan-3-amine (0.49 mL, 5.48 mmol) was slowly added (diluted with 5-10 mL of DCM) over a 10 minute period. Then the cooling bath was removed and the reaction mixture was stirred at room temperature overnight. The mixture was washed with brine, then the remaining DCM layer was washed by 0.5N HCl. The combined aq. layer was adjusted with KOH to pH 10-11, extracted with CH$_2$Cl$_2$, and the combined organic layer was washed with brine and dried by Na$_2$SO$_4$, filtered and concentrated to collect 2-methyl-2-[methyl(oxetan-3-yl)amino]propanal as a light yellow liquid. The crude material was used in the next step directly without further purification.

Step 2

To a solution of 2-methyl-2-[methyl(oxetan-3-yl)amino]propanal (100.0 mg, 0.6400 mmol) in DCM (5 mL), was added pyrrolidine (0.06 mL, 0.760 mmol). The reaction mixture was cooled to 0° C., followed by addition of TMS-Cl (0.06 mL, 0.51 mmol, the ice bath was removed and reaction mixture was stirred for 10 minutes before adding 3-[(2S)-2-[[4-amino-3-(2-fluoro-4-phenoxy-phenyl)pyrazolo[3,4-d]pyrimidin-1-yl]methyl]pyrrolidin-1-yl]-3-oxopropanenitrile (60 mg, 0.13 mmol). The mixture was stirred for 50 minutes and the reaction was deemed finished by checking progress through TLC and LC-MS. The reaction mixture was washed by 15 ml Sat.Na$_2$HCO$_3$ and the layers separated. The aq. layer was extracted with CH$_2$Cl$_2$ and the combined organic layer was washed with brine, dried over Na$_2$SO$_4$, filtered, and the solvent removed. The residue was loaded on silica gel column and purified by [MeOH:CH$_2$Cl$_2$ (1:4)]: EtOAc 20%, 30% to get pure product 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile (61.8 mg, 0.1012 mmol, 79.5% yield) as off white solid. LC-MS (ES, m/z): 612 [M+H]

Example 10a

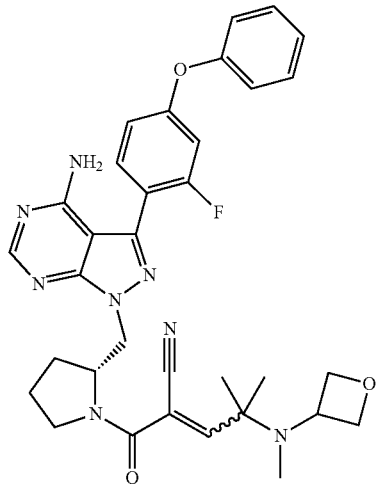 [SMILES: CN(C1COC1)C(C)(C)C=C(C#N)C(=O)N1CCC[C@@H]1Cn1nc(-c2ccc(Oc3ccccc3)cc2F)c2c(N)ncnc21]

Proceeding as described above but substituting (R)-3-(2-((4-amino-3-(2-fluoro-4-phenoxyphenyl)-1H-pyrazolo[3,4-d]pyrimidin-1-yl)methyl)pyrrolidin-1-yl)-3-oxopropanenitrile for (S)-3-(2-((4-amino-3-(2-fluoro-4-phenoxyphenyl)-1H-pyrazolo[3,4-d]pyrimidin-1-yl)methyl)pyrrolidin-1-yl)-3-oxopropanenitrile, (R)-2-(2-((4-amino-3-(2-fluoro-4-phenoxyphenyl)-1H-pyrazolo[3,4-d]pyrimidin-1-yl)methyl)pyrrolidine-1-carbonyl)-4-(methyl(oxetan-3-yl)amino)-4-methylpent-2-enenitrile was obtained. LC-MS (ES, m/z): 612 [M+H]

Example 10b (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile

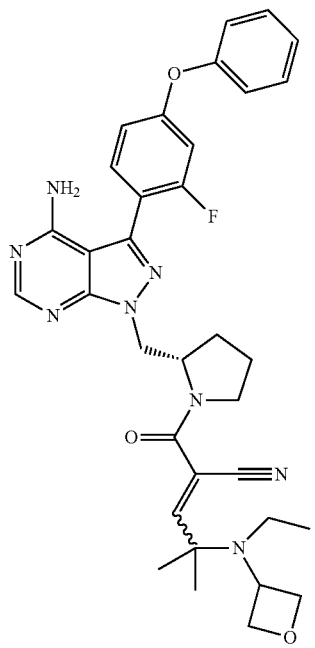 [SMILES: CCN(C1COC1)C(C)(C)C=C(C#N)C(=O)N1CCC[C@H]1Cn1nc(-c2ccc(Oc3ccccc3)cc2F)c2c(N)ncnc21]

Proceeding as described above but substituting N-ethyl-oxetane-3-amine for N-methyloxetan-3-amine. (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile was obtained. LC-MS (ES, m/z): 626 [M+H]

Example 11

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile

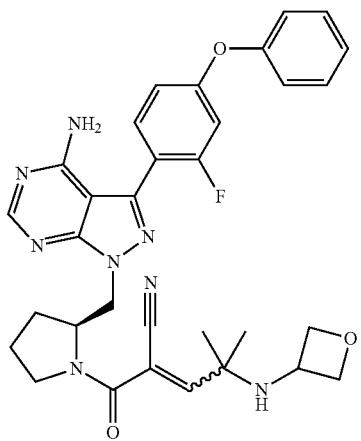 [SMILES: CC(C)(C=C(C#N)C(=O)N1CCC[C@H]1Cn1nc(-c2ccc(Oc3ccccc3)cc2F)c2c(N)ncnc21)NC1COC1]

Step 1

2-Methylpropanal (0.5 mL, 5.48 mmol) was stirred in DCM (10 mL) while being cooled with an ice bath. Bromine (0.31 mL, 6.03 mmol) was slowly added via addition funnel over a 15 min period. After 1 h of stirring at 0° C., the reaction was concentrated to a light yellow liquid. This was redissolved in DCM (5 mL) cooled with an ice bath while the oxetan-3-amine (0.39 mL, 5.48 mmol) was slowly added (diluted with 5-10 mL of DCM) over a 10 minute period, then the cooling bath was removed and the reaction mixture was stirred at room temperature overnight. The mixture was then washed with brine and the remaining DCM layer was washed by 0.5N HCl. The combined aq. layer was adjusted with KOH to pH 10-11, extracted with $CH_2Cl_2$, and the combined organic layer was washed with brine and dried over $Na_2SO_4$, filtered and concentrated to collect 2-methyl-2-(oxetan-3-ylamino)propanal as a light yellow liquid. The crude material was used in the next step directly without further purification.

Step 2

To a solution of 2-methyl-2-(oxetan-3-ylamino)propanal (106.3 mg, 0.7400 mmol) in DCM (5 mL) was added pyrrolidine (0.07 mL, 0.890 mmol). The reaction mixture was cooled to 0° C., followed by addition TMS-Cl (0.08 mL, 0.59 mmol). The ice bath was removed and the reaction mixture was stirred at room temperature for 10 minutes before adding 3-[(2S)-2-[[4-amino-3-(2-fluoro-4-phenoxyphenyl)pyrazolo[3,4-d]pyrimidin-1-yl]methyl]pyrrolidin-1-yl]-3-oxo-propanenitrile (70 mg, 0.1500 mmol). The mixture was stirred for 50 minutes at which point it was deemed finished by checking TLC and LC-MS. The mixture was washed with saturated $Na_2HCO_3$ and the layers separated. The aq. layer was extracted with $CH_2Cl_2$, and the combined organic layer was washed with brine, dried over $Na_2SO_4$, filtered, and the solvent removed. The residue was loaded on silica gel plate, flashed by [MeOH:$CH_2Cl_2$(1:4)]:EtOAc 50%, 60% to get pure product 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile (35.6 mg, 0.0597 mmol, 40.2% yield) as an off white solid. LC-MS (ES, m/z): 598 [M+H].

Example 11a

Synthesis of (R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(oxetan-3-ylamino)pent-2-enenitrile

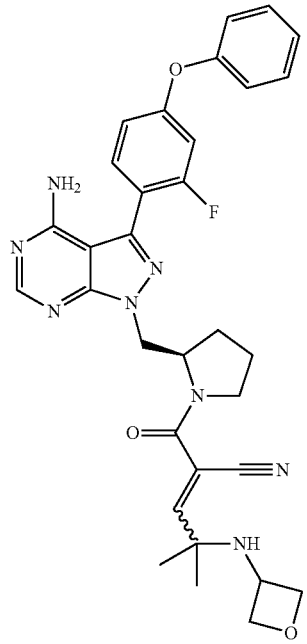 [SMILES: CC(C)(C=C(C#N)C(=O)N1CCC[C@@H]1Cn1nc(-c2ccc(Oc3ccccc3)cc2F)c2c(N)ncnc21)NC1COC1]

Proceeding as described above but substituting 3-[(2R)-2-[[4-amino-3-(2-fluoro-4-phenoxy-phenyl)pyrazolo[3,4-d]pyrimidin-1-yl]methyl]pyrrolidin-1-yl]-3-oxo-propanenitrile for 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile, (R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(oxetan-3-ylamino)pent-2-enenitrile was obtained. LC-MS (ES, m/z): 598 [M+H].

Example 12

Synthesis of 2-[2-[[4-amino-3-(2-fluoro-4-phenoxy-phenyl)pyrazolo[3,4-d]pyrimidin-1-yl]methyl]azetidine-1-carbonyl]-4-methyl-pent-2-enenitrile

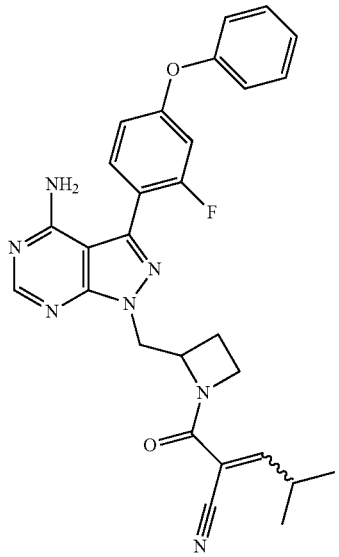 [SMILES: CC(C)C=C(C#N)C(=O)N1CCC1Cn1nc(-c2ccc(Oc3ccccc3)cc2F)c2c(N)ncnc21]

Step 1

To a mixture of 3-(2-fluoro-4-phenoxy-phenyl)-1H-pyrazolo[3,4-d]pyrimidin-4-amine (300 mg, 0.930 mmol), tert-butyl 2-(hydroxymethyl)azetidine-1-carboxylate (0.33 mL, 1.9 mmol) and PPh₃ (733.86 mg, 2.8 mmol) in THF (10 mL) in ice bath, the DIAD (0.37 mL, 1.87 mmol) as a solution in 5 ml THF was slowly added. The mixture was stirred at RT overnight and then the solvent was removed. To the residue was added H₂O and the mixture was extracted with EtOAc. The combined organic layer was washed with NaHCO₃, then brine, and dried over Na₂SO₄. The solvent was removed to get tert-butyl 2-[[4-amino-3-(2-fluoro-4-phenoxy-phenyl)pyrazolo[3,4-d]pyrimidin-1-yl]methyl]azetidine-1-carboxylate weighing 800 mg, which was used without further purification for the next step.

Step 2

To the crude tert-butyl 2-[[4-amino-3-(2-fluoro-4-phenoxy-phenyl)pyrazolo[3,4-d]pyrimidin-1-yl]methyl]azetidine-1-carboxylate (800 mg, 1.63 mmol) dissolved in DCM (4 mL) in ice bath, was dropwise added TFA (2 mL) slowly, stirring for 10 min at which point nostarting material remained by TLC analysis. The solvent was removed and EtOAc added, which was washed with 2M HCl. The combined aq. solution was adjusted with NaOH to pH around 10, and the aq. layer extracted with EtOAc. The combined organic layer was washed with brine, dried over Na₂SO₄, and the solvent removed to get 450 mg of 1-(azetidin-2-ylmethyl)-3-(2-fluoro-4-phenoxy-phenyl)pyrazolo[3,4-d]pyrimidin-4-amine, which was used in the next step directly without further purification.

Step 3

To a solution of 2-cyano-4-methyl-pent-2-enoic acid (30.7 mg, 0.220 mmol), 1-(azetidin-2-ylmethyl)-3-(2-fluoro-4-phenoxy-phenyl)pyrazolo[3,4-d]pyrimidin-4-amine (57.5 mg, 0.150 mmol in DCM (2 mL) was added PyAOP (86.2 mg, 0.160 mmol) and TEA (0.06 mL, 0.440 mmol) and the resulting yellow solution stirred at rt for 1 h. LCMS showed that the reaction was complete and the crude mixture was directly loaded onto a silica gel cartridge for purification (3 to 5% MeOH:CH₂Cl₂). Removal of solvent from cleanest fractions afforded 30 mg of the desired compound 2-[2-[[4-amino-3-(2-fluoro-4-phenoxy-phenyl)pyrazolo[3,4-d]pyrimidin-1-yl]methyl]azetidine-1-carbonyl]-4-methyl-pent-2-enenitrile (30 mg, 0.0586 mmol, 39.8% yield) as judged by LCMS. (M+I=512).

Example 13

Synthesis of 2-[(3R)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile

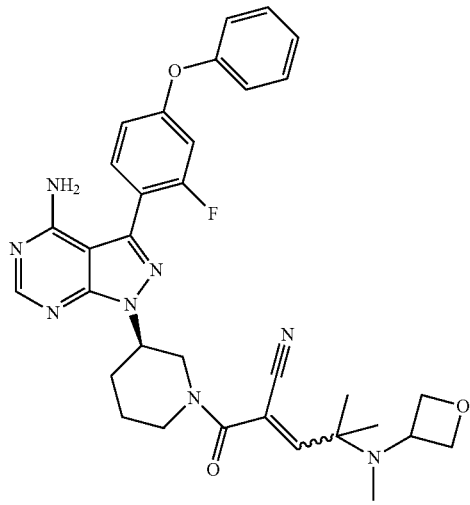 [SMILES: CN(C1COC1)C(C)(C)C=C(C#N)C(=O)N1CCC[C@@H](n2nc(-c3ccc(Oc4ccccc4)cc3F)c3c(N)ncnc32)C1]

The mixture of 2-methyl-2-[methyl(oxetan-3-yl)amino]propanal (66.69 mg, 0.42 mmol), 3-[(3R)-3-[4-amino-3-(2-fluoro-4-phenoxy-phenyl)pyrazolo[3,4-d]pyrimidin-1-yl]-1-piperidyl]-3-oxo-propanenitrile (100 mg, 0.2100 mmol) and pyrrolidine (0.1 mL, 1.27 mmol) was stirred at room temperature for 10 min. The reaction mixture was cooled to 0° C., followed by addition of TMS-Cl (0.11 mL, 0.85 mmol). The ice bath was removed and the reaction mixture was stirred for another 1 hour at room temperature, checking process by TLC and LC-MS. The solvent was removed and the resultant residue purified by column chromatography (MeOH, CH₂Cl₂, MeOH gradient from 0 to 10% to get 2-[(3R)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile (118.5 mg) as a white powder. LC-MS (ES, m/z): 612 [M+H]

Example 13a

Synthesis of (R)-2-(3-(4-amino-3-(2-fluoro-4-phenoxyphenyl)-1H-pyrazolo[3,4-d]pyrimidin-1-yl)piperidine-1-carbonyl)-4-(ethyl(oxetan-3-yl)amino)-4-methylpent-2-enenitrile

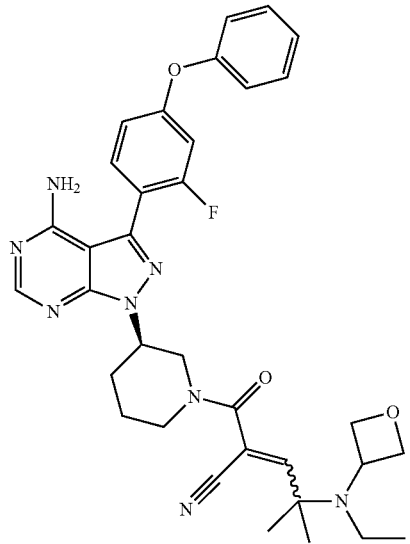 [SMILES: CCN(C1COC1)C(C)(C)C=C(C#N)C(=O)N1CCC[C@@H](n2nc(-c3ccc(Oc4ccccc4)cc3F)c3c(N)ncnc32)C1]

Proceeding as described above but substituting N-ethyl-oxetan-3-amine for N-methyloxetan-3-amine, (R)-2-(3-(4-amino-3-(2-fluoro-4-phenoxyphenyl)-1H-pyrazolo[3,4-d]pyrimidin-1-yl)piperidine-1-carbonyl)-4-(ethyl(oxetan-3-yl)amino)-4-methylpent-2-enenitrile was obtained. LC-MS (ES, m/z): 626 [M+H].

Example 13b

Synthesis of (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile

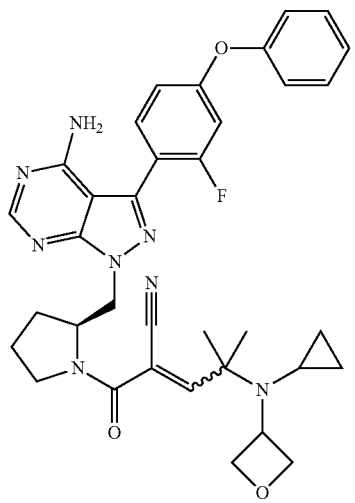 [SMILES: CC(C)(C=C(C#N)C(=O)N1CCC[C@H]1Cn1nc(-c2ccc(Oc3ccccc3)cc2F)c2c(N)ncnc21)N(C1CC1)C1COC1]

Proceeding as described in ex. 13 but substituting N-cyclopropyloxetan-3-amine for N-methyloxetan-3-amine, (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile was obtained. LC-MS (ES, m/z): 626 [M+H]

Example 14

Synthesis of 2-[3-[[4-amino-3-(2-fluoro-4-phenoxyphenyl)pyrazolo[3,4-d]pyrimidin-1-yl]methyl]azetidine-1-carbonyl]-4-methyl-pent-2-enenitrile

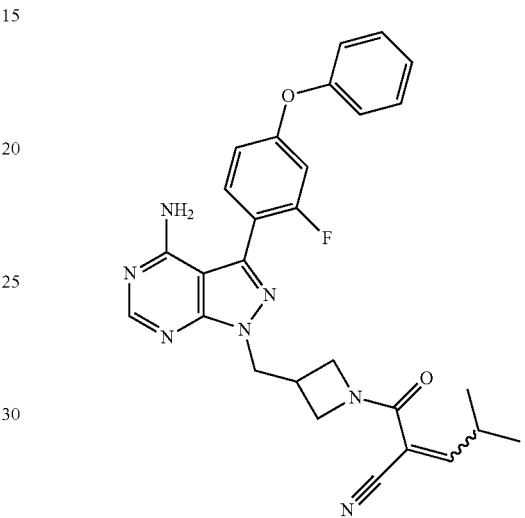

Step 1

The mixture of 3-(2-fluoro-4-phenoxy-phenyl)-1H-pyrazolo[3,4-d]pyrimidin-4-amine (500 mg, 1.56 mmol), PPh$_3$ (1.22 g, 4.67 mmol) and tert-butyl 3-(hydroxymethyl)azetidine-1-carboxylate (437 mg, 2.33 mmol) in THF (10 mL) was cooled in an ice bath and DIAD (0.61 mL, 3.11 mmol) in 5 ml THF was dropwise added to the reaction mixture. The mixture was stirred for 5 h. To the residue was added 30 ml water and the aq. layer extracted with EtOAc. The combined organic layer was washed with brine, dried over Na$_2$SO$_4$, filtered, the solvent removed, and the crude tert-butyl 3-[[4-amino-3-(2-fluoro-4-phenoxy-phenyl)pyrazolo[3,4-d]pyrimidin-1-yl]methyl]azetidine-1-carboxylate used in the next step directly.

Step 2 tert-Butyl 3-[[4-amino-3-(2-fluoro-4-phenoxy-phenyl)pyrazolo[3,4-d]pyrimidin-1-yl]methyl]azetidine-1-carboxylate (780 mg) in DCM (2 mL) was cooled in an ice bath. To this was added TFA (4 mL, 1.59 mmol), the ice bath was removed and the reaction mixture was stirred at room temperature for 1 hour, checking reaction by TLC and LC-MS. After two hours the solvent was removed, and to the residue was added water. The water layer was extracted with by EtOAc and the combined organic layer washed with 2N HCl. The combined aqueous layer was adjusted with NaOH to pH 9-10, extracted with EtOAc, and the combined organic layer washed with brine, dried over Na$_2$SO$_4$ and filtered. The solvent was removed to obtain 2-cyano-4-methyl-pent-2-enoic acid (48.12 mg, 0.350 mmol), 1-(azetidin-3-ylmethyl)-3-(2-fluoro-4-phenoxy-phenyl)pyrazolo[3,4-d]pyrimidin-4-amine which was used in the next step without further purification.

Step 3

To a solution of 2-cyano-4-methyl-pent-2-enoic acid (48.12 mg, 0.350 mmol), 1-(azetidin-3-ylmethyl)-3-(2-fluoro-4-phenoxy-phenyl)pyrazolo[3,4-d]pyrimidin-4-amine (90 mg, 0.230 mmol) in DCM (2 mL) was added PyAOP (134.9 mg, 0.250 mmol) and TEA (0.1 mL, 0.690 mmol) and the resulting yellow solution stirred at rt for 1 h. LCMS showed that the reaction was completed and the crude mixture was directly loaded onto a silica gel cartridge for purification (0.2 to 3% MeOH: $CH_2Cl_2$). Removal of solvent from cleanest fractions afforded 2-[3-[[4-amino-3-(2-fluoro-4-phenoxy-phenyl)pyrazolo[3,4-d]pyrimidin-1-yl]methyl]azetidine-1-carbonyl]-4-methyl-pent-2-enenitrile (12 mg LCMS. (M+1=512).

Example 15

Synthesis of 2-[2-[[4-amino-3-(2-fluoro-4-phenoxy-phenyl)pyrazolo[3,4-d]pyrimidin-1-yl]methyl]azetidine-1-carbonyl]-4-methyl-4-morpholino-pent-2-enenitrile

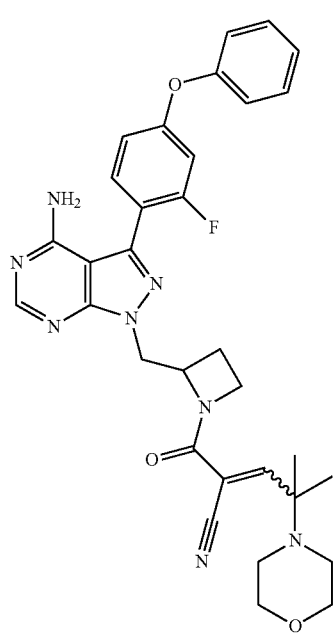 [SMILES: CC(C)(C=C(C#N)C(=O)N1CCC1Cn1nc(-c2ccc(Oc3ccccc3)cc2F)c2c(N)ncnc21)N1CCOCC1]

Step 1

To a mixture of 1-(azetidin-2-ylmethyl)-3-(2-fluoro-4-phenoxy-phenyl)pyrazolo[3,4-d]pyrimidin-4-amine (236.4 mg, 0.610 mmol), 2-cyanoacetic acid (77.2 mg, 0.910 mmol) in DCM (8 mL) in ice bath, was added T3P (0.36 mL, 1.21 mmol) and TEA (0.34 mL, 2.42 mmol). The ice bath was removed and the reaction mixture was stirred at room temperature overnight. The reaction mixture was loaded onto the silica gel column, purified with 0-3% gradient MeOH:$CH_2CL_2$, to get 3-[2-[[4-amino-3-(2-fluoro-4-phenoxy-phenyl)pyrazolo[3,4-d]pyrimidin-1-yl]methyl]azetidin-1-yl]-3-oxo-propanenitrile (201 mg) as yellow oil.

Step 2

To the mixture of 3-[2-[[4-amino-3-(2-fluoro-4-phenoxy-phenyl)pyrazolo[3,4-d]pyrimidin-1-yl]methyl]azetidin-1-yl]-3-oxo-propanenitrile (90.6 mg, 0.200 mmol), 2-methyl-2-morpholino-propanal (98.3 mg, 0.590 mmol) in DCM (2 mL) in an ice bath was added pyrrolidine (0.1 mL, 1.19 mmol) and TMS-Cl (0.1 mL, 0.79 mmol). The ice bath was removed and the reaction mixture was stirred at room temperature for 1 hour and the reaction mixture directly loaded on silica gel plate, purified by EtOH:$CH_2Cl_2$ 5% to get pure product 2-[2-[[4-amino-3-(2-fluoro-4-phenoxy-phenyl)pyrazolo[3,4-d]pyrimidin-1-yl]methyl]azetidine-1-carbonyl]-4-methyl-4-morpholino-pent-2-enenitrile (23 mg) as a white powder. LC-MS (ES, m/z): 597 [M+H]

Example 16

Synthesis of 2-[2-[[4-amino-3-(2-fluoro-4-phenoxy-phenyl)pyrazolo[3,4-d]pyrimidin-1-yl]methyl]azetidine-1-carbonyl]-4-methyl-4-(4-methylpiperazin-1-yl)pent-2-enenitrile

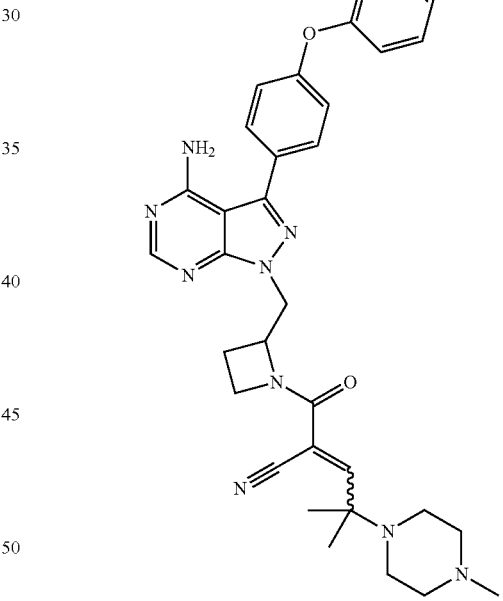

To a mixture of 3-[2-[[4-amino-3-(2-fluoro-4-phenoxy-phenyl)pyrazolo[3,4-d]pyrimidin-1-yl]methyl]azetidin-1-yl]-3-oxo-propanenitrile (100.6 mg, 0.220 mmol) and 2-methyl-2-(4-methylpiperazin-1-yl)propanal (118.2 mg, 0.660 mmol) in DCM (5 mL) in an ice bath was added pyrrolidine (0.11 mL, 1.32 mmol) and TMS-Cl (0.11 mL, 0.880 mmol). The ice bath was removed and the reaction mixture was stirred at room temperature for 1 hour. The crude reaction mixture was loaded on silica gel plate, purified by MeOH:$CH_2Cl_2$ to obtain 2-[2-[[4-amino-3-(2-fluoro-4-phenoxy-phenyl)pyrazolo[3,4-d]pyrimidin-1-yl]methyl]azetidine-1-carbonyl]-4-methyl-4-(4-methylpiperazin-1-yl)pent-2-enenitrile (19 mg) as a white powder. LC-MS (ES, m/z): 610 [M+H]

Example 17

Synthesis of 2-[3-[4-amino-3-(2-fluoro-4-phenoxy-phenyl)pyrazolo[3,4-d]pyrimidin-1-yl]azetidine-1-carbonyl]-4-methyl-pent-2-enenitrile

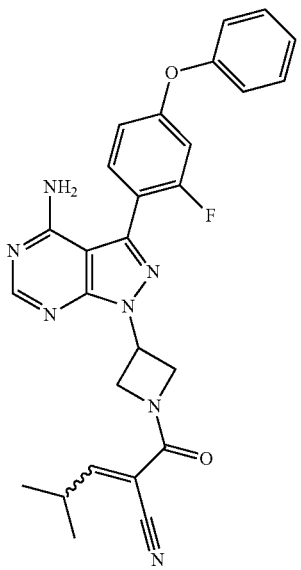 [SMILES: CC(C)C=C(C#N)C(=O)N1CC(n2nc(-c3ccc(Oc4ccccc4)cc3F)c3c(N)ncnc32)C1]

Step 1

A mixture of 3-iodo-1H-pyrazolo[3,4-d]pyrimidin-4-amine (3 g, 11.49 mmol), PPh3 (9.03 g, 34.5 mmol) tert-butyl 3-hydroxyazetidine-1-carboxylate (2.09 g, 12.1 mmol) in THF (60 mL) was cooled in an ice bath. DIAD (4.52 mL, 23.0 mmol) in 30 ml THF in dropping funnel was slowly added to the reaction mixture, and the reaction mixture was stirred for overnight. The solvent was removed and H₂O was added. The aq. layer was extracted with EtOAc and the combined organic layer was washed with brine, dried over Na₂SO₄, filtered, and the solvent removed to obtain tert-butyl 3-[3-iodo-4-[(triphenyl-{5}-phosphanylidene)amino]pyrazolo[3,4-d]pyrimidin-1-yl]azetidine-1-carboxylate which was used as is for the next step.

Step 2

The mixture of tert-butyl 3-[3-iodo-4-[(triphenyl-(5)-phosphanylidene)amino]-pyrazolo[3,4-d]pyrimidin-1-yl]azetidine-1-carboxylate (1.2 g, 1.77 mmol), (2-fluoro-4-phenoxy-phenyl)boronic acid (0.82 g, 3.55 mmol), Tetrakis(triphenylphosphane)palladium(0) (102.4 mg, 0.089 mmol) and K₂CO₃(514 mg, 3.73 mmol) in 1,4 dioxane (16 ml) and H2O (4 ml), was flushed with Ar₂ for 15 minutes. The reaction tube was sealed and heated in a microwave oven at 180° C. for 2 h, 15 min. The solvent was removed and water and EtOAc were added. The mixture was filtered through celite and separated. The aq. layer was extracted by EtOAc and the combined organic layer, washed with brine, dried over Na₂SO₄, filtered, and the solvent removed to obtain the crude tert-butyl 3-(4-amino-3-(2-fluoro-4-phenoxyphenyl)-1H-pyrazolo[3,4-d]pyrimidin-1-yl)azetidine-1-carboxylate (800 mg) which was used directly in the next step.

Step 3 tert-Butyl 3-(4-amino-3-(2-fluoro-4-phenoxyphenyl)-1H-pyrazolo[3,4-d]pyrimidin-1-yl)azetidine-1-carboxylate (800 mg) in TFA (8 mL) was stirred for 1 hour. To the residue was added EtOAc and 1 water and the layers were separated. The aqueous layer was extracted with EtOAc and the combined organic layer was evaporated to around 50 ml and washed with 2M HCl. The combined aqueous layer was adjusted with NaOH to pH 8-9, extracted with EtOAc and the combined organic layer washed with brine, and dried over Na₂SO₄. The solvent was removed to obtain 600 mg of 1-(azetidin-3-yl)-3-(2-fluoro-4-phenoxyphenyl)-1H-pyrazolo[3,4-d]pyrimidin-4-amine.

Step 4

The mixture of 1-(azetidin-3-yl)-3-(2-fluoro-4-phenoxyphenyl)pyrazolo[3,4-d]pyrimidin-4-amine (80 mg, 0.210 mmol, 2-cyano-4-methyl-pent-2-enoic acid (44.4 mg, 0.320 mmol), PyAOP (121.9 mg, 0.230 mmol) and TEA (0.09 mL, 0.640 mmol) in DCM (3 mL), were stirred overnight at room temperature. The solvent was removed and the residue was purified on a silica gel plate using 6:94 MeOH:CH₂Cl₂ to get 2-[3-[4-amino-3-(2-fluoro-4-phenoxy-phenyl)pyrazolo[3,4-d]pyrimidin-1-yl]azetidine-1-carbonyl]-4-methyl-pent-2-enenitrile (34 mg) as white powder. LC-MS (ES, m/z): 498 [M+H].

Example 18

Synthesis of (R)-2-(3-(4-amino-3-(2-fluoro-4-phenoxyphenyl)-1H-pyrazolo[3,4-d]pyrimidin-1-yl)piperidine-1-carbonyl)-4-(4-hydroxypiperidin-1-yl)-4-methylpent-2-enenitrile

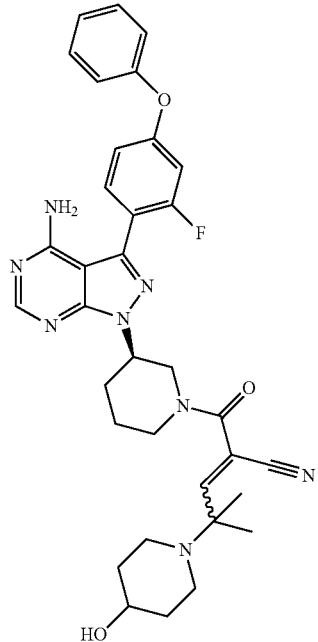 [SMILES: CC(C)(C=C(C#N)C(=O)N1CCC[C@@H](n2nc(-c3ccc(Oc4ccccc4)cc3F)c3c(N)ncnc32)C1)N1CCC(O)CC1]

Step 1

To a solution of 2-methylpropanal (0.82 mL, 9.0 mmol) in DCM (10 mL) cooled with an ice bath was added bromine (0.5 mL, 9.9 mmol) over a 10 min period. 1.5 hr later, the reaction was concentrated to a weight of 1.4 g, and then restirred in DCM (10 mL) at room temperature. To this, was added piperidin-4-ol (1.82 g, 18.0 mmol) dissolved in DCM (7 mL). The reaction was stirred overnight at room temperature and then diluted with DCM and washed with aq. NaHCO₃ and 0.5 N HCl. The aqueous acid layer was then adjusted to pH=12 with NaOH. A white ppt/oil formed and then the water layer was washed with DCM. The organic layer was dried (MgSO₄), filtered and concentrated to collect 0.49 g of 2-(4-hydroxypiperidin-1-yl)-2-methylpropanal as a yellow oil.

Step 2

A mixture of (R)-3-(3-(4-amino-3-(2-fluoro-4-phenoxyphenyl)-1H-pyrazolo[3,4-d]pyrimidin-1-yl)piperidin-1-yl)-3-oxopropanenitrile (150 mg, 0.31 mmol), 2-(4-hydroxy-1-piperidyl)-2-methyl-propanal (167 mg, 0.98 mmol), pyrrolidine (0.03 mL, 0.31 mmol) and DCM (10 mL) was stirred at room temp for 2 days and then diluted with aq. NaHCO₃ (40 mL) and extracted with DCM. The organic was dried (MgSO₄), filtered and concentrated to an oil. The crude material was purified at Isolera (25 g column: 30% iPrOH/DCM) to obtain the product which was isolated by lyophilization to provide 61 mg (32% yield) of (R)-2-(3-(4-amino-3-(2-fluoro-4-phenoxyphenyl)-1H-pyrazolo[3,4-d]pyrimidin-1-yl)piperidine-1-carbonyl)-4-(4-hydroxypiperidin-1-yl)-4-methylpent-2-enenitrile as a powder. MS (pos. ion) m/z: 625 (M+1).

Example 19

Synthesis of 2-[(3R)-3-[4-amino-3-(2-fluoro-4-phenoxy-phenyl)pyrazolo[3,4-d]pyrimidin-1-yl]piperidine-1-carbonyl]-4-methyl-4-(6-oxa-2-azaspiro[3.3]heptan-2-yl)pent-2-enenitrile

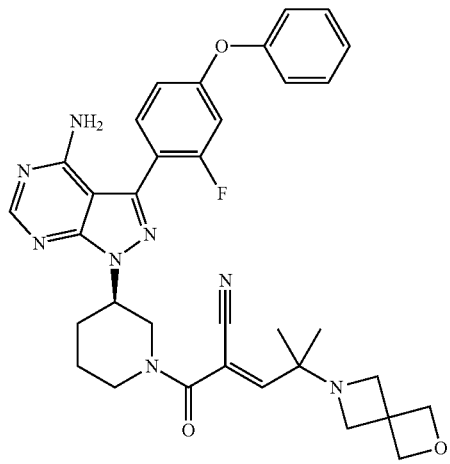 [SMILES: CC(C)(/C=C(\C#N)C(=O)N1CCC[C@@H](n2nc(-c3ccc(Oc4ccccc4)cc3F)c3c(N)ncnc32)C1)N1CC2(COC2)C1]

Step 1

To a solution of 2-methylpropanal (5.6 mL, 61.8 mmol) in DCM (75 mL) cooled with an ice bath was added bromine (3.2 mL, 61.8 mmol) dropwise. After 1 hr, the resulting 2-bromo-2-methylpropanal solution was evaporated to a weight of 8.5 g. This material was stirred in DCM (8 ml) at room temperature and 6-oxa-2-azaspiro[3.3]heptane; ½ oxalate (1.57 mL, 7.19 mmol) was added along with TEA (10 mL) and MeOH (3 mL). After stirring 2 days, the mixture was diluted with brine (30 mL) and the layers separated. The organic layer was washed with 1M HCl (50 mL) and then the aqueous layer was basified with KOH to pH=10-11. This was then extracted with DCM and the organic layers were combined, dried (MgSO₄), filtered and concentrated to isolate 2-methyl-2-(6-oxa-2-azaspiro[3.3]heptan-2-yl)propanal as an oil used directly in the next step.

Step 2:

To a mixture of (R)-3-(3-(4-amino-3-(2-fluoro-4-phenoxyphenyl)-1H-pyrazolo[3,4-d]pyrimidin-1-yl)piperidin-1-yl)-3-oxopropanenitrile (222 mg, 0.46 mmol), 2-methyl-2-(6-oxa-2-azaspiro[3.3]heptan-2-yl)propanal (231.17 mg, 1.37 mmol) and pyrrolidine (0.23 mL, 2.73 mmol) in DCM (10 mL) at room temperature was added chloro(trimethyl)silane (0.17 mL, 1.37 mmol). After stirring 2 h, the solution was diluted with sat. NaHCO₃ and extracted with DCM. The organic layers were combined, dried (MgSO₄), filtered and concentrated. The crude material was purified by chromatography to obtain 133 mg of 2-[(3R)-3-[4-amino-3-(2-fluoro-4-phenoxy-phenyl)pyrazolo[3,4-d]pyrimidin-1-ylpiperidine-1-carbonyl]-4-methyl-4-(6-oxa-2-azaspiro[3.3]heptan-2-yl)pent-2-enenitrile. MS (pos. ion) m/z: 623 (M+1).

Example 19a

Synthesis of (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(2-oxa-6-azaspiro[3.3]heptan-6-yl)pent-2-enenitrile

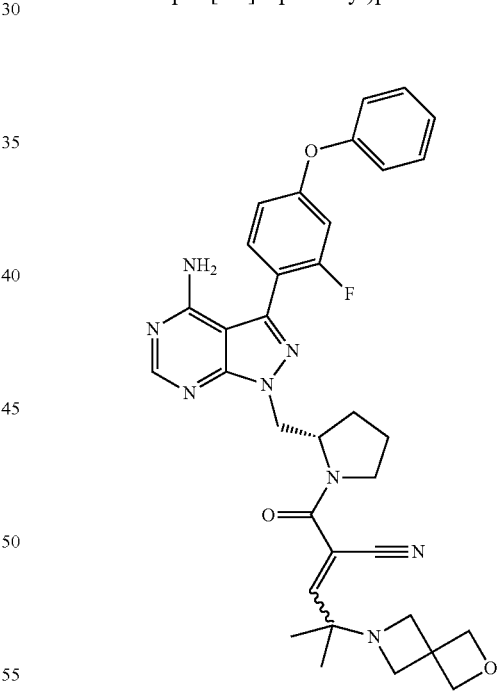

Proceeding as described above but substituting (S)-3-(2-((4-amino-3-(2-fluoro-4-phenoxyphenyl)-1H-pyrazolo[3,4-d]pyrimidin-1-yl)methyl)pyrrolidin-1-yl)-3-oxopropanenitrile for (R)-3-(3-(4-amino-3-(2-fluoro-4-phenoxyphenyl)-1H-pyrazolo[3,4-d]pyrimidin-1-yl)piperidin-1-yl)-3-oxopropanenitrile afforded 2-[(2S)-2-[[4-amino-3-(2-fluoro-4-phenoxy-phenyl)pyrazolo[34-d]pyrimidin-1-yl]methyl]piperidine-1-carbonyl]-4-methyl-4-(6-oxa-2-azaspiro[3.3]heptan-2-yl)pent-2-enenitrile. MS (pos. ion) m/z: 623 (M+1).

Example 20

Synthesis of 2-[(3R)-3-[4-amino-3-(2-fluoro-4-phenoxy-phenyl)pyrazolo[3,4-d]-pyrimidin-1-yl]piperidine-1-carbonyl]-4-(4-ethylpiperazin-1-yl)-4-methylpent-2-enenitrile

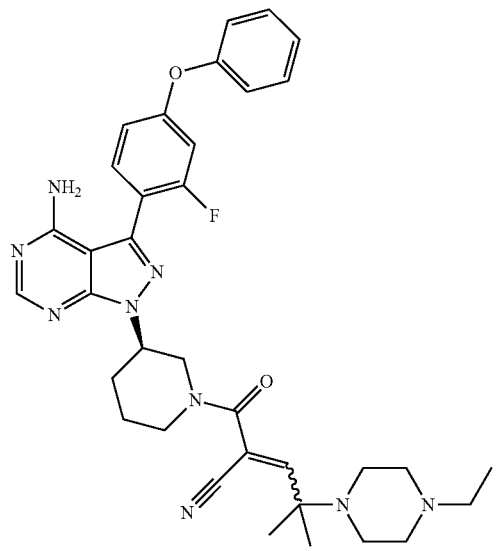 [SMILES: CCN1CCN(C(C)(C)C=C(C#N)C(=O)N2CCC[C@@H](n3nc(-c4ccc(Oc5ccccc5)cc4F)c4c(N)ncnc43)C2)CC1]

Step 1

To a cooled (0° C.) solution of 2-bromo-2-methyl-propanal (2504 mg, 16.58 mmol), prepared as in Example 5, in 15 mL of DCM was added 1-ethylpiperazine (2.53 mL, 19.9 mmol) and TEA (2.31 mL, 16.58 mmol) and the solution stirred at rt for 24 hours. The mixture was worked up with 1N HCl (50 mL) and DCM (50 mL×2). The aqueous was basified with KOH to pH~11 and washed with DCM (50 mL×3). The organic layers were washed with saturated sodium chloride, dried (MgSO4), and then concentrated to obtain 2-(4-ethylpiperazin-1-yl)-2-methyl-propanal (90% yield) as an oil.

Step 2

To the solution of 3-[(3R)-3-[4-amino-3-(2-fluoro-4-phenoxy-phenyl)pyrazolo[3,4-d]pyrimidin-1-yl]-1-piperidyl]-3-oxo-propanenitrile (0.32 mL, 0.57 mmol DCM (20 mL), 2-(4-ethylpiperazin-1-yl)-2-methyl-propanal (211.84 mg, 1.15 mmol) and pyrrolidine (0.14 mL, 1.72 mmol) was stirred at room temperature for 10 minutes then added chloro(trimethyl)silane (0.29 mL, 2.3 mmol). The mixture was allowed to stirred at room temperature for 18 h. The mixture was worked up with saturated NaHCO₃ (50 mL) and DCM (50 mL×2), washed with saturated sodium chloride, dried (MgSO4) and concentrated to yield an oil which was purified over silica gel (5%-50% iPA/DCM) to obtain 2-[(3R)-3-[4-amino-3-(2-fluoro-4-phenoxy-phenyl)pyrazolo[3,4-d]pyrimidin-1-yl]piperidine-1-carbonyl]-4-(4-ethylpiperazin-1-yl)-4-methyl-pent-2-enenitrile 265 mg (72.3% yield). MS (pos. ion) m/z: 638 (M+1).

Example 21

Synthesis of (R)-2-(3-(4-amino-3-(2-fluoro-4-phenoxyphenyl)-1H-pyrazolo[3,4-d]pyrimidin-1-yl) piperidine-1-carbonyl)-4-(4-isopropylpiperazin-1-yl)-4-methylpent-2-enenitrile

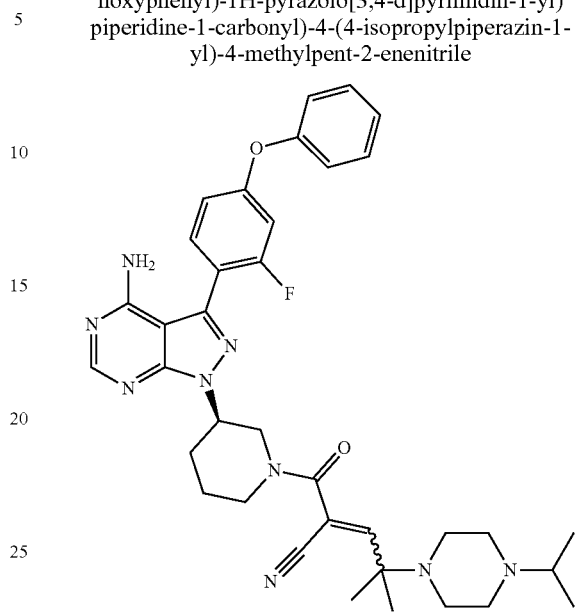

Proceeding as above in example 20 but substituting 1-isopropylpiperazine for 1-ethylpiperazine in step 1, (R)-2-(3-(4-amino-3-(2-fluoro-4-phenoxyphenyl)-1H-pyrazolo [3,4-d]pyrimidin-1-yl)piperidine-1-carbonyl)-4-(4-isopropylpiperazin-1-yl)-4-methylpent-2-enenitrile. MS (pos. ion) m/z: 653 (M+1).

Example 22

Synthesis of (R)-2-(3-(4-amino-3-(2-fluoro-4-phenoxyphenyl)-1H-pyrazolo[3,4-d]pyrimidin-1-yl) piperidine-1-carbonyl)-4-(4-(tert-butyl)piperazin-1-yl)-4-methylpent-2-enenitrile

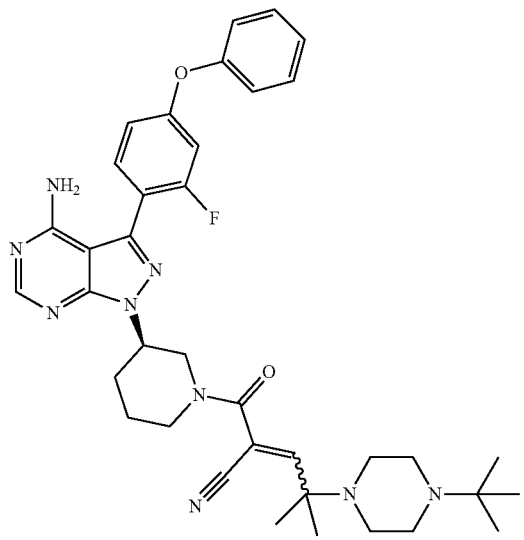 [SMILES: CC(C)(C)N1CCN(C(C)(C)C=C(C#N)C(=O)N2CCC[C@@H](n3nc(-c4ccc(Oc5ccccc5)cc4F)c4c(N)ncnc43)C2)CC1]

Proceeding as above in example 20 but substituting 1-(tert-butyl)piperazine for 1-ethylpiperazine in step 1, (R)-2-(3-(4-amino-3-(2-fluoro-4-phenoxyphenyl)-1H-pyrazolo [3,4-d]pyrimidin-1-yl)piperidine-1-carbonyl)-4-(4-(tert-butyl)piperazin-1-yl)-4-methylpent-2-enenitrile is obtained. MS (pos. ion) m/z: 668 (M+1).

Example 23

Synthesis of (R)-2-(3-(4-amino-3-(2-fluoro-4-phenoxyphenyl)-1H-pyrazolo[3,4-d]pyrimidin-1-yl)piperidine-1-carbonyl)-4-(4-(2-methoxyethyl)piperazin-1-yl)-4-methylpent-2-enenitrile

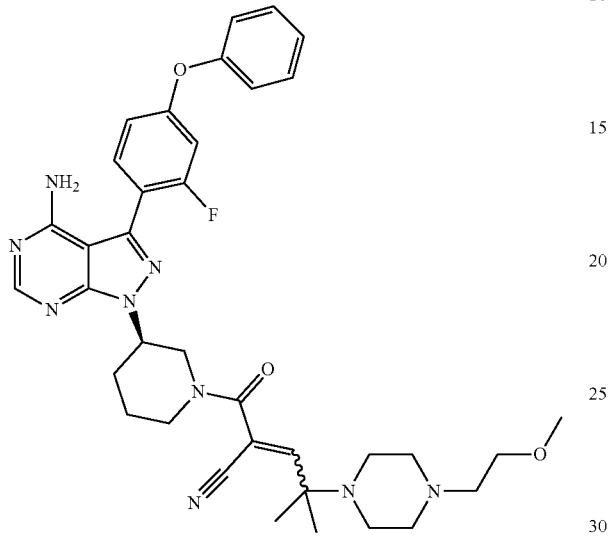

Proceeding as above in example 20 but substituting 1-(2-methoxyethyl)piperazine for 1-ethylpiperazine in step 1, (R)-2-(3-(4-amino-3-(2-fluoro-4-phenoxyphenyl)-1H-pyrazolo[3,4-d]pyrimidin-1-yl)piperidine-1-carbonyl)-4-(4-(2-methoxyethyl)piperazin-1-yl)-4-methylpent-2-enenitrile is obtained. MS (pos. ion) m/z: 668 (M+1).

Example 24

Synthesis of (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-methyl-3-oxopiperazin-1-yl)pent-2-enenitrile

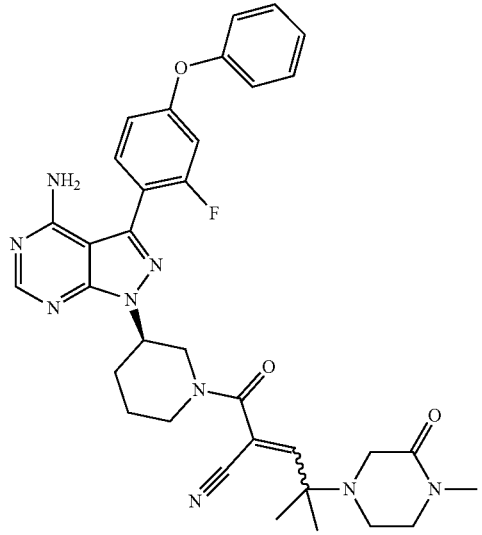 [SMILES: CN1CCN(C(C)(C)C=C(C#N)C(=O)N2CCC[C@@H](n3nc(-c4ccc(Oc5ccccc5)cc4F)c4c(N)ncnc43)C2)CC1=O]

Proceeding as above in example 20 but substituting 1-methylpiperazin-2-one for 1-ethylpiperazine in step 1, (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-methyl-3-oxopiperazin-1-yl)pent-2-enenitrile is obtained. MS (pos. ion) m/z: 638 (M+1).

Example 25

Synthesis of (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(methylsulfonyl)piperazin-1-yl)pent-2-enenitrile

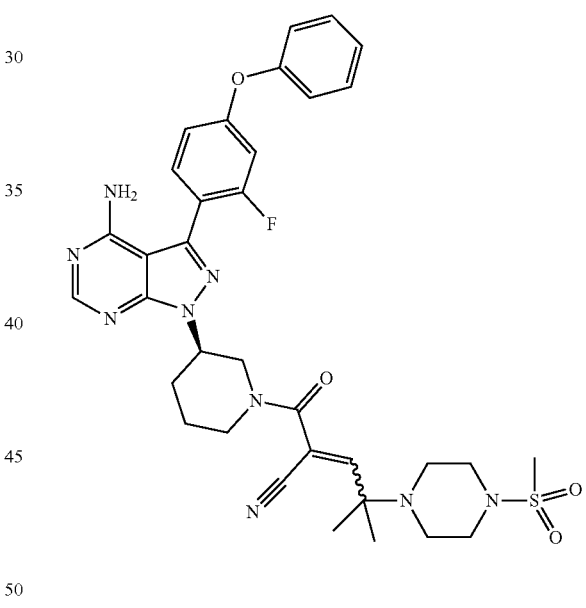

Proceeding as above in example 20 but substituting 1-(methylsulfonyl)piperazine for 1-ethylpiperazine in step 1, (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(methylsulfonyl)-piperazin-1-yl)pent-2-enenitrile is obtained. MS (pos. ion) m/z: 688 (M+1).

Example 26

Synthesis of (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(2,2,2-trifluoroethyl)piperazin-1-yl)pent-2-enenitrile

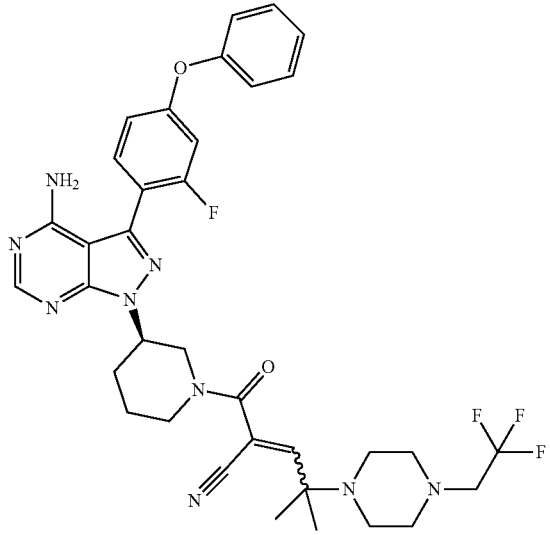 [SMILES: CC(C)(C=C(C#N)C(=O)N1CCC[C@@H](n2nc(-c3ccc(Oc4ccccc4)cc3F)c3c(N)ncnc32)C1)N1CCN(CC(F)(F)F)CC1]

Proceeding as above in example 20 but substituting 1-methyl-4-(2,2,2-trifluoroethyl)piperazine for 1-ethylpiperazine in step 1, (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(2,2,2-trifluoroethyl)piperazin-1-yl)pent-2-enenitrile is obtained. MS (pos. ion) m/z: 692 (M+1).

Example 27

Synthesis of 2-((R)-3-(4-amino-3-(2-fluoro-4-phenoxyphenyl)-1H-pyrazolo[3,4-d]pyrimidin-1-yl)piperidine-1-carbonyl)-4-methyl-4-((3S,5R)-3,4,5-trimethylpiperazin-1-yl)pent-2-enenitrile

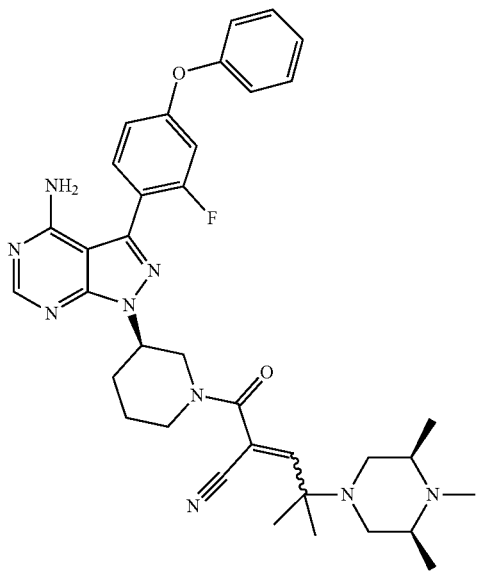 [SMILES: C[C@@H]1CN(C(C)(C)C=C(C#N)C(=O)N2CCC[C@@H](n3nc(-c4ccc(Oc5ccccc5)cc4F)c4c(N)ncnc43)C2)C[C@H](C)N1C]

Proceeding as above in example 20 but substituting (2S,6R)-1,2,6-trimethylpiperazine for 1-ethylpiperazine in step 1, 2-((R)-3-(4-amino-3-(2-fluoro-4-phenoxyphenyl)-1H-pyrazolo[3,4-d]pyrimidin-1-yl)piperidine-1-carbonyl)-4-methyl-4-((3S,5R)-3,4,5-trimethylpiperazin-1-yl)pent-2-enenitrile is obtained. MS (pos. ion) m/z: 652 (M+1).

Example 28

Synthesis of 2-((R)-3-(4-amino-3-(2-fluoro-4-phenoxyphenyl)-1H-pyrazolo[3,4-d]pyrimidin-1-yl)piperidine-1-carbonyl)-4-((3S,5R)-3,5-dimethylpiperazin-1-yl)-4-methylpent-2-enenitrile

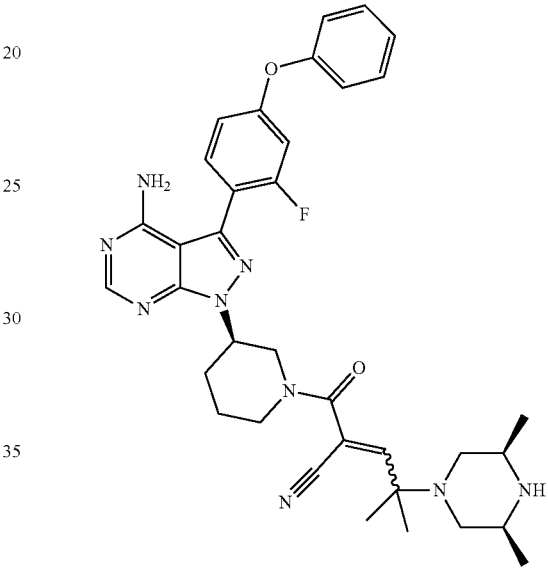

Steps 1 and 2 Proceeding as above in example 20 but substituting (2S,6R)-tert-butyl 2,6-dimethylpiperazine-1-carboxylate for 1-ethylpiperazine in step 1, (2S,6R)-tert-butyl 4-(5-((R)-3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)-2,6-dimethylpiperazine-1-carboxylate is obtained.

Step 3

The (2S,6R)-tert-butyl 4-(5-((R)-3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)-2,6-dimethylpiperazine-1-carboxylate (103.5 mg, 0.1400 mmol) was dissolved in 4N HCl in dioxane, and stirred at rt for 3 hours. The solvent was removed and 2 mL of MeOH was added to the residues. The mixture was neutralized to pH around 7-8 and extracted with DCM. The combined organic layer was washed with brine, dried over sodium sulfate, filtered, and the solvent evaporated to get pure product 2-((R)-3-(4-amino-3-(2-fluoro-4-phenoxyphenyl)-1H-pyrazolo[3,4-d]pyrimidin-1-yl)piperidine-1-carbonyl)-4-((3S,5R)-3,5-dimethylpiperazin-1-yl)-4-methylpent-2-enenitrile as a white solid. MS (pos. ion) m/z: 638 (M+1).

Example 29

Synthesis of (R)-2-(3-(4-amino-3-(2-fluoro-4-phenoxyphenyl)-1H-pyrazolo[3,4-d]pyrimidin-1-yl)piperidine-1-carbonyl)-4-(5,6-dihydroimidazo[1,2-a]pyrazin-7(8H)-yl)-4-methylpent-2-enenitrile

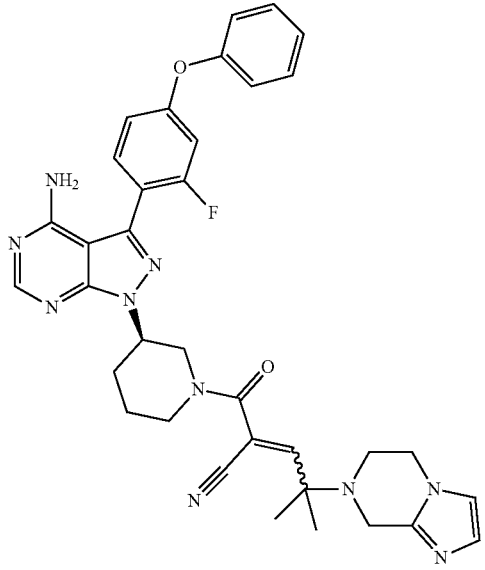 [SMILES: CC(C)(C=C(C#N)C(=O)N1CCC[C@@H](n2nc(-c3ccc(Oc4ccccc4)cc3F)c3c(N)ncnc32)C1)N1CCn2ccnc2C1]

Proceeding as above in example 20 but substituting 5,6,7,8-tetrahydroimidazo[1,2-a]pyrazine for 1-ethylpiperazine in step 1, (R)-2-(3-(4-amino-3-(2-fluoro-4-phenoxyphenyl)-1H-pyrazolo[3,4-d]pyrimidin-1-yl)piperidine-1-carbonyl)-4-(5,6-dihydroimidazo[1,2-a]pyrazin-7(8H)-yl)-4-methylpent-2-enenitrile is obtained. MS (pos. ion) m/z: 647 (M+1).

Example 30

Synthesis of (S)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethyl-5-morpholinopent-2-enenitrile

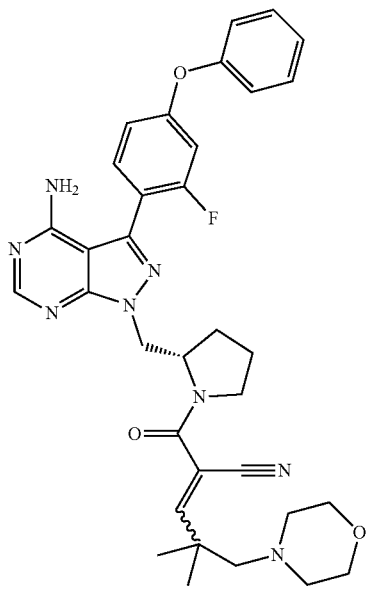 [SMILES: CC(C)(C=C(C#N)C(=O)N1CCC[C@H]1Cn1nc(-c2ccc(Oc3ccccc3)cc2F)c2c(N)ncnc21)CN1CCOCC1]

Proceeding as in Example 5, step 2, but substituting 2,2-dimethyl-3-morpholino-propanal for 2-methyl-2-(pyrrolidin-1-yl)propanal affords (S)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethyl-5-morpholinopent-2-enenitrile. MS (pos. ion) m/z: 625 (M+1).

Example 31

Synthesis of (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile

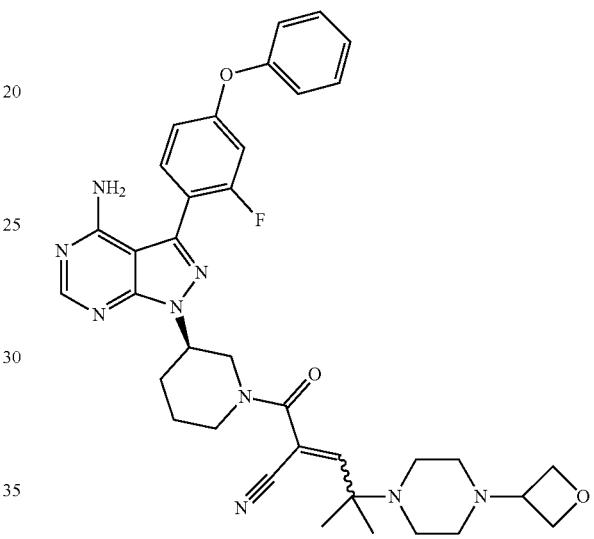

Step 1

A solution of 2-bromo-2-methyl-propanal (696.6 mg, 4.61 mmol) in DCM (10 mL) was cooled with an ice bath and 1-(oxetan-3-yl)piperazine (328 mg, 2.31 mmol), diluted with 5-10 mL of DCM, was slowly added via addition funnel over a 15 min period. Next, Hunig's base (0.4 mL, 2.31 mmol) was added and then the cooling bath was removed. The reaction mixture was stirred at room temperature overnight and the DCM layer was washed three times with 0.5N HCl. The combined aqueous layer was neutralized with NaOH to pH 10-11 and extracted with DCM. The combined organic layer was washed with brine and dried over $Na_2SO_4$. Filtration and removal of solvent afforded 2-methyl-2-[4-(oxetan-3-yl)piperazin-1-yl]propanal as a light yellow liquid, which was used directly in the next step without further purification.

Step 2

To a cooled (0° C.) solution of 3-[(3R)-3-[4-amino-3-(2-fluoro-4-phenoxy-phenyl)-pyrazolo[3,4-d]pyrimidin-1-yl]-1-piperidyl]-3-oxo-propanenitrile (80 mg, 0.17 mmol), was added 2-methyl-2-[4-(oxetan-3-yl)piperazin-1-yl]propanal (~108 mg, 0.51 mmol) in DCM (10 mL) followed by pyrrolidine (0.08 mL, 1.02 mmol) and TMS-Cl (0.09 mL, 0.68 mmol.) The ice bath was removed, and the reaction stirred 1 hour. Most of the solvent was removed and the residues were purified by chromatography, using 95:5 $CH_2Cl_2$:MeOH to obtain 79 mg of (R)-2-(3-(4-amino-3-(2-fluoro-4-phenoxyphenyl)-1H-pyrazolo[3,4-d]-pyrimidin-1- yl)piperidine-1-carbonyl)-4-methyl-4-(4-(oxetan-3-yl)piperazin-1-yl)pent-2-enenitrile as a white solid. MS (pos. ion) m/z: 666 (M+1).

Example 32

Synthesis of (R)-4-(4-acetylpiperazin-1-yl)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile

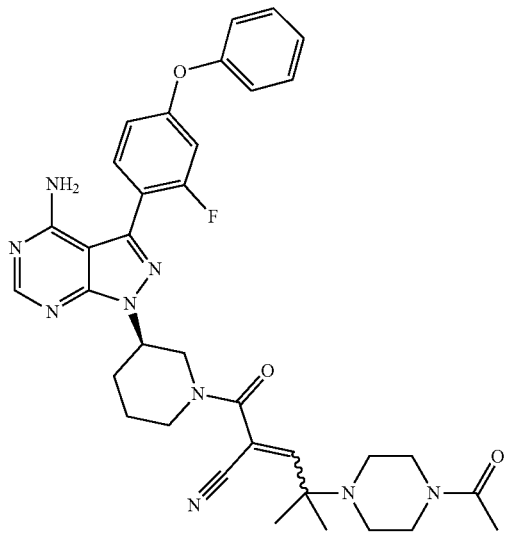 [SMILES: CC(=O)N1CCN(C(C)(C)C=C(C#N)C(=O)N2CCC[C@@H](n3nc(-c4ccc(Oc5ccccc5)cc4F)c4c(N)ncnc43)C2)CC1]

Proceeding as above in example 31 but substituting 1-(piperazin-1-yl)ethanone for 1-(oxetan-3-yl)piperazine in step 1, (R)-4-(4-acetylpiperazin-1-yl)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile is obtained. MS (pos. ion) m/z: 652 (M+1).

Example 33

Synthesis of (R)-methyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate

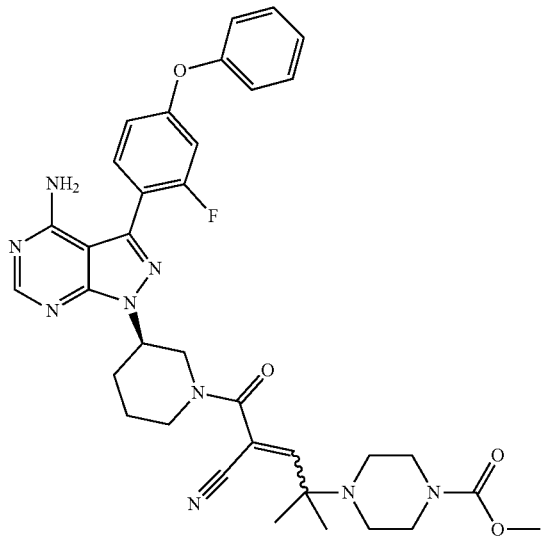 [SMILES: COC(=O)N1CCN(C(C)(C)C=C(C#N)C(=O)N2CCC[C@@H](n3nc(-c4ccc(Oc5ccccc5)cc4F)c4c(N)ncnc43)C2)CC1]

Proceeding as above in example 31 but substituting methyl piperazine-1-carboxylate for 1-(oxetan-3-yl)piperazine in step 1, (R)-methyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate is obtained. MS (pos. ion) m/z: 668 (M+1).

Example 34

Synthesis of (R)-2-(3-(4-amino-3-(2-fluoro-4-phenoxyphenyl)-1H-pyrazolo[3,4-d]pyrimidin-1-yl)piperidine-1-carbonyl)-4-(4-ethyl-3-oxopiperazin-1-yl)-4-methylpent-2-enenitrile

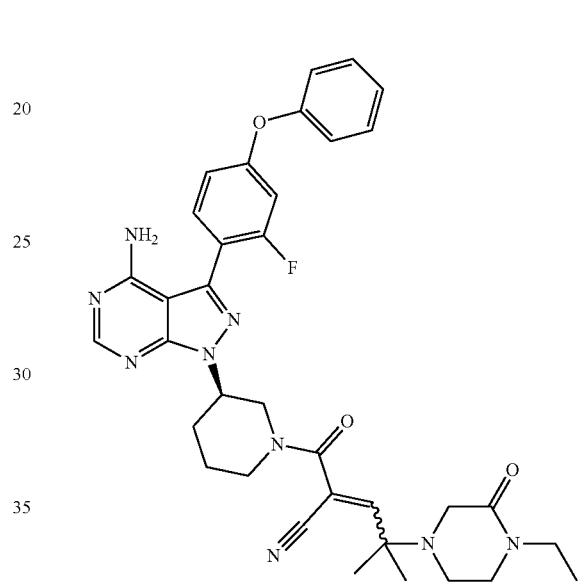

Step 1

To a slurry of tert-butyl 3-oxopiperazine-1-carboxylate (10 g, 49.9 mmol) in 250 mL of DMF, NaH (60% in mineral oil) (2.1 g, 52.4 mmol) was added in portions. The mixture was stirred for 15 min after completion of addition, cooled to 0° C. and iodoethane (5.62 mL, 69.92 mmol) slowly added over ~3 min. The resultant suspension was stirred at rt for 2 h. Water was slowly added (400 mL) and then 250 mL of 1:1 ethyl acetate:diethyl ether. The layers were separated and then the organic phase was washed with brine, dried over sodium sulfate, filtered and concentrated to afford tert-butyl 4-ethyl-3-oxopiperazine-1-carboxylate as a colorless oil weighing 6.4 g which was used directly in the next step.

Step 2

To a solution of tert-butyl 4-ethyl-3-oxo-piperazine-1-carboxylate (4.5 g, 19.9 mmol) in 1,4-Dioxane (10 mL) was added 10 mL of 4.0 M HCl/dioxane. After stirring 1 h at rt, an additional 5 mL of HCl in dioxane was added and a few mL of MeOH. The reaction was stirred another hour and then concentrated under reduced pressure. Dichloromethane was added and solvent removed to obtain the product as a foam weighing 2.2 g. This was partitioned between dichloromethane and aqueous sodium carbonate. The organic phase was washed with water, dried over sodium sulfate, filtered and concentrated to afford 1-ethylpiperazin-2-one as a foam.

Step 3 and 4

Proceeding as in example 31 but substituting 1-ethylpiperazin-2-one for 1-(oxetan-3-yl)piperazine in step 1, (R)-2-(3-(4-amino-3-(2-fluoro-4-phenoxyphenyl)-1H-pyrazolo[3,4-d]pyrimidin-1-yl)piperidine-1-carbonyl)-4-(4-ethyl-3-oxopiperazin-1-yl)-4-methylpent-2-enenitrile is obtained. MS (pos. ion) m/z: 652 (M+1).

Example 35

Synthesis of (R)-2-(3-(4-amino-3-(2-fluoro-4-phenoxyphenyl)-1H-pyrazolo[3,4-d]pyrimidin-1-yl)piperidine-1-carbonyl)-4-methyl-4-(3-oxopiperazin-1-yl)pent-2-enenitrile

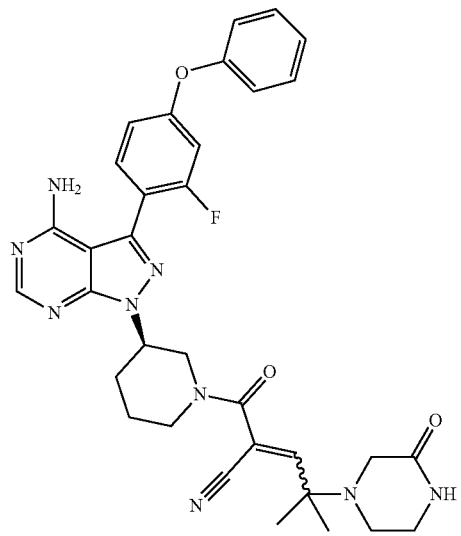 [SMILES: CC(C)(C=C(C#N)C(=O)N1CCC[C@@H](n2nc(-c3ccc(Oc4ccccc4)cc3F)c3c(N)ncnc32)C1)N1CCNC(=O)C1]

Proceeding as above in example 31 but substituting piperazin-2-one for 1-(oxetan-3-yl)piperazine in step 1, (R)-2-(3-(4-amino-3-(2-fluoro-4-phenoxyphenyl)-1H-pyrazolo[3,4-d]pyrimidin-1-yl)piperidine-1-carbonyl)-4-methyl-4-(3-oxopiperazin-1-yl)pent-2-enenitrile is obtained. MS (pos. ion) m/z: 624 (M+1).

Biological Examples

Example 1

Btk Enzymatic Activity Assay

A Caliper-based kinase assay (Caliper Life Sciences, Hopkinton, Mass.) was used to measure inhibition of Btk kinase activity of a compound of the present disclosure. Serial dilutions of test compounds were incubated with human recombinant Btk (0.5 nM), ATP (16 µM) and a phosphoacceptor peptide substrate FAM-GEEPLYWSF-PAKKK-NH$_2$ (1 µM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated. This value is presented as the IC$_{50}$. The IC$_{50}$ for certain compounds of the disclosure are provided below.

| Compound in Synthetic Example # | IC$_{50}$ (µm) | Compound in Synthetic Example # | IC$_{50}$ (µm) |
|---|---|---|---|
| 1 | 0.0031 | 9 | 0.0047 |
| 2 | 0.0041 | 10 | 0.0021 |
| 3 | 0.0081 | 11 | 0.0161 |
| 4 | 0.0003 | 12 | 0.004 |
| 5 | 0.0019 | 13 | 0.0006 |
| 6 | 0.0004 | 14 | 0.0204 |
| 7 | 0.0009 | 15 | 0.0041 |
| 8 | 0.0038 | 18 | 0.0007 |
| 19 | 0.0015 | 8A | 0.0009 |
| 13a | 0.0009 | 13b | 0.026 |
| 19a | 0.0056 | 20 | 0.0009 |
| 21 | 0.0007 | 22 | 0.0006 |
| 23 | 0.001 | 24 | 0.0012 |
| 25 | 0.0014 | 30 | 0.0052 |
| 31 | 0.0015 | 33 | 0.0020 |
| 32 | 0.0019 | 34 | 0.0013 |
| 35 | 0.0013 | | |

Example 2

Measurement of BTK Engagement in Human Ramos B Cell Line

The potency of compounds for inhibition of BTK activity can be assessed by binding of compounds to the target in human Ramos B cells that contain BTK. The extent of BTK occupancy is measured after treating the cells with compounds and detecting unoccupied BTK through binding of N-(2-(4-((E)-4-((R)-3-(4-amino-3-(4-phenoxyphenyl)-1H-pyrazolo[3,4-d]pyrimidin-1-yl)piperidin-1-yl)-4-oxobut-2-en-1-yl)piperazin-1-yl)ethyl)-6-(6-(5-(2-oxohexahydro-1H-thieno[3,4-d]imidazol-4-yl)pentanamido)hexanamido) hexanamide as the probe.

Briefly, Ramos cells were added to 96 well plates at a density of 10$^6$ cells per well. Serial dilutions of the compounds to be tested for potency were added such the final concentrations started at 1 µM and were serially diluted 3 fold for a total of 8 serial dilutions. The final DMSO concentration was 0.09% in each well. The compounds were allowed to interact with the cells for 1 hr. A BTK selective probe was then added to each well for a final concentration of 330 nM. Treatment with the probe was for 1 hr. The cells were then collected centrifugation and lysed for 15-30 minutes on ice. The binding of the probe to BTK was then detected by Alphascreen (Perkin Elmer) using a kit for the specific label on the BTK probe. The percent occupancy of BTK at each compound concentration was then calculated based on detection of unoccupied BTK bound by the labeled probe. BTK occupancy was then plotted as a function of the log of the compound concentration and the IC$_{50}$ values were calculated. The assay to measure BTK occupancy was modified to measure the durability of BTK binding in cells by removing the compound from the culture medium and incubating the cells for varying time periods followed by measurement of remaining occupancy as described above. For the durability measurements, the range of occupancy for the compounds disclosed herein (except for compounds disclosed in examples nos. 9, 14, 15, 3, 16, 17, 10a, 13b, 30, 22 and 26) after 18 hrs of washout was about 3-80%.

Example 3

Blockade of CD69 expression in human whole blood samples Activation of the B cell receptor leads to increased BTK activity, calcium mobilization and B cell activation (see Honigberg L. A., et. al., *Proc Natl Acad Sci USA.* 107:13075-80. 2010). BTK inhibitors have been shown to block B cell activation as measured by CD69 expression (see Karp, R., et. al., Inhibition of BTK with AVL-292 Translates to Protective Activity in Animal Models of Rheumatoid Arthritis. Inflammation Research Association Meeting, September, 2010). CD69 was expressed following B cell activation as a measure of BTK activity in whole blood. Aliquots of whole blood were pre-incubated with serial dilutions of test compound for 30 minutes followed by activation with anti-IgM (goat Fab'2, 50 µg/ml). Samples were incubated overnight at 37° C. and then stained with PE labeled anti-CD20 and APC labeled anti-CD69 (BD Pharmingen) for 30 minutes according to the manufacturer's directions. Whole blood was then lysed and cells gated on CD20 expression were quantified for CD 69 expression by FACS. The percent inhibition was calculated based on a DMSO control for no inhibition and plotted as a function of test compound concentration from which an $IC_{50}$ value was calculated. The range of $IC_{50}$ values for the compounds disclosed herein (except for compounds disclosed in examples nos. 2, 5, 17, 13b, 30, and 22), was about 1.4-0.08 µM.

Example 4

Inhibition of Mouse Collagen-Induced Arthritis

Inhibition of murine collagen-induced arthritis (mCIA) is a standard animal disease model for rheumatoid arthritis. Previous studies have demonstrated that inhibition of BTK is efficacious in blocking mCIA (see Honigberg L. A., et. al., *Proc Natl Acad Sci USA.* 107:13075-80. 2010). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by Elisa at the end of the study (Bolder BioPath, Boulder, Colo.).

Example 5

Recovery of Kinase Activity Upon Dialysis to Evaluate Irreversible Vs Reversible Covalent Binding A compound and/or pharmaceutically acceptable salt of the present disclosure at a concentration 10 times greater than its $IC_{50}$ value was added to a solution of protein kinase (5 nM) in a buffer containing 20 mM Hepes [pH 7.5], 5 mM $MgCl_2$, 0.01% Triton X-100, and 1 mM dithiothreitol. After 60 min at 22° C., the reactions were transferred to a dialysis cassette (0.1-0.5 mL Slide-A-Lyzer, MWCO 10 kDa, Pierce) and dialyzed against 1 L of buffer (20 mM Hepes [pH 7.5], 5 mM $MgCl_2$, 0.01% Triton X-100, and 1 mM dithiothreitol) at 22° C. The dialysis buffer was exchanged twice per day until the end of the experiment. Aliquots were removed from the dialysis cassettes every 24 h and analyzed for protein kinase activity. Kinase activity for each sample was normalized to the DMSO control for that time point and expressed as the mean±SD.

Results: Kinase activity recovered from inhibition by compounds of the present disclosure upon dialysis. Upon extensive dialysis at room temperature, kinase activity partially or completely recovered in a time-dependent manner from inhibition by an excess of compounds of the present disclosure.

Example 6

Mass Spectral Analysis

A protein kinase that is inhibited by compound and/or pharmaceutically acceptable salt of the present disclosure may be subjected to mass spectral analysis to assess the formation of permanent, irreversible covalent adducts. Suitable analytical methods to examine intact full protein or peptide fragments generated upon tryptic cleavage of the protein kinase are generally known in the art. Such methods identify permanent, irreversible covalent protein adducts by observing a mass peak that corresponds to the mass of a control sample plus the mass of an irreversible adduct. Two such methods are described below.

Mass Spectral Analysis of Intact Full Kinase
Method:
A protein kinase (5 µM) is incubated with a compound of the present disclosure (25 µM, 5 equiv) for 1 h at room temperature in buffer (20 mM Hepes [pH 8.0], 100 mM NaCl, 10 mM MgCl2). A control sample is also prepared which does not have a compound of the present disclosure. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software.

Results: High-resolution intact mass spectrometry analysis of a kinase that is inhibited by a compound of the present disclosure will reveal a spectrum similar to the kinase in the absence of inhibitor (e.g. control sample). There will be no formation of a new peak in the mass spectrum corresponding to the molecular mass of the kinase plus the molecular mass of the compound of Formula I. On the basis of this experiment, as can be applied to a compound and/or pharmaceutically acceptable salt as disclosed herein, no permanent, irreversible protein adduct will be apparent to one skilled in the art.

Mass Spectral Analysis of Kinase Tryptic Digest
Method:
A protein (10-100 pmols) is incubated with a compound and/or pharmaceutically acceptable salt of the present disclosure (100-1000 pmols, 10 equiv) for 3 h prior to tryptic digestion. Iodoacetamide may be used as the alkylating agent after compound incubation. A control sample is also prepared which does not utilize the compound and/or pharmaceutically acceptable salt of the present disclosure. For tryptic digests a 1 µl aliquot (3.3 pmols) ise diluted with 10 µl of 0.1% TFA prior to micro C18 Zip Tipping directly onto the MALDI target using alpha cyano-4-hydroxy cinnamic acid as the desorption matrix (5 mg/mol in 0.1% TFA:Acetonitrile 50:50) or Sinapinic acid as the desorption matrix (10 mg/mol in 0.1% TFA:Acetonitrile 50:50).

Results: High-resolution mass spectrometry analysis of the tryptic fragments of a kinase that is inhibited by a compound and/or pharmaceutically acceptable salt of the present disclosure will reveal a spectrum similar to the kinase in the absence of inhibitor (e.g. control sample). There will be no evidence of any modified peptides that are not present in the control sample. On the basis of this experiment, no permanent, irreversible protein adducts will be apparent to one skilled in the art.

Cellular assays are also optionally used to assess the inhibiting properties of a compound of the present disclosure. Cellular assays include cells from any appropriate source, including plant and animal cells (such as mammalian cells). The cellular assays are also optionally conducted in human cells. Cellular assays of BTK inhibition are well known in the art, and include methods in which an inhibitor is delivered into the cell (e.g. by electroporation, passive diffusion, microinjection and the like) and an activity endpoint is measured, such as the amount of phosphorylation of a cellular substrate, the amount of expression of a cellular protein, or some other change in the cellular phenotype known to be affected by the catalytic activity of BTK. For example, phosphorylation of a particular cellular substrate is optionally assessed using a detection antibody specific or the phosphorylated cellular substrate followed by western blotting techniques and visualization using any appropriate means (e.g. fluorescent detection of a fluorescently labeled antibody).

Measuring the reduction in the BTK catalytic activity in the presence of the present disclosure relative to the activity in the absence of the present disclosure is optionally performed using a variety of methods known in the art, such as the assays described in the Examples section below. Other methods for assaying BTK activity are known in the art.

Example 7

Determination of Drug-Kinase Residence Time

The following is a protocol that can be used to distinguish whether a compound displays a slow or non-existent dissociation rate from BTK, such as typically would occur if a covalent bond is formed between the compound and the target. The read-out for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM $MgCl_2$, 0.01% Triton X-100, and 1 mM EGTA.

The first step of the procedure was incubation of 500 nM BTK (Invitrogen Cat. #PV3587) with 1.5 µM of a compound of the present disclosure for 30 minutes in a volume of 10 µL. The mixture was then diluted 5-fold by addition of 40 µL of buffer. A 10 µL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For BTK, the competition solution contained 1.5 µM Tracer 178 (Invitrogen Cat. #PV5593), which is a proprietary high affinity ligand for BTK coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in BTK.

After addition of 10 µL of the competition solution to the Greiner plate, the mixture was incubated for one hour or greater to allow time for dissociation of non-covalent inhibitors and binding of the high affinity tracer. It is to be expected that covalent and slow dissociating inhibitors will block binding of the tracer while rapidly dissociating non-covalent inhibitors will not. Binding of the tracer to BTK is detected using TR-FRET between the Europium moiety of the Anti-histidine antibody and the AlexaFluor 647 group of Tracer 178. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of BTK from the reaction. If the compound is an irreversible covalent inhibitor, tracer will be completely blocked from binding to the target throughout the entire course of the experiment. If the compound is a reversible covalent inhibitor, the tracer will bind the target as the compound dissociates from the target.

Example 8

Reversibility of Binding

The following approach was developed to differentiate compounds that form irreversible covalent bond with their targets, such as non-cyano containing acrylamide compounds, from compound that form reversible covalent bond i.e., compounds and/or pharmaceutically acceptable salts of the present disclosure. Reactions were prepared with the protein target at a higher concentration than the compounds of interest. Both irreversible and reversible covalent compounds bound the target and became depleted from solution. The reactions were then treated with perturbations including both denaturation with 5 M guanidine hydrochloride and digestion with trypsin, disrupting proper folding of the target. It was found that the perturbation returned reversible covalent compounds to solution due to dissociation from the target while irreversible covalent compounds remained bound to the target. The concentration of compound in solution was assessed both preceding and following perturbation using high performance liquid chromatography (HPLC) coupled to tandem mass spectrometry. Using this technique, it was demonstrated that irreversible covalent compound is depleted from solution in both the native and perturbed state, while compounds and/or pharmaceutically acceptable salts disclosed herein were depleted in the folded state but returned to solution following perturbation of the target evidencing that compounds and/or pharmaceutically acceptable salts disclosed herein form reversible covalent bond.

| Compound | Compound in solution in the native state? | Compound in solution in the denatured or digested state? |
|---|---|---|
| (structure shown) | no | no |
| (Irreversible inhibitor) 10 | no | yes |

Formulation Examples

The following are representative pharmaceutical formulations containing a compound disclosed herein.

Parenteral Composition

To prepare a parenteral pharmaceutical composition suitable for administration by injection, 100 mg of a water-soluble salt of a compound disclosed herein is dissolved in 2% HPMC, 1% Tween 80 in DI water, pH 2.2 with MSA, q.s. to at least 20 mg/mL. The mixture is incorporated into a dosage unit form suitable for administration by injection.

Oral Composition

To prepare a pharmaceutical composition for oral delivery, 400 mg of a compound disclosed herein and the following ingredients are mixed intimately and pressed into single scored tablets.

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Inhalation Composition

To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 µl of spray for each application.

What is claimed:

1. A method for treating a disease in a patient, wherein the disease is selected from the group consisting of allergy, urticaria, antiphospholipid antibody syndrome and vasculitis, comprising administering to the patient in recognized need thereof a pharmaceutical composition comprising a pharmaceutically acceptable excipient and a therapeutically effective amount of a compound selected from the group consisting of:

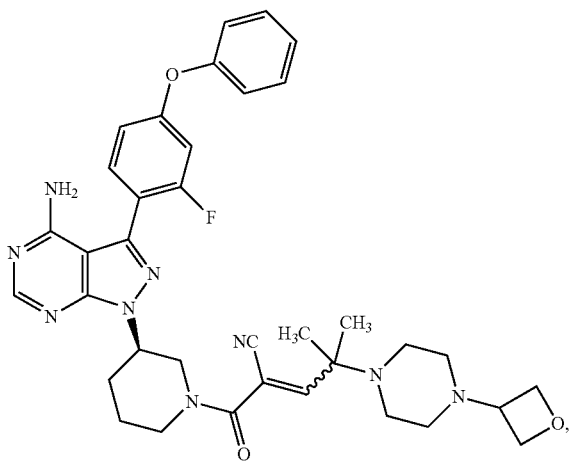 [SMILES: CC(C)(C=C(C#N)C(=O)N1CCC[C@@H](n2nc(-c3ccc(Oc4ccccc4)cc3F)c3c(N)ncnc32)C1)N1CCN(C2COC2)CC1]

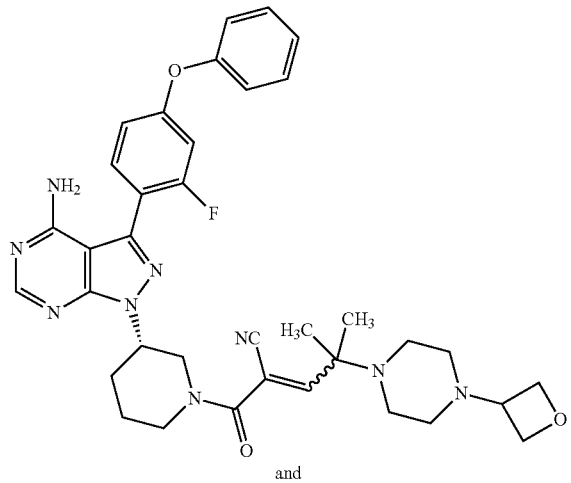

and

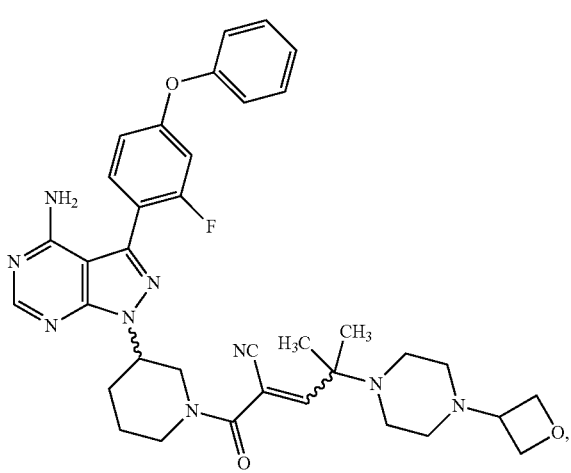

and/or a pharmaceutically acceptable salt and/or individual (E)-stereoisomer or (Z)-stereoisomer of any of the above compounds.

2. The method of claim 1, wherein the disease is allergy.

3. The method of claim 1, wherein the disease is urticaria.

4. The method of claim 1, wherein the disease is antiphospholipid antibody syndrome.

5. The method of claim 1, wherein the disease is vasculitis.

6. A method for treating a disease in a patient, wherein the disease is selected from the group consisting of allergy, urticaria, antiphospholipid antibody syndrome and vasculitis, comprising administering to the patient in recognized need thereof a pharmaceutical composition comprising a pharmaceutically acceptable excipient and a therapeutically effective amount of:

and/or a pharmaceutically acceptable salt thereof.

7. The method of claim 6, wherein the disease is allergy.

8. The method of claim 6, wherein the disease is urticaria.

9. The method of claim 6, wherein the disease is antiphospholipid antibody syndrome.

10. The method of claim 6, wherein the disease is vasculitis.

* * * * *